(12) United States Patent
Schriver et al.

(10) Patent No.: US 8,337,456 B2
(45) Date of Patent: *Dec. 25, 2012

(54) SYRINGE HAVING A PROXIMAL END WITH AN OUTWARD EXTENDING LIP

(75) Inventors: Ralph E. Schriver, Tarentum, PA (US); Michael A. Spohn, Butler, PA (US); Thomas P. Joyce, Wilkins Township, PA (US); Herbert M. Grubic, Pittsburgh, PA (US); John A. Haury, Sewickly, PA (US)

(73) Assignee: Medrad, Inc., Indianola, PA (US)

( * ) Notice: Subject to any disclaimer, the term of this patent is extended or adjusted under 35 U.S.C. 154(b) by 712 days.

This patent is subject to a terminal disclaimer.

(21) Appl. No.: 12/437,011

(22) Filed: May 7, 2009

(65) Prior Publication Data

US 2009/0216190 A1 Aug. 27, 2009

Related U.S. Application Data

(63) Continuation of application No. 10/818,477, filed on Apr. 5, 2004, now Pat. No. 7,563,249, which is a continuation-in-part of application No. 10/326,582, filed on Dec. 20, 2002, now Pat. No. 7,549,977.

(51) Int. Cl.
  *A61M 37/00* (2006.01)
  *A61M 1/00* (2006.01)
  *A61M 5/178* (2006.01)
(52) U.S. Cl. .................... 604/131; 604/151; 604/165.01

(58) Field of Classification Search .................. 604/131, 604/151, 152, 154, 155, 218
See application file for complete search history.

(56) References Cited

U.S. PATENT DOCUMENTS

| | | | |
|---|---|---|---|
| 2,702,547 A | 2/1955 | Glass | |
| 3,673,411 A | 6/1972 | Glasser | |
| 4,006,736 A * | 2/1977 | Kranys et al. | 600/432 |
| 4,080,967 A | 3/1978 | O'Leary | |
| 4,243,031 A | 1/1981 | Genese | |
| 4,351,332 A | 9/1982 | Whitney et al. | |
| 4,677,980 A | 7/1987 | Reilly et al. | |
| 4,747,830 A | 5/1988 | Gloyer et al. | |
| 4,858,127 A | 8/1989 | Kron et al. | |
| 5,002,528 A | 3/1991 | Palestrant | |
| 5,007,904 A | 4/1991 | Densmore et al. | |
| 5,106,379 A | 4/1992 | Leap | |
| 5,135,507 A | 8/1992 | Haber et al. | |

(Continued)

FOREIGN PATENT DOCUMENTS

GB 2108852 11/1981

(Continued)

OTHER PUBLICATIONS

International Search Report for Corresponding International Application PCT/US03/39984.

*Primary Examiner* — Kevin C Sirmons
*Assistant Examiner* — Andrew Gilbert
(74) *Attorney, Agent, or Firm* — David Schramm

(57) ABSTRACT

A syringe includes a body having a distal end, a proximal end and a center section therebetween, a plunger movably disposed in the body, and a hollow alignment flange for orienting and manipulating the syringe.

28 Claims, 33 Drawing Sheets

U.S. PATENT DOCUMENTS

| | | | |
|---|---|---|---|
| 5,300,031 A | 4/1994 | Neer et al. | |
| 5,342,309 A * | 8/1994 | Hausser | 604/110 |
| 5,383,858 A * | 1/1995 | Reilly et al. | 604/152 |
| 5,429,611 A | 7/1995 | Rait | |
| 5,433,712 A | 7/1995 | Stiles et al. | |
| 5,460,609 A | 10/1995 | O'Donnell | |
| 5,472,421 A | 12/1995 | Klearman et al. | |
| 5,515,851 A | 5/1996 | Goldstein | |
| 5,569,208 A | 10/1996 | Woelpper et al. | |
| 5,573,515 A | 11/1996 | Wilson et al. | |
| 5,607,399 A * | 3/1997 | Grimard et al. | 604/220 |
| 5,779,675 A | 7/1998 | Reilly et al. | |
| 5,800,397 A | 9/1998 | Wilson et al. | |
| 5,840,026 A | 11/1998 | Uber, III et al. | |
| 5,868,710 A | 2/1999 | Battiato et al. | |
| 5,873,861 A * | 2/1999 | Hitchins et al. | 604/218 |
| 5,899,885 A * | 5/1999 | Reilly et al. | 604/131 |
| 5,916,165 A | 6/1999 | Duchon et al. | |
| 5,938,639 A | 8/1999 | Reilly et al. | |
| 5,947,935 A | 9/1999 | Rhinehart et al. | |
| 6,096,011 A | 8/2000 | Trombley, III et al. | |
| 6,221,045 B1 | 4/2001 | Duchon et al. | |
| 6,264,637 B1 * | 7/2001 | Hogan | 604/191 |
| 6,336,913 B1 | 1/2002 | Spohn et al. | |
| 6,471,674 B1 | 10/2002 | Emig et al. | |
| 6,475,192 B1 | 11/2002 | Reilly et al. | |
| 6,808,513 B2 | 10/2004 | Reilly et al. | |
| 6,866,039 B1 | 3/2005 | Wright et al. | |
| 6,929,619 B2 | 8/2005 | Fago et al. | |
| 7,192,416 B1 | 3/2007 | Ashcraft, Jr. et al. | |
| 7,361,156 B2 * | 4/2008 | Joyce et al. | 604/131 |
| 7,563,249 B2 * | 7/2009 | Schriver et al. | 604/152 |
| 8,172,796 B2 * | 5/2012 | Schriver et al. | 604/131 |
| 2002/0128607 A1 | 9/2002 | Haury et al. | |
| 2003/0139706 A1 | 7/2003 | Gray | |
| 2004/0122370 A1 | 6/2004 | Joyce et al. | |
| 2004/0158205 A1 | 8/2004 | Savage | |
| 2008/0132850 A1 * | 6/2008 | Fumiyama et al. | 604/187 |

FOREIGN PATENT DOCUMENTS

| | | |
|---|---|---|
| WO | WO9707841 | 3/1997 |
| WO | WO0010629 | 3/2000 |
| WO | WO0204049 | 1/2002 |

* cited by examiner

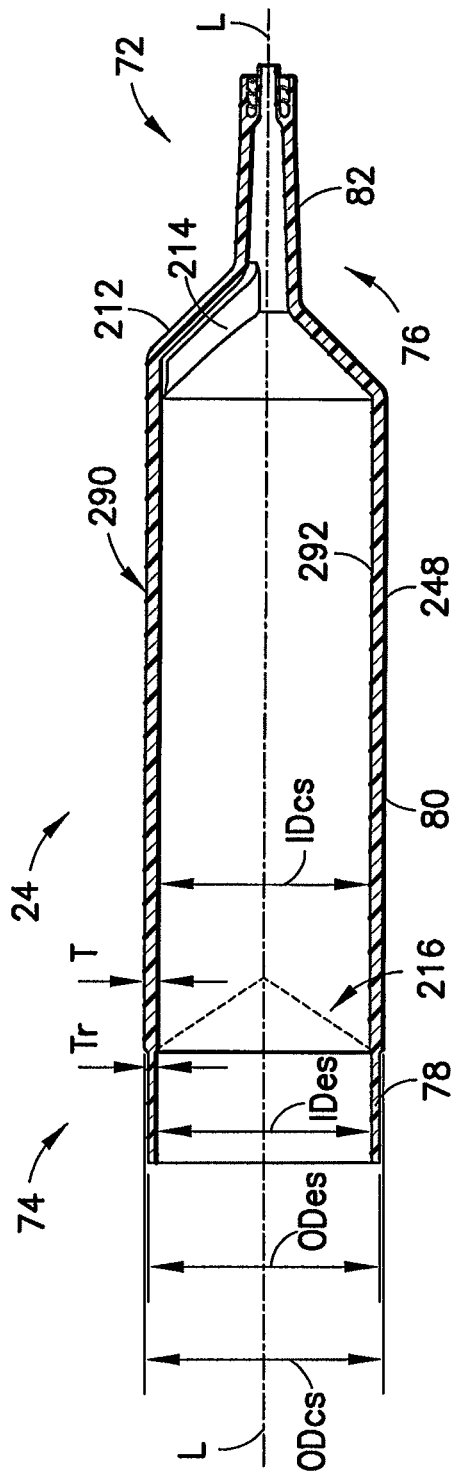
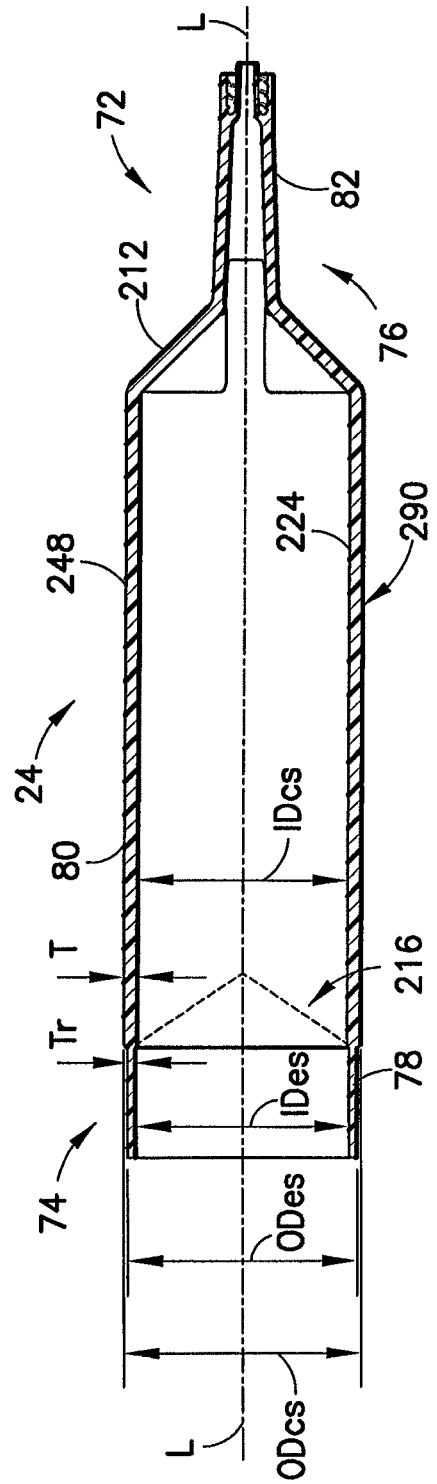
FIG.28
FIG.29

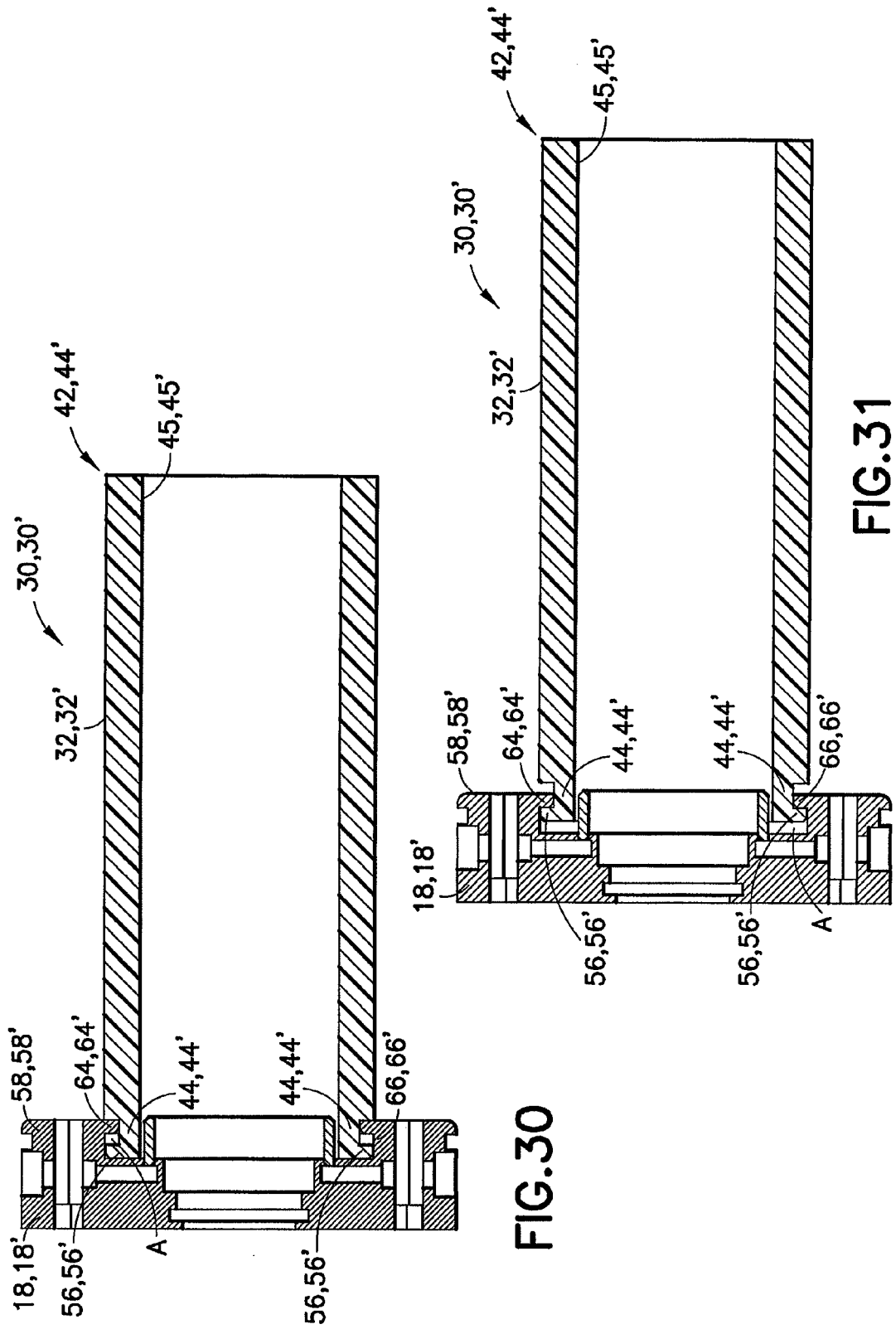

SYRINGE HAVING A PROXIMAL END WITH AN OUTWARD EXTENDING LIP

CROSS REFERENCE TO RELATED APPLICATIONS

This application is a continuation of U.S. patent application Ser. No. 10/818,477, filed on Apr. 5, 2004, now U.S. Pat. No. 7,563,249, which is a continuation-in-part of U.S. patent application Ser. No. 10/326,582, filed on Dec. 20, 2002, now U.S. Pat. No. 7,549,977, the disclosures of which are incorporated herein by reference.

BACKGROUND OF THE INVENTION

1. Technical Field of the Invention

This invention relates generally to pressure jacket systems for securing a syringe to an injector, to syringes for use with pressure jacket systems, and to methods of loading syringes in and removing syringes from pressure jacket systems. More specifically, the invention relates to front-loading pressure jacket systems and methods for allowing front loading and removal of syringes therefrom, and to syringes of special construction for use with, for example, pressure jackets.

2. Description of Related Art

In the medical field, patients are often injected with fluids in procedures such as angiography, computed tomography (CT), and magnetic resonance imaging (MRI). In such procedures, which require controlled injection of relatively large volumes of fluid into a patient, a catheter is used as a conduit for the fluid, which is connected to the syringe(s) by a connector tube. The syringe(s) is mounted on a motorized injector having an injector head. For compatibility with injectable fluids, syringes may be made of glass or polymeric materials, such as polypropylene, with a certain minimum wall thickness. The thickness is critical as typical pressures of up to 1200 p.s.i. (i.e., in angiographic procedures) are used to inject the fluids into a patient.

Pressure jackets are known in the art in at least two varieties, breech or rear loading and front loading, for substantially enclosing and retaining syringes while in use. A pressure jacket serves to limit radial expansion of a syringe, which may lead to bursting or to leaks of the pressurized fluid around the seal(s) of the syringe plunger. Another function of a pressure jacket is to prevent forward motion of the syringe. For example, a force of 2400 pounds is typically required to restrain the forward motion of a 150 ml syringe with a cross section of 2.0 in$^2$ at 1200 p.s.i.

U.S. Pat. No. 4,677,980, the contents of which are incorporated herein by reference, discloses an angiographic injector apparatus in which syringes are rear loaded into a pressure jacket of the injector. More specifically, the apparatus comprises a rotatable turret that carries a pair of the pressure jackets and which is rotatable so that when one of the pressure jackets, into which a syringe has been rear loaded, is in an injection position, the other pressure jacket is in a position in which an associated syringe may be rear loaded. Subsequently, when injection of contrast media from the first syringe is completed, the turret is rotated to move the first syringe to an unloading-loading position, with the second pressure jacket and the second syringe concurrently being moved into the injection position.

A disadvantage of rear loading pressure jacketed injectors is that, after an injection, the patient tubing typically must be disconnected from the syringe before the syringe may be extracted from the rear of the pressure jacket and discarded. Not only does this operation expend valuable operator time but fluids, such as contrast fluid and blood, may drip or spill from the syringe or the tubing after the tubing is removed from the syringe thereby creating a potentially unsafe or hazardous condition. Additionally, fluid spilled during loading and purging of air from the syringe may migrate inside the pressure jacket and the injector and require cleaning.

Motivated at least in part by this concern, front-loading injectors (pressure jacketed and non-pressure jacketed injectors) have been developed. U.S. Pat. Nos. 5,300,031; 5,779,675; and 5,800,397, for example, disclose front-loading pressure jacketed injector systems and U.S. Pat. No. 5,383,858 discloses front-loading pressure jacketed and non-pressure jacketed injector systems. The contents of U.S. Pat. Nos. 5,300,031; 5,779,675; 5,800,397; and 5,383,858 are incorporated herein by reference.

U.S. Pat. No. 5,300,031 discloses various embodiments of a pressure jacketed injector system wherein a syringe is loaded into and removed from an injector pressure jacket through an opening provided in the front end of the pressure jacket. To retain the syringe within the pressure jacket, for example during an injection operation, the front end of the syringe is locked to the front end of the pressure jacket.

U.S. Pat. No. 5,779,675 also discloses various embodiments of front-loading pressure jacketed injector systems. In a number of embodiments, for example as shown in FIGS. 12-16 of the '675 patent, one or more retaining plates or walls preferably supported by one or more arms or rods retain a syringe within the pressure jacket. The retaining plates or walls are preferably moved between open and closed positions to allow syringes to be inserted into and removed from the pressure jackets.

While front-loading pressure jacketed injector systems are known in the art, improvements in the design of such pressure jacketed injector systems and also in the design of syringes used in both pressure jacketed and non-pressure jacketed injector systems are and continue to be highly desirable.

SUMMARY OF THE INVENTION

The present invention relates generally to a fluid injection apparatus for use with a syringe having an injection section with an injection neck. The fluid injection apparatus comprises a housing defining an opening and a drive piston extendable through the opening for imparting motive forces to a syringe plunger disposed within the syringe. The fluid injection apparatus further comprises a pressure jacket assembly associated with the housing for securing the syringe during an injection procedure. The pressure jacket assembly comprises a pressure jacket associated with the housing and aligned with the opening, at least one support arm associated with and extending outward from the housing, and a syringe retaining member associated with the at least one support arm. The syringe retaining member defines a syringe receiving slot for receiving at least the injection neck of the syringe and viewing at least a portion of the injection section. The at least one support arm is movable, preferably selectively, between a first position wherein the syringe retaining member prevents removal of the syringe from the pressure jacket and a second position wherein the syringe is removable from the pressure jacket. In a preferred embodiment, the pressure jacket assembly is a front-loading pressure jacket assembly.

The pressure jacket may have a distal end defining a syringe receiving opening for receiving the syringe and a proximal end associated with the housing. The pressure jacket assembly may further comprise a faceplate associated with the injector, for example connected to the housing. The faceplate may define a passage aligned with the opening and through which the injector drive piston is extendable. The injector drive piston may have an axially directed light source for illuminating the syringe.

The pressure jacket may be removably associated with the faceplate. The pressure jacket assembly may further comprise a coupling member adapted to removably associate the pressure jacket with the faceplate. The pressure jacket may be removably associated with the coupling member by a threaded connection therewith. The coupling member may be removably associated with the faceplate by a bayonet socket connection. The pressure jacket may be removably associated with the faceplate and is preferably movable axially with respect to the faceplate.

Alternatively, the faceplate may be considered to be part of the injector instead of the pressure jacket assembly. In particular, the faceplate may be removably or permanently connected to, or integrally formed with the injector housing. In addition, the coupling member may be configured and used as an adapter to mount different or varying types of pressure jackets and/or syringes to or on the injector. To that end, the fluid injection apparatus of the present invention may be provided with one or more coupling members for adapting the injector for various pressure jackets and/or syringes.

The at least one support arm may comprise at least one light source positioned to illuminate the syringe received in the pressure jacket. The at least one light source may also be located on the syringe retaining member and positioned to illuminate the syringe, in addition to or as an alternative to locating the at least one light source on the at least one support arm. The at least one support arm preferably extends laterally along a longitudinal side of the pressure jacket in the first position. Preferably, the pressure jacket is made of substantially clear plastic. The pressure jacket may comprise a light-diffusing means, device, or structure for diffusing light from a light source external to the pressure jacket.

The at least one support arm may comprise a pair of support arms adapted to support the syringe retaining member. For example, the support arms may pivotally support the syringe retaining member. The support arms each have a distal end and a proximal end. The fluid injection apparatus may further comprise an axle assembly adapted to connect the proximal ends of the support arms together in the housing. The axle assembly is preferably configured to selectively move the support arms between the first and second positions. The support arms may extend laterally along longitudinal sides of the pressure jacket in the first position. At least one of the support arms preferably has at least one light source positioned to illuminate the syringe received in the pressure jacket. The at least one light source may be located on the syringe retaining member and positioned to illuminate the syringe received in the pressure jacket.

The axle assembly may comprise an axle linkage extending between the proximal ends of the support arms. The axle linkage preferably comprises a base member and two outward extending axles. The base member may define a recess through which the drive piston is extendable and retractable in any position of the support arms.

The proximal ends of the support arms preferably each define a circular aperture for rotatably receiving a pair of circular members, respectively. The circular members are preferably supported on the axle linkage. The central axis of the axle linkage may be offset from the rotational axis of the circular members for converting rotational movement of the circular members to translational movement of the support arms. The axle linkage may be supported on the faceplate by a pair of support brackets. The circular members may be associated with the support brackets, respectively, to limit the rotational movement of the circular members in the circular apertures. The circular members may each comprise a ball detent adapted for a mating connection with detent openings defined in the support brackets for providing at least a tactile indication that the support arms are set in the first position.

The proximal ends of the support arms are preferably associated with the faceplate to guide the movement of the support arms between the first and second positions. To this end, the proximal ends of the support arms may define guide tracks and the faceplate may have cross pins associated therewith, which cooperate with the guide tracks, respectively, to guide the movement of the support arms between the first and second positions. The faceplate may further comprise a pair of ball detents adapted for a mating connection with detent openings defined in the proximal ends of the support arms, respectively, to prevent uncontrolled movement of the support arms to the second position.

Another embodiment of the fluid injection apparatus comprises a housing and a pressure jacket assembly associated with the housing for securing the syringe during an injection procedure. The pressure jacket assembly may comprise a pressure jacket associated with the housing, at least one support arm extending outward from the injector housing, and at least one light source associated with the at least one support arm and positioned to illuminate the syringe received in the pressure jacket and, in particular, fluid and possibly any air bubbles in the fluid. The light source may be a plurality of light emitting diodes, a mini-fluorescent light bar, a fiber-optic bed, and the like.

The at least one support arm may comprise a pair of support arms. At least one of the support arms may have the at least one light source. The support arms may be movable between a first position extending laterally along longitudinal sides of the pressure jacket and a second position depending below the pressure jacket, such that with the support arms in the first position the syringe is illuminated substantially along a central axis thereof during an injection procedure.

To diffuse the light entering the syringe through the wall of the pressure jacket, a light-diffusing means, device, or structure may be associated with the pressure jacket. The light-diffusing device may be associated with the inner or outer walls or surfaces of the pressure jacket, or disposed between the inner and outer walls or surfaces of the pressure jacket. In one embodiment, the light-diffusing device may be a lens attached to the inner surface of the pressure jacket and extending longitudinally along the inner surface of the pressure jacket. In another embodiment, the light-diffusing device may be an etched area formed on the inner surface of the pressure jacket and extending longitudinally along the inner surface of the pressure jacket. In further embodiment, the light-diffusing device may be a light-diffusing strip made, for example, of white polycarbonate material. The inner wall or surface of the pressure jacket may define a groove, which may extend longitudinally along the inner surface. The light-diffusing strip may be disposed in the groove for diffusing light passing through the wall of the pressure jacket. The groove may be trapezoidal shaped in cross section and have two inward facing projections for retaining the light-diffusing strip in the groove.

A further embodiment of the fluid injection apparatus of the present invention includes one or more of a syringe, a syringe plunger movably received in the syringe, an injector, and a pressure jacket assembly. The syringe has a cylindrical body with an injection section comprising a conical portion and an injection neck. The conical portion defines an alignment flange or tab member. The alignment flange preferably operates as an orientation "key" that is received within the syringe receiving slot in the syringe retaining member of the pressure jacket assembly. The syringe plunger is located in the cylindrical body and has a coupling end with a pair of rigid or flexible coupling members defining a slot therebetween, as shown and described in U.S. Pat. Nos. 4,677,980 and 5,873, 861, the contents of which are incorporated herein by reference. With the slot substantially aligned with the alignment flange, the alignment flange provides an indication, such as a visual indication, of the orientation of the slot. When the "key" or alignment flange is aligned with or received in the syringe receiving slot, the syringe plunger is substantially oriented with the drive piston of the injector (i.e., a desired mounting position) such that the drive piston and syringe plunger may be correctly and securely engaged.

The injector comprises a housing defining an opening and a drive piston extendable through the central opening for imparting motive forces to the syringe plunger disposed within the syringe body. The pressure jacket assembly is associated with the housing for securing the syringe during the injection procedure. The pressure jacket assembly comprises a pressure jacket associated with the housing and aligned with the opening, at least one support arm associated with and extending outward from the housing, and a syringe retaining member associated with the at least one support arm. The syringe retaining member defines a syringe receiving slot for receiving the injection neck of the syringe and viewing at least a portion of the injection section. The syringe retaining member may further define at least one opening spaced radially outward from the syringe receiving slot for viewing the injection section, for example to observe whether fluid or air is present in the syringe body. The at least one support arm is movable, preferably selectively, between a first position wherein the syringe retaining member prevents removal of the syringe from the pressure jacket and a second position wherein the syringe is removable from the pressure jacket. The alignment of the alignment flange with the syringe receiving slot in the syringe retaining member automatically orients the coupling members in a desired mounting position with the slot therebetween oriented to receive the drive piston.

The conical portion of the syringe body preferably further comprises a light-sensitive fluid dot as an optical aid. The alignment flange may extend outward sufficiently from the conical portion to be grasped by a user of the syringe and used as a handle for manipulating the syringe. The coupling members may each have an inward projecting engagement arm for engaging the drive piston. The coupling members may be flexible coupling members.

The present invention also relates generally to pressure jackets for receiving syringes used in fluid injection procedures. The pressure jacket of the present invention comprises an elongated body and light-diffusing means, device, or structure provided on the body. The elongated body is formed of substantially clear plastic material. The light-diffusing means or device is adapted to diffuse light passing therethrough emitted by an externally located light source. The light-diffusing means or device may be a lens, which may be provided on an inner surface of the body and extend longitudinally along the inner surface of the body. The lens may also be provided on the outer surface of the body or disposed between the inner and outer surfaces of the body. Alternatively, the light-diffusing means or device may be an etched area on the body. The etched area may be provided on the inner surface of the body and extend longitudinally along the inner surface of the body. A groove may be defined in the inner surface of the body. The light-diffusing means or device may be a light-diffusing strip disposed in the groove. The groove may extend longitudinally along the inner surface of the body. The light-diffusing strip may be white polycarbonate material. The groove may be trapezoidal shaped in cross section and have two inward facing projections for retaining the light-diffusing strip in the groove.

Additionally, the present invention relates generally to syringes for use with pressure jackets, preferably front-loading pressure jackets, and fluid injection apparatuses incorporating pressure jackets, preferably front-loading pressure jackets. The syringe of the present invention is generally comprised of a body, a plunger, and an alignment flange. The body is preferably a cylindrical main body. A conical portion is connected to the main body and a discharge outlet is connected to the conical portion. The plunger is movably disposed within at least a portion of the main body. The alignment flange is disposed on and extends outward from at least a portion of the conical portion. The alignment flange defines a hollow area therein. The hollow area may be operable to retain air bubbles therein. The syringe may be disposable (i.e., single use) or reusable for injecting a liquid medium into the body of a patient.

In another embodiment, the syringe comprises a body having a distal end and a proximal end. The body has an injection section at the distal end and an expansion section at the proximal end. The injection section and the expansion section are connected by a center section or main body of relatively uniform outer diameter. The wall thickness of the body preferably narrows to a reduced wall thickness at the expansion section such that an inner diameter of the expansion section is larger than the inner diameter of the center section for allowing the expansion section to expand when a syringe plunger is disposed in the expansion section.

The reduced wall thickness preferably allows the expansion section to expand to an outer diameter no greater than approximately the outer diameter of the center section when the plunger is disposed in the expansion section. The body may be made of a deformable material permitting the expansion section to expand to an outer diameter no greater than approximately the outer diameter of the center section when the plunger is disposed in the expansion section. The body may be made of substantially clear plastic such as polypropylene, such as polyethylene terephthalate (PET), polyethylene, polycarbonate, and the like.

An outer surface of the body may be tapered or stepped inward toward a central axis of the body and an inner surface of the body may be tapered or stepped outward away from the central axis of the body to form the reduced wall thickness. Alternatively, only the inner surface of the body may be tapered or stepped outward away from the central axis of the body to form the reduced wall thickness. An additional alternative is to only taper or step the outer surface.

The plunger is preferably movably received in the body and seated for storage in the expansion section of the syringe body. The plunger may have a coupling end comprising a pair of coupling members defining a slot therebetween. The slot is preferably substantially aligned with the alignment flange such that the alignment flange provides an indication of the orientation of the slot when loading the syringe into a pressure jacket, such as a front-loading pressure jacket.

Yet another embodiment of the syringe comprises a cylindrical body and a plunger movably received in the cylindrical body. The body has an injection section at a distal end and an expansion section at a proximal end. The plunger may be seated for storage in the expansion section. The injection section and the expansion section are connected by a cylindrical center section or main body of relatively uniform outer diameter. The injection section comprises a conical portion and an injection neck. The conical portion preferably comprises an alignment flange extending outward from at least a portion of the conical portion. The plunger has a coupling end preferably with a pair of flexible coupling members defining a slot therebetween for engaging a drive piston of an injector. The slot is preferably substantially aligned with the alignment flange such that the alignment flange provides an indication, such as a visual indication, of the orientation of the slot to facilitate engagement of the flexible coupling members with the drive piston of the injector. The coupling members may each have an inward facing or projecting engagement arm for engaging the drive piston of the injector. The wall thickness of the body preferably narrows to a reduced wall thickness at the expansion section such that an inner diameter of the expansion section is larger than the inner diameter of the center section for allowing the expansion section to expand under radial outward force exerted by the plunger.

Furthermore, the present invention relates generally to a method of loading a syringe to an injector. The syringe comprises a cylindrical main body, a conical portion connected to the main body, and a discharge outlet connected to the conical portion. A plunger is movably disposed within at least a portion of the main body. An alignment flange is disposed on and extends outward from at least a portion of the conical portion. The injector comprises a pressure jacket assembly comprising a pressure jacket associated with the injector, at least one support arm associated with and extending outward from the injector, and a syringe retaining member associated with the at least one support arm. The syringe retaining member defines a syringe receiving slot for receiving the discharge outlet of the syringe. The at least one support arm is movable between a first position wherein the syringe retaining member prevents removal of the syringe from the pressure jacket and a second position wherein the syringe is removable from the pressure jacket. The method may comprise the steps of: inserting a proximal end of the syringe into the pressure jacket; aligning the alignment flange on the syringe with the syringe receiving slot in the syringe retaining member; and moving the at least one support arm and the syringe retaining member from the second position to the first position. The method may further comprise the steps of moving the at least one support arm and the syringe retaining member from the first position to the second position, and removing the syringe from the pressure jacket. Further, the method may comprise the steps of connecting the plunger to the drive piston of the injector, and advancing the drive piston to move the plunger within the syringe. Moreover, the method may comprise the step of retracting the plunger within the syringe with the drive piston.

Another embodiment of the fluid injection apparatus of the present invention generally comprises a housing and a pressure jacket assembly associated with the housing. The housing defines an opening through which a drive piston of the injector is extendable for imparting motive forces to a syringe plunger disposed within the syringe. The pressure jacket assembly associated with the housing secures the syringe during an injection procedure. The pressure jacket assembly generally comprises a pressure jacket associated with the housing and aligned with the opening, at least one support arm pivotally associated with and extending outward from the housing, and a syringe retaining member pivotally associated with the at least one support arm. The syringe retaining member defines a syringe receiving slot for receiving the injection neck of the syringe and viewing at least a portion of the injection section. The at least one support arm is movable between a first position wherein the syringe retaining member prevents removal of the syringe from the pressure jacket and a second position wherein the syringe is removable from the pressure jacket.

The syringe retaining member may be pivotal between a syringe retaining position cooperating with the injection section of the syringe and a pivoted position disengaged sufficiently from the injection section to allow the at least one support arm to pivot to the second position. The at least one support arm may comprise a proximal end pivotally associated with the housing and a distal end extending outward from the housing. The proximal end may have an increased cross section relative to the distal end such that an upward moment is created about the pivotal association with the housing for maintaining the at least one support arm in the first position. The at least one support arm preferably extends laterally along a longitudinal side of the pressure jacket in the first position.

A spring means (i.e., a spring) or like device may be provided between the syringe retaining member and the at least one support arm for orienting the syringe retaining member with respect to the at least one support arm. The spring may be adapted to bias the syringe retaining member to a position substantially perpendicular to the at least one support arm. The spring may be a leaf spring, a coil spring, a torsion spring, and the like. The spring may be positioned in a cavity defined in the syringe retaining member adjacent the distal end of the at least one support arm.

The at least one support arm may be pivotally connected to the faceplate associated with or connected to the housing. The pressure jacket may be removably associated with the faceplate. The pressure jacket assembly may further comprise a coupling member adapted to removably associate the pressure jacket with the faceplate. The pressure jacket may be removably associated with the coupling member by a threaded connection. The coupling member may be removably associated with the faceplate by a bayonet socket connection. The pressure jacket may be removably associated with the faceplate and movable axially with respect to the faceplate.

The at least one support arm may comprise a pair of support arms each having a proximal end pivotally associated with the housing and a distal end extending outward from the housing. The proximal ends of the support arms may have increased cross sections (i.e., increased mass) relative to the distal ends such that an upward moment is created about the pivotal associations with the housing for maintaining the support arms in the first position. The syringe retaining member may be pivotally connected to the distal ends of the support arms and interconnect the distal ends. A pair of springs (i.e., spring means) or similar device may act between the support arms, respectively, and the syringe retaining member for orienting the syringe retaining member with respect to the support arms. The springs or similar device may be adapted to bias the syringe retaining member to a position substantially perpendicular to the support arms. The springs may be positioned in respective cavities defined in the syringe retaining member adjacent distal ends of the support arms.

The pressure jacket has a distal end defining a syringe receiving opening for receiving the syringe. The distal end of the pressure jacket may define a beveled portion forming an acute angle with a central axis of the pressure jacket. With the at least one support arm in the first position, the syringe retaining member may be pivotal between a syringe retaining position wherein a syringe facing side of the syringe retaining member cooperates substantially with the injection section and prevents removal of the syringe from the pressure jacket, and a pivoted position pivoted away from the injection section and toward the beveled portion for allowing the at least one support arm to pivot to the second position. The beveled portion may define an acute angle of about 60° or less with the central axis of the pressure jacket.

The support arms may comprise at least one light source positioned to illuminate the syringe received in the pressure jacket and extend laterally along longitudinal sides of the pressure jacket in the first position. The syringe retaining member may comprise at least one light source positioned to illuminate the syringe received in the pressure jacket. The pressure jacket is preferably made of substantially clear plastic, such as polypropylene, polyethylene, and polycarbonate, as indicated previously. The pressure jacket may further comprise a light-diffusing device for diffusing light from a light external to the pressure jacket.

In still a further embodiment, the fluid injection apparatus includes an injector, and a pressure jacket associated with the injector, for example removably associated with the injector. The injector has a housing defining an opening for a drive piston extendable from the injector housing for imparting motive forces to a syringe plunger disposed within the syringe. The pressure jacket secures the syringe during an injection procedure. The pressure jacket has a distal end defining a syringe receiving opening for receiving the syringe, and a proximal end associated with the injector housing, for example removably, and generally aligned with the opening.

The fluid injection apparatus may further include a syringe sensor generally adapted to be engaged by the syringe when the syringe is loaded into the pressure jacket. The syringe sensor may, for example, extend from the injector housing. The syringe sensor may generally be adapted to generate a signal indicating the presence of the syringe in the pressure jacket. For example, the syringe sensor may be spring-loaded, such that contact by the syringe and axial displacement of the syringe into the pressure jacket will activate the syringe sensor.

Additionally, the fluid injection apparatus may include a connecting arrangement between the proximal end of the pressure jacket and the injector housing. For example, the proximal end of the pressure jacket may define an engagement recess and the injector housing may include an engagement tab cooperating with the engagement recess for maintaining a removable association between the pressure jacket and the injector housing. The engagement tab may be biased to engage the engagement recess. Further, the proximal end of the pressure jacket may define a cam surface for displacing the engagement tab radially, for example, when the pressure jacket is connected to the injector housing.

The fluid injection apparatus may also include at least one light source associated with the injector housing and positioned to illuminate the syringe received in the pressure jacket. The at least one light source may be contained within a light source housing associated with the injector housing. The at least one light source may include at least one light emitting diode disposed within the light source housing. The at least one light source may include, for example, at least one light source angled toward the pressure jacket, and/or at least one forward-directed light source. The at least one light source may include opposing light sources disposed substantially at opposite sides of the pressure jacket. The opposing light sources may be contained within respective light source housings associated with the injector housing. The opposing light sources may each include at least one light emitting diode disposed within the respective light source housings.

In another embodiment of the pressure jacket of the present invention, the pressure jacket includes a body, for example an elongated cylindrical-shaped body, formed of substantially clear plastic and adapted to receive the syringe, and a light-diffusing structure provided on the body and adapted to diffuse light passing therethrough emitted by an externally located light source, such as one of the light sources discussed previously. The light-diffusing structure may be provided substantially at the proximal end of the pressure jacket body. The light-diffusing structure may be formed by a recessed portion of the pressure jacket body. The recessed portion may define a beveled surface for diffusing the light into the syringe when loaded in the pressure jacket. The beveled surface extends at least partially about the circumference of the pressure jacket, but could extend completely around the circumference of the pressure jacket. The light-diffusing structure may be located substantially opposite from the at least one light source, when the pressure jacket is connected to the injector.

In another embodiment of the syringe of the present invention, the syringe includes a body, for example an elongated cylindrical-shaped body, having a distal end and a proximal end. The syringe body may have an expansion section and an outward extending lip provided substantially at the proximal end. The distal and proximal ends of the syringe body may be connected by a center section of the syringe body. A wall thickness of the syringe body may narrow to a reduced wall thickness at the expansion section, such that an inner diameter of the expansion section is larger than the inner diameter of the center section, for allowing the expansion section to expand when a plunger is disposed in the expansion section.

The syringe may have a plunger movably disposed in the syringe body, and substantially seated in the expansion section in a pre-use state of the syringe. The plunger may have a coupling end including a pair of coupling members, preferably flexible coupling members, generally adapted to engage the drive piston of the injector. See, for example, U.S. Pat. Nos. 5,873,861 and 5,947,935, the contents of which are incorporated herein by reference.

The syringe body may include a conical portion forming a discharge outlet, generally at the distal end. The conical portion may have a light-sensitive fluid dot as an optical aid. The syringe body may be further formed with an alignment flange or handle formed on the conical portion and defining a hollow area therein. The alignment flange may extend outward from the conical portion sufficiently to be grasped by a user of the syringe and used as a handle for manipulating the syringe. See, for example, U.S. Patent Application Publication No. 2002-0177811, the contents of which are incorporated herein by reference. The coupling members at the coupling end of the plunger may define a slot therebetween, with the slot substantially aligned with the alignment flange such that the alignment flange provides an indication of the orientation of the slot.

The outward extending lip formed generally at the proximal end of the syringe body may have an outer diameter no greater than the outer diameter of the center section of the syringe. The reduced wall thickness of the syringe body wall preferably allows the expansion section to expand to an outer diameter no greater than approximately the outer diameter of the center section when a syringe plunger is disposed in the expansion section. The syringe body may further be made of a deformable material, permitting the expansion section to expand to an outer diameter no greater than approximately the outer diameter of the center section when a syringe plunger is disposed in the expansion section. The outer surface of the syringe body may be tapered or stepped inward toward a central axis of the body and/or an inner surface of the body may be tapered or stepped outward away from the central axis of the body to form the reduced wall thickness. In another embodiment of the invention, a method is generally directed to associating a syringe with the fluid injection apparatus of the present invention. The method generally comprises providing the injector discussed previously, including the housing and further including the pressure jacket adapted to secure the syringe during an injection procedure. The pressure jacket has a distal end defining a syringe receiving opening for receiving the syringe and a proximal end. The injector generally further comprises a syringe sensor associated with the housing. The method may further comprise loading the syringe into the syringe receiving opening in the distal end of the pressure jacket, and engaging the syringe sensor with the syringe when the syringe is substantially fully received in the pressure jacket.

The method may further include the syringe sensor generating a signal indicating the presence of the syringe in the pressure jacket when the syringe engages the syringe sensor. Additionally, the method may include illuminating the syringe with at least one light source associated with the housing. Further, the method may include associating the proximal end of the pressure jacket with the housing, for example in a removable configuration with the housing. The proximal end of the pressure jacket may define an engagement recess and the housing may comprise a mating engagement tab, such that the engagement tab engages the engagement recess when the pressure jacket proximal end is associated with the housing.

In a further aspect, the present invention is directed to an anti-rotation connection between the drive piston generally extendable from the injector, typically outward from the injector housing, and the syringe plunger disposed within the syringe. The anti-rotation connection or arrangement generally comprises the drive piston extendable from the injector and the syringe plunger disposed within the syringe. The drive piston has a plunger engaging end, and the syringe plunger has a distal end and a proximal end adapted for engagement by the plunger engaging end of the drive piston. The plunger engaging end of the drive piston comprises an anti-rotation element adapted to interact with the proximal end of the plunger to prevent rotation of the plunger in the syringe.

The anti-rotation element may include at least one pin extending between the plunger engaging end of the drive piston and the proximal end of the syringe plunger when the drive piston is engaged with the syringe plunger. The at least one pin may engage at least one pin receiving opening in the proximal end of the syringe plunger when the drive piston is engaged with the syringe plunger. The at least one pin may extend from an end plate forming the plunger engaging end of the drive piston.

The proximal end of the syringe plunger may include at least one coupling member adapted for engagement by the plunger engaging end of the drive piston. The anti-rotation element may further include at least one pin extending from the plunger engaging end of the drive piston and associated with the at least one coupling member when the drive piston is engaged with the syringe plunger. The at least one pin may extend from the end plate, which may form the plunger engaging end of the drive piston. The anti-rotation element may include opposing pins extending from the plunger engaging end and the at least one coupling member may include a pair of coupling members, such that the opposing pins are associated with the respective coupling members when the drive piston is engaged with the syringe plunger. The coupling members may be flexible coupling members.

In a further configuration, the anti-rotation element may comprise at least one tab formed on the plunger engaging end of the drive piston and associated with the at least one coupling member when the drive piston is engaged with the syringe plunger. The at least one tab may extend from the end plate, which may form the plunger engaging end of the drive piston. The anti-rotation element may include opposing tabs formed on the plunger engaging end of the drive piston and the at least one coupling member may include a pair of coupling members, such that the opposing tabs are associated with the respective coupling members when the drive piston is engaged with the syringe plunger.

In a still further configuration, the anti-rotation element may comprise an edge formed on the drive piston, and which is generally adapted to be engaged by the at least one coupling member when the drive piston is engaged with the syringe plunger to prevent rotation of the syringe plunger in the syringe. The edge may be formed on the end plate, which may form the plunger engaging end of the drive piston. The anti-rotation element may be configured as opposing edges formed on the drive piston, for example on the end plate which may form the plunger engaging end, and the at least one coupling member may include a pair of coupling members. The opposing edges may be adapted to be engaged by the respective coupling members when the drive piston is engaged with the syringe plunger to prevent rotation of the syringe plunger in the syringe.

Further details and advantages of the present invention will become apparent from the following detailed description when read in conjunction with the drawings, wherein like part are designated with like reference characters and numerals, and distinct embodiments are designated with primed reference characters and numerals.

BRIEF DESCRIPTION OF THE DRAWINGS

FIG. 28 is a cross sectional view taken along line 28-28 in FIG. 21;

FIG. 29 is a cross sectional view taken along line 29-29 in FIG. 21;

FIG. 30 is a cross sectional view of another embodiment of the fluid injection apparatus and pressure jacket assembly of the present invention wherein the pressure jacket of the pressure jacket assembly cooperates directly with a faceplate of the fluid injection apparatus;

FIG. 31 is cross sectional view of the pressure jacket assembly and faceplate of FIG. 30 showing the position of the pressure jacket during operation of the fluid injection apparatus;

DETAILED DESCRIPTION OF THE PREFERRED EMBODIMENTS

Figure 1:
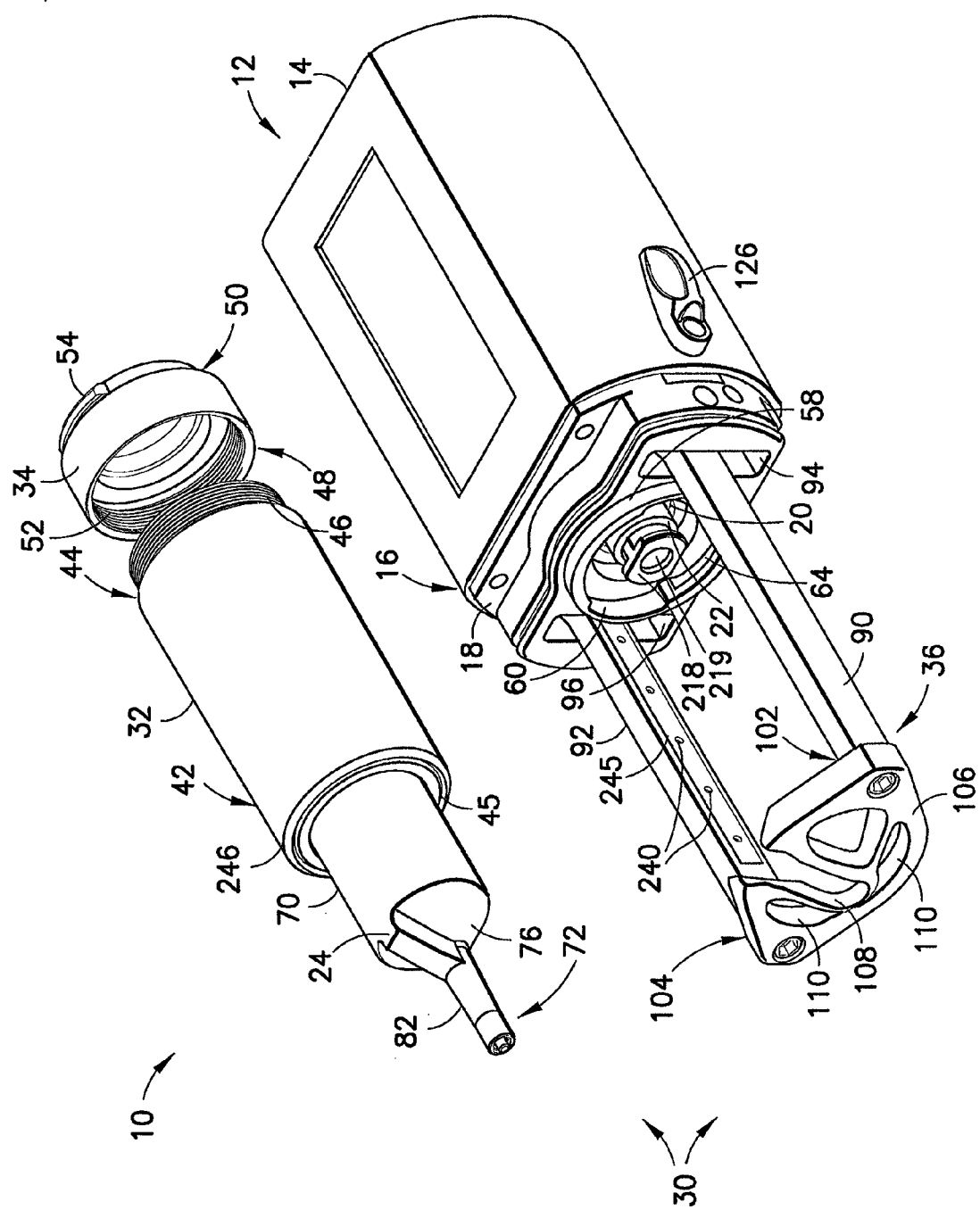
FIG. 1 is an exploded perspective view of a fluid injection apparatus in accordance with an embodiment of the present invention.
Figure 2:
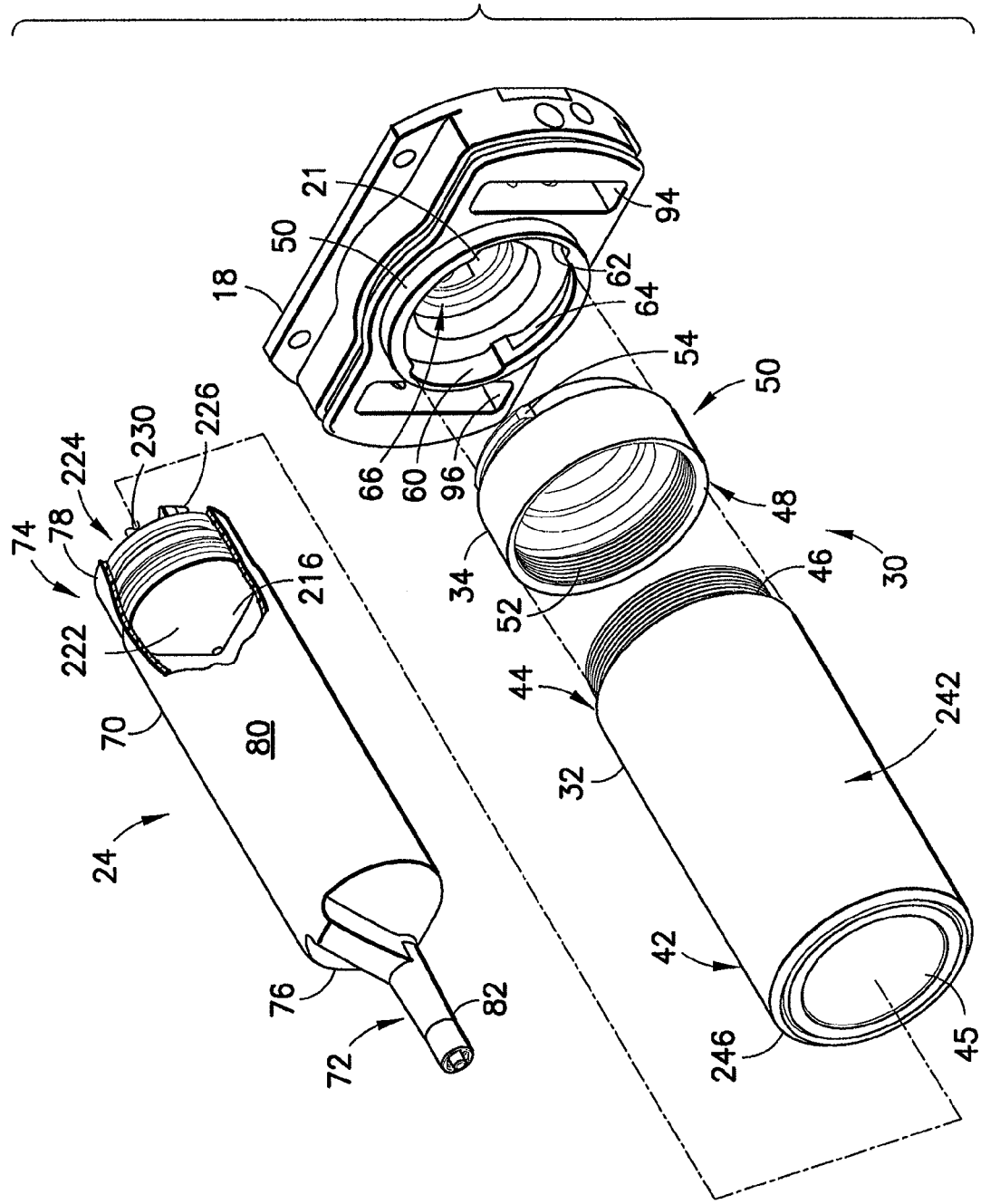
FIG. 2 is an exploded perspective view of a syringe and a pressure jacket assembly associated with the fluid injection apparatus of FIG. 1.
Figure 3:
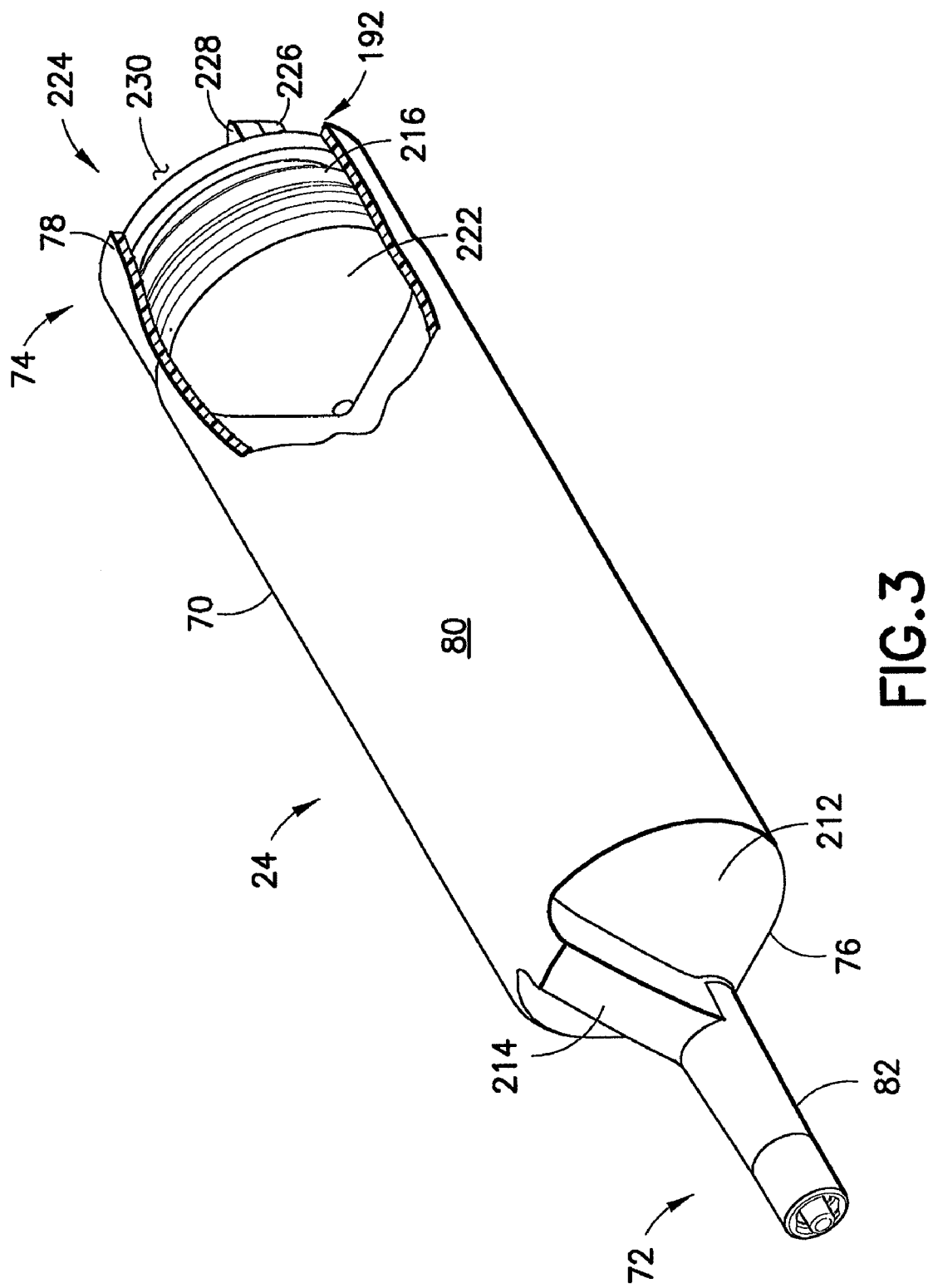
FIG. 3 is a perspective and partially cutaway view of the syringe associated with the fluid injection apparatus of FIG. 1.
Figure 4:
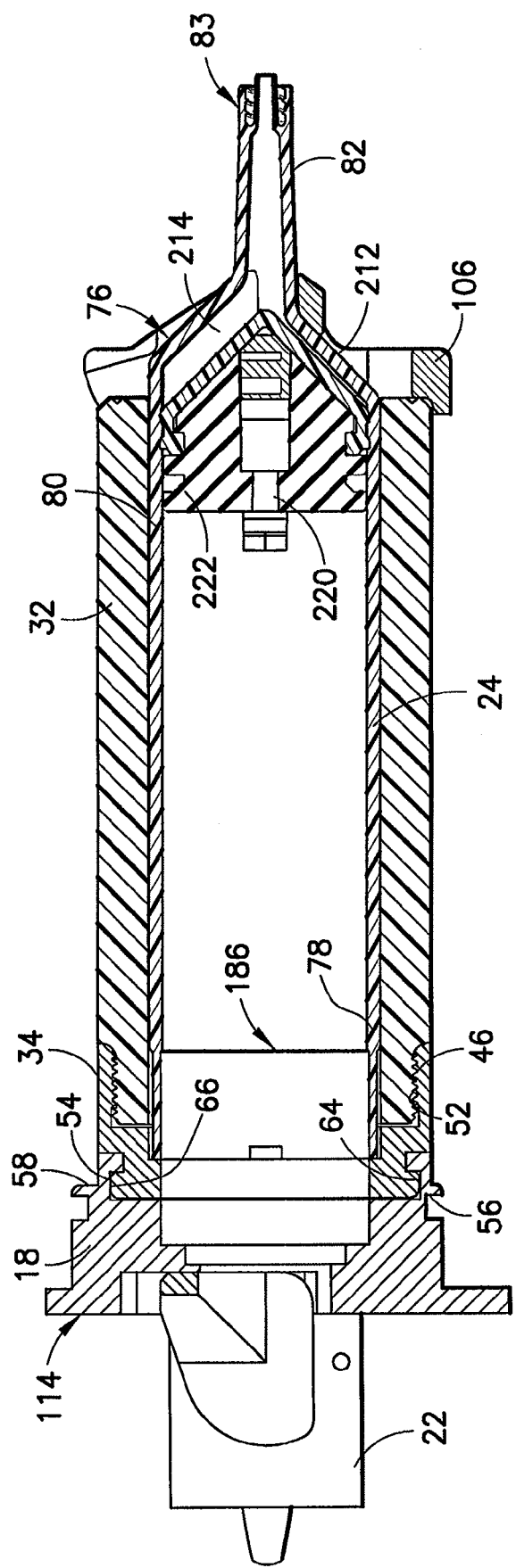
FIG. 4 is a cross sectional view taken along a longitudinal axis of the fluid injection apparatus of FIG. 1.

FIG. 1 shows a fluid injection apparatus 10 in accordance with the present invention. The fluid injection apparatus 10 includes an injector head 12, which may be supported on a support structure (not shown). The injector head 12 includes an injector housing 14 having a front end 16. A faceplate 18 is attached to the front end 16 of the injector housing 14 and encloses the front end 16 of the injector housing 14. The faceplate 18 may be secured to the front end 16 of the injector housing 14 by conventional means (i.e., mechanical fasteners and the like) or be integrally formed with the injector housing 14.

Referring to FIGS. 1-4, the injector housing 14 has a central opening 20 aligned with a central passage 21 defined by the faceplate 18 and through which an injector drive piston 22 of the injector head 12 is extendable and retractable. The details of the injector head 12 and, more particularly, the injector drive piston 22 are described in U.S. Pat. No. 5,383,858, which was previously incorporated herein by reference. As described further herein, the injector head 12 is generally used to actuate a syringe 24 used in a fluid injection procedure, such as an angiographic procedure.

A pressure jacket assembly 30 is associated with the injector head 12. The pressure jacket assembly 30 supports the syringe 24 and mounts the syringe 24 to the injector head 12. Generally, the pressure jacket assembly 30 extends outward from the front end 16 of the injector housing 14 and is used to support the syringe 24 during the fluid injection procedure. The pressure jacket assembly 30 is generally comprised by the faceplate 18, discussed previously, a cylindrical pressure jacket 32, a coupling member 34 for connecting the pressure jacket 32 to the faceplate 18, and a syringe support structure 36 for supporting the syringe 24. The faceplate 18 may be considered to be a part of the injector housing 14, as well as form part of the pressure jacket assembly 30.

The pressure jacket 32 is a generally cylindrical structure having a front or distal end 42 and a rear or proximal end 44. The distal end 42 of the pressure jacket 32 defines a syringe receiving mouth or opening 45 for receiving the syringe 24 into the pressure jacket 32. The proximal end 44 of the pressure jacket 32 faces the faceplate 18 and is configured to engage fixedly with the coupling member 34. For this purpose, the proximal end 44 may have an externally threaded portion 46. The pressure jacket 32 has an inner diameter sized to smoothly but snugly receive the outer diameter of the syringe 24. A typical clearance between the outer diameter of the syringe 24 and the inner diameter of the pressure jacket 32 may be about 0.005 inch. The pressure jacket 32 is preferably made of a material capable of restraining the outward expansion of the syringe 24 during an injection procedure. As discussed previously, the syringe 24 by itself is typically not capable of withstanding the high pressures associated with certain fluid injection procedures, such as angiography. The pressure jacket 32, as is well known in the art, is used to limit the radial expansion of the syringe 24, which may lead to bursting or leaking, as discussed previously.

The syringe 24 may be made of a relatively inexpensive medical grade plastic material and may be disposable (i.e., single use). Alternatively, the syringe 24 may be a multi-patient use syringe. Typical plastics for the syringe 24 include polypropylene, polyethylene, and polycarbonate. The pressure jacket 32 is preferably reusable and made of a material capable of withstanding pressures up to about 1200 p.s.i. and higher. For example, the pressure jacket 32 may be made of metal such as steel or aluminum. However, as explained further hereinafter, it is advantageous for the syringe 24 to be visible through the pressure jacket 32 so that an operator of the fluid injection apparatus 10 may view the syringe 24 during an injection procedure. Accordingly, the pressure jacket 32 is preferably made of a substantially clear plastic material, such as polycarbonate, for viewing the syringe 24 during an injection procedure.

The coupling member 34 is cylindrical shaped in a similar manner to the pressure jacket 32. The coupling member 34 has a front or distal end 48 configured for connection to the pressure jacket 32 and a rear or proximal end 50 configured for connection to the faceplate 18. The distal end 48 includes internal threads forming an internally threaded portion 52. The threaded portion 46 at the proximal end 44 of the pressure jacket 32 cooperates with the internally threaded portion 52 of the coupling member 34 to secure the pressure jacket 32 to the coupling member 34. The threaded connection between the pressure jacket 32 and coupling member 34 is a presently preferred embodiment of the present invention and equivalent connections may be used in place of the above-discussed threaded connection. Suitable equivalent connections include, but are not limited to: permanent bond, interference press fit, traditional mechanical fasteners, and the like. The coupling member 34 may be made of any of the materials discussed previously in connection with the pressure jacket 32. In an alternative embodiment, the coupling member 34 may be eliminated and the pressure jacket 32 connected directly to the faceplate 18, an example of which is shown in FIGS. 30 and 31 discussed hereinafter.

Referring to FIGS. 1-6, the coupling member 34 is removably connected to the faceplate 18 attached to the front end 16 of the injector housing 14. A presently preferred embodiment of the present invention provides a bayonet socket connection between the coupling member 34 and the faceplate 18. In particular, for this purpose, the proximal end 50 of the coupling member 34 includes a pair of oppositely facing bayonet projections 54, 56. The bayonet projections 54, 56 are positioned to cooperate with a flange 58 extending outward from the faceplate 18. The flange 58 defines a pair of opposing recesses 60, 62 for receiving the bayonet projections 54, 56 into the flange 58. The flange 58 further defines a pair of bayonet receiving slots 64, 66. The bayonet projections 54, 56 may be inserted into the flange 58 through the recesses 60, 62 and then rotated to engage the bayonet receiving slots 64, 66 to secure the coupling member 34 to the faceplate 18. The bayonet receiving slots 64, 66 may be formed so that, for example, a one-quarter turn of the coupling member 34 after being inserted into the recesses 60, 62 will secure the coupling member 34 to the faceplate 18.

The bayonet receiving slots 64, 66 are preferably configured such that when the bayonet projections 54, 56 are received in the bayonet receiving slots 64, 66 and the threaded portion 46 of the proximal end 44 of the pressure jacket 32 is threaded into the threaded portion 52 of the coupling member 34, the bayonet projections 54, 56 fully seat in the bayonet receiving slots 64, 66. Accordingly, the engagement of the bayonet projections 54, 56 in the bayonet receiving slots 64, 66 facilitates threading of the proximal end 44 of the pressure jacket 32 into the distal end 48 of the coupling member 34. The threaded connection between the pressure jacket 32 and coupling member 34 may be conventional (i.e., clockwise rotation for engagement, counterclockwise rotation for disengagement). However, the conventional arrangement may be reversed in accordance with the present invention. Additionally, the bayonet socket connection between the coupling member 34 and the faceplate 18 may be replaced by any suitably equivalent mechanical connection, such as by a threaded connection, magnets, traditional mechanical fasteners, snap ring, and the like.

The syringe 24 used in the fluid injector apparatus 10 generally includes an elongated, cylindrical syringe body 70 having a front or distal end 72 and a rear or proximal end 74. The syringe body 70 has an injection section 76 formed at the distal end 72. As discussed further herein, the syringe body 70 preferably includes an expansion section 78 at the proximal end 74. A generally cylindrical center section or main body 80 of the syringe body 70 connects the injection section 76 and the expansion section 78. The center section (i.e., main body) 80 has a relatively uniform outer diameter. The injection section 76 tapers to form an elongated injection neck 82, which has a relatively small inner diameter compared to the inner diameter of the center section 80. The injection section 76 and injection neck 82 generally form the discharge outlet of the syringe 24. The syringe support structure 36 is configured to support the injection section 76 of the syringe body 70. The injection neck 82 includes a distal end structure 83, which is adapted to connect via a suitable luer fitting to tubing, for example connected to a catheter used in an angiographic procedure. A suitable luer fitting for this purpose is disclosed in published PCT Application No. PCT/US99/18892 (WO 00/10629), entitled "Connector And Tubing Assembly For With A Syringe", the disclosure of which is incorporated herein by reference in its entirety.

The syringe support structure 36 includes at least one, and preferably two, support arms 90, 92 extending outward from the injector housing 14. In particular, the support arms 90, 92 extend through respective front openings 94, 96 defined in the faceplate 18 attached to the injector housing 14. The front openings 94, 96 in the faceplate 18 are substantially vertically oriented to allow the support arms 90, 92 to pivot up and down with respect to the injector housing 14. The support arms 90, 92 have rear or proximal ends 98, 100, respectively, extending into the injector housing 14, and distal ends 102, 104, respectively, projecting outward from the injector housing 14. The distal ends 102, 104 of the support arms 90, 92 are interconnected by a syringe retaining wall or member 106. The syringe retaining member 106 may be affixed to the support arms 90, 92 by conventional mechanical fasteners (i.e., bolts) and the like. The syringe retaining member 106 defines a central syringe receiving slot 108 that is substantially vertically oriented and is configured to receive and support the injection neck 82 of the injection section 76. The syringe retaining member 106 further defines one or more openings 110, which are spaced radially outward from the syringe receiving slot 108. The syringe receiving slot 108 and openings 110 permit the operator of the fluid injection apparatus 10 to view the syringe 24 during an injection procedure. More importantly, the syringe receiving slot 108 and openings 110 permit the operator to view the injection section 76 during an injection procedure.

Referring to FIGS. 1-11, as stated, the proximal ends 98, 100 of the support arms 90, 92 extend into the injector housing 14. The support arms 90, 92 are generally configured to be movable between a first position (FIG. 7) wherein the syringe retaining member 106 receives the injection neck 82 and cooperates with the injection section 76 of the syringe body 70 and prevents removal of the syringe 24 from the pressure jacket 32, and a second, rotated position (FIG. 8) wherein the injection neck 82 and the injection section 76 of the syringe body 70 are disengaged sufficiently from the syringe receiving slot 108 and syringe retaining member 106 to allow removal of the syringe 24 from the pressure jacket 32. In particular, in the second position, the injection neck 82 is disengaged sufficiently from the syringe receiving slot 108 and the injection section 76 is sufficiently decoupled from the syringe retaining member 106 to allow the syringe 24 to be removed easily from the front loading pressure jacket 32. Preferably, in the second position, the support arms 90, 92 and syringe retaining member 106 are spaced a distance below the pressure jacket 32 and syringe 24. With the support arms 90, 92 in the first position, the syringe support structure 36 is in a syringe-engaged position. When the support arms 90, 92 are moved to the second position, the syringe support structure 36 is generally in a syringe-disengaged or removal position or configuration.

The support arms 90, 92 generally follow a two-dimensional (i.e., X and Y) movement in their motion between the first and second positions. In particular, the support arms 90, 92 are configured to move from the first (i.e., syringe-engaged) position to the second (i.e., syringe-removal) position by generally moving distally or linearly forward away from the faceplate 18 and then generally rotate downward from the pressure jacket 32 and syringe 24. Similarly, the support arms 90, 92 are configured to return to the first position by rotating upward toward the pressure jacket 32 and syringe 24 and then moving proximally toward the faceplate 18 so that the injection neck 82 is again received in the syringe receiving slot 108 and the retaining member 106 cooperates with the injection section 76 to secure the syringe 24.

An axle assembly 112 interconnects the proximal ends 98, 100 of the support arms 90, 92 and facilitates the two-dimensional movement exhibited by the support arms 90, 92 generally described hereinabove. The axle assembly 112 is located within the injector housing 14 and is connected to an internal facing side 114 of the faceplate 18. The axle assembly 112 is comprised generally of an axle linkage 116, a pair of circular-shaped members 118, 120, a pair of support brackets 122, 124, and an actuation handle 126.

The axle linkage 116 is comprised of a U-shaped base member 128 having two outward extending axles 130, 132, one for each of the support arms 90, 92. The base member 128 defines an opening or recess 134 through which the injector drive piston 22 of the injector head 12 may extend and retract to actuate a syringe plunger located in the syringe 24 as discussed further herein. The axles 130, 132 each include a polygonal shaped portion 136 for engaging the circular members 118, 120.

The proximal ends 98, 100 of the support arms 90, 92 define respective circular apertures 138, 140, which are configured to receive the circular members 118, 120, respectively. The circular members 118, 120 are seated for rotation in the circular apertures 138, 140. The circular members 118, 120 define polygonal shaped openings 142, 144, respectively, to receive the polygonal shaped portions 136 of the axles 130, 132. At least one of the axles 130, 132, in this case axle 130, is configured to support the actuation handle 126. For this purpose, axle 130 extends outward from the injector housing 14. The actuation handle 126 is seated over the end of the axle 130 and is preferably secured fixedly to the end of the axle 130 so that rotational motion imparted to the actuation handle 126 is transmitted to the axles 130, 132. Bushings 146, 148 may be provided on the axles 130, 132 to facilitate the rotational movement of the axles 130, 132 with respect to the support brackets 122, 124.

In the assembled axle assembly 112, the proximal ends 98, 100 of the support arms 90, 92 are received in recesses 150, 152 defined by the support brackets 122, 124, respectively. The support brackets 122, 124 are generally U-shaped in horizontal cross section and each have two sidewalls 154, 156 interconnected by an end wall 158. The sidewalls 154, 156 of each of the support brackets 122, 124 define aligned openings 160, 162. The sidewalls 154, 156 and end walls 158 of the brackets 122, 124 form the respective recesses 150, 152. The axles 130, 132 extend through the aligned openings 160, 162 in the support brackets 122, 124 to interconnect the proximal ends 98, 100 of the support arms 90, 92.

The U-shaped base member 128 of the axle linkage 116 is located between the support brackets 122, 124 with the opening 134 defined by the base member 128 aligned with the central passage 21 in the faceplate 18 to permit the injector drive piston 22 to extend outward from and retract into the injector housing 14. The support brackets 122, 124 are secured fixedly to the internal facing side 114 of the faceplate 18 to support the axle assembly 112. The support brackets 122, 124 may be secured to the internal facing side 114 of the faceplate 18 by conventional mechanical fasteners 164 (i.e., bolts) and the like. The opening 134 defined by the base member 128 is formed to permit the injector drive piston 22 to extend or retract regardless of the position of the syringe support structure 36 (i.e., syringe-engaged or removal positions). The base member 128 is generally square or rectangular shaped and the opening 134 is formed by two substantially semi-circular-shaped passages formed into the rectangular-shaped base member 128.

The circular members 118, 120 facilitate the two-dimensional movement exhibited by the support arms 90, 92 identified previously. As stated previously, the support arms 90, 92 are generally movable from a first (i.e., syringe-engaged) position to a second (i.e., syringe-removal) position by first moving distally away from the faceplate 18 and then downward to the second position depending below the pressure jacket 32 and syringe 24. The circular members 118, 120 are cams that enable the axial or distal movement of the support arms 90, 92. The circular members 118, 120 also provide for the rotational or pivotal movement of the support arms 90, 92 to the second position depending below the pressure jacket 32 and syringe 24, which allows the syringe 24 to be removed from the pressure jacket 32. The distal or axial movement of the support arms 90, 92 is important because it permits the syringe retaining member 106 to disengage from the injection section 76 of the syringe body 70 and to clear the distal end 42 of the pressure jacket 32 when the support arms 90, 92 are rotated to the second position depending below the pressure jacket 32 and syringe 24.

As indicated previously, the circular members 118, 120 rotate on their respective axles 130, 132 when the handle 126 is actuated. The openings 142, 144, through which the respective axles 130, 132 extend, are offset from the center of the circular members 118, 120. Thus, the center of the circular members 118, 120 is a distance away from the rotational axis of the circular members 118, 120 (i.e., axles 130, 132). This distance is the "throw" of the "camming" circular members 118, 120 and is the axial distance that the support arms 90, 92 move distally or linearly away from the faceplate 18 under the camming action of the circular members 118, 120. This axial distance, as indicated previously, permits the syringe retaining member 106 to disengage from the injection section 76 of the syringe body 70 and clear the distal end 42 of the pressure jacket 32 when the support arms 90, 92 are pivoted to the second position.

Figure 9:
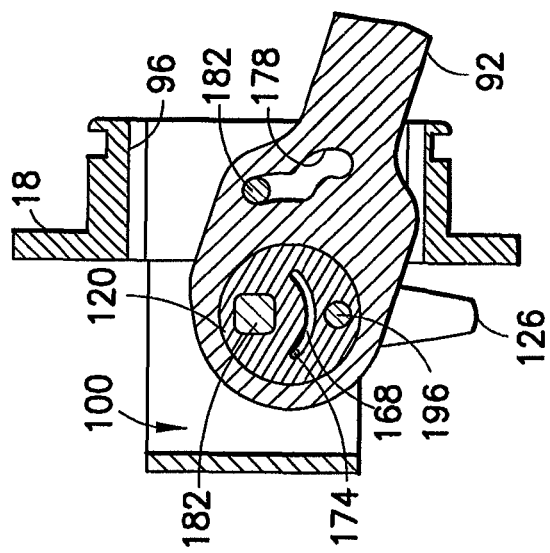
FIG. 9 is a cross sectional view of a portion of a support arm of the syringe support structure showing the support arm in a first position.
Figure 10:
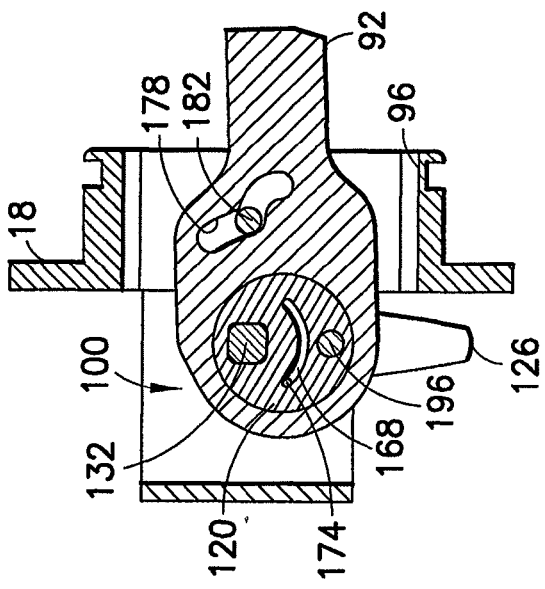
FIG. 10 is a cross sectional view showing the support arm of FIG. 9 in an intermediate position.
Figure 11:
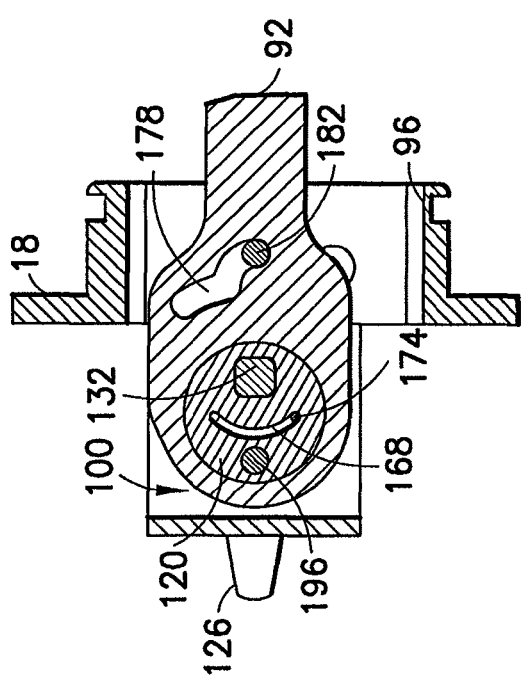
FIG. 11 is a cross sectional view showing the support arm of FIG. 9 in a second, pivoted position.
Figure 12:
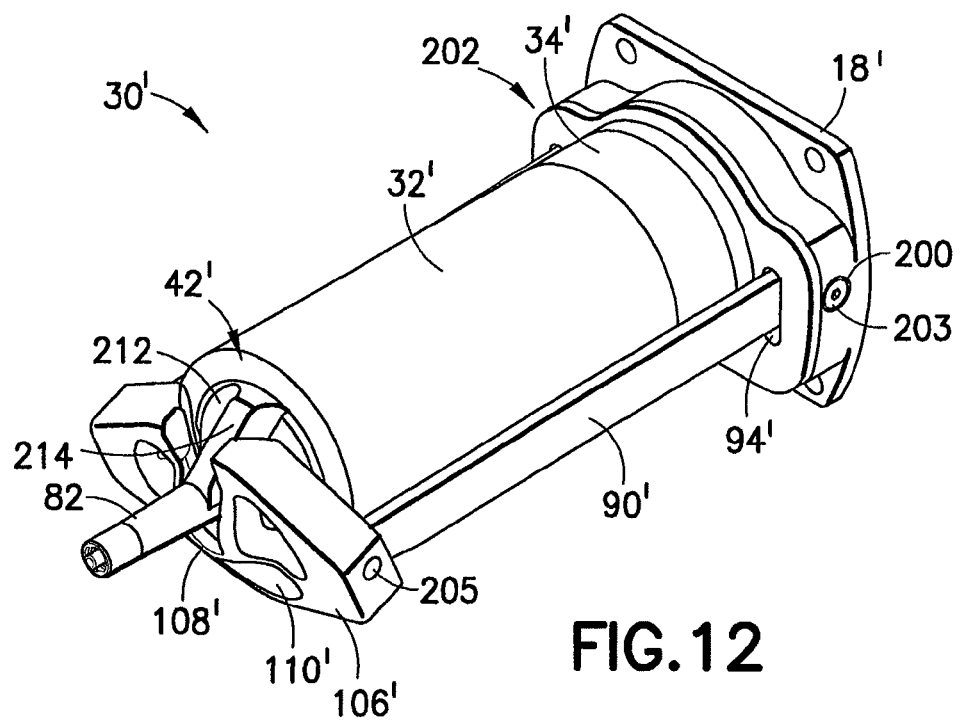
FIG. 12 is a perspective view of another embodiment of the fluid injection apparatus and pressure jacket assembly of the present invention showing the syringe support structure of the pressure jacket assembly in the syringe-engaged position supporting a syringe.

Referring, in particular, to FIGS. 9-11, one of the circular members 118, 120, (i.e., circular member 120) and one of the support arms 90, 92 (i.e., support arm 92) are shown. FIG. 9 shows the circular member 120 in a "closed" position, which corresponds generally to the support arms 90, 92 and syringe retaining member 106 being in the first or syringe-engaged position. FIG. 10 shows the circular member 120 in an "open" position, which corresponds generally with the support arms 90, 92 and syringe retaining member 106 being in an intermediate position moved distally forward from the faceplate 18, or in the second, syringe-removal position. FIG. 11 shows the orientation of support arm 92 after being moved fully to the second position. The support arm 90 follows an identical movement to the support arm 92.

As stated, in the closed position of the circular members 118, 120, the support arms 90, 92 and syringe retaining member 106 are in the first, syringe-engaged position, wherein the syringe retaining member 106 engages the injection section 76 of the syringe body 70. To move the support arms 90, 92 and syringe retaining member 106 to the second, syringe-removal position, the handle 126 is rotated, for example, in a clockwise direction. This clockwise movement causes the circular members 118, 120 to rotate with their respective axles 130, 132. The support arms 90, 92 and syringe retaining member 106 move distally or linearly forward by the camming action of the circular members 118, 120 to the intermediate position. The intermediate position of the support arms 90, 92 and syringe retaining member 106 corresponds generally to the fully rotated "open" position of the circular members 118, 120 shown in FIGS. 10 and 11. Once the support arms 90, 92 and the syringe retaining member 106 are in the intermediate position, they may be rotated or pivoted fully to the second position. The support members 90, 92 are moved to the second position by simply exerting downward pressure on the support arms 90, 92. The support arms 90, 92 and syringe retaining member 106 rotate about the circular members 118, 120 to move to the second position depending below the pressure jacket 32 and syringe 24, preferably sufficiently downward to permit the syringe 24 to be removed easily from the front loading pressure jacket 32. Thus, the actuation handle 126 is used primarily to "open" the camming circular members 118, 120 and move the support arms 90, 92 and syringe retaining member 106 to the intermediate position. Thereafter, the operator provides the motive forces to move the syringe support structure 36 out of the way for a syringe-removal operation.

The rotational movement of the circular members 118, 120 in the circular apertures 138, 140 is preferably limited. For this purpose, the circular members 118, 120 define respective slots 166, 168, which extend through the circular members 118, 120. The slots 166, 168 are generally arcuate shaped, and preferably define an arc of a circle. The sidewalls of the 154, 156 of the respective support brackets 122, 124 each define a pin receiving opening 170. A pair of pins 172, 174 extends through the pin receiving openings 170 in the respective brackets 122, 124 and the slots 166, 168 in the respective circular members 118, 120. The pins 172, 174 cooperating with the pin receiving openings 170 and slots 166, 168 limit the rotational movement of the circular members 118, 120 in the circular apertures 138, 140 to approximately a one-quarter turn (i.e., one-quarter rotation) in the circular apertures 138, 140. The slots 166, 168 prevent the circular members 118, 120 from being over-rotated by providing hard stops, which limit the rotational movement of the circular members 118, 120. Preferably, the hard stops correspond to the open and closed positions of the circular members 118, 120. Thus, one hard stop generally corresponds to the support arms 90, 92 and syringe receiving member 106 being in the first or syringe-engaged position and the circular members 118, 120 being in the closed position. The second hard stop is located at the end of the axial movement of the support arms 90, 92 (i.e., intermediate position). The slots 166, 168 generally operate as guide tracks that guide and limit the rotational movement of the "camming" circular members 118, 120.

The proximal ends 98, 100 of the support arms 90, 92 preferably define respective guide tracks 176, 178, which guide the movement of the support arms 90, 92 as they move distally or linearly away from the faceplate 18 under the influence of the circular members 118, 120. The guide tracks 176, 178 define the exact path for the support arms 90, 92 to follow in their movement from the first or syringe-engaged position to the intermediate position. The guide tracks 176, 178 also define and limit the movement of support arms 90, 92 when they are pivoted fully to the second or syringe-removal position. A pair of cross pins 180, 182 cooperates with the guide tracks 176, 178 respectively. The cross pins 180, 182 extend through the faceplate 18 to cooperate with the guide tracks 176, 178, respectively. The cross pins 180, 182 are preferably fixed to the faceplate 18.

The path defined by the guide tracks 176, 178 generally causes the support arms 90, 92 and syringe retaining member 106 to move distally or linearly away from the faceplate 18 and slightly vertically downward from the first position (FIG. 9) to the intermediate position (FIG. 10). To move the support arms 90, 92 and the syringe retaining member 106 fully to the second position, the operator of the fluid injection apparatus 10 exerts downward force on the support arms 90, 92. The cross pins 180, 182 and guide tracks 176, 178 act as a guiding and stopping mechanism to prevent the support arms 90, 92 from impinging downward onto the faceplate 18 in the vertical front openings 94, 96. As shown in FIG. 11, the cross pins 180, 182 seat in the upper ends of the guide tracks 176, 178 during the downward movement of the support members 90, 92, which restricts the downward movement of the support arms 90, 92 to a specific distance.

Preferably, the support arms 90, 92 further define detent openings or recesses 184, 186, respectively, located generally below and offset from the guide tracks 176, 178. The detent openings 184, 186 cooperate with a pair of ball detents 188, 190 attached to the faceplate 18. The ball detents 188, 190 are generally located below the cross pins 180, 182 and are secured to the faceplate 18. The ball detents 188, 190 mate with the detent openings or recesses 184, 186 when the support arms 90, 92 and syringe retaining member 106 are moved to the intermediate position. The mating connection between the ball detents 188, 190 and detent openings 184, 186 operates to hold the support arms 90, 92 in the intermediate position prior to exerting downward force on the support arms 90, 92 to move the support arms 90, 92 fully to the second position. The ball detents 188, 190 also provide a tactile and preferably audible indication that the support arms 90, 92 are correctly set in the intermediate position and the circular members 118, 120 are set in the open position.

The mating connection between the ball detents 188, 190 and detent openings 184, 186 allows one-handed operation of the fluid injection apparatus 10. For example, during a syringe loading operation, once the syringe 24 is loaded in the pressure jacket 32, the support arms 90, 92 may be rotated upward with one hand until the ball detents 188, 190 mate with the detent openings 184, 186, which will support the support arms 90, 92 until the circular members 118, 120 are rotated to the closed position by the actuation handle 126 and the support arms 90, 92 and syringe retaining member 106 are moved distally back to the first or syringe-engaged position.

The circular members 118, 120 define respective ball detent receiving openings 192, 194 having a second ball detent 196 located therein. The ball detents 196 cooperate with ball detent openings or recesses 198 defined in the sidewalls 154, 156 of the brackets 122, 124 when the circular members 118, 120 are in the closed position (FIG. 9). The mating connection between the ball detents 196 and detent openings 198 provides a tactile and preferably audible indication that the circular members 118, 120 are in the closed position and, further, that the support arms 90, 92 and syringe receiving member 106 are set in the first or syringe-engaged position. These tactile and auditory cues enable the operator of the fluid injection apparatus 10 to recognize when the support members 90, 92 and syringe retaining member 106 are in the correct position to begin a fluid injection procedure.

Referring to FIGS. 12-20, a second embodiment of the fluid injection apparatus 10' and the pressure jacket assembly 30' of the present invention are shown. In FIGS. 12-20, the injector head 12' and injector housing 14' are omitted to simplify explanation of the fluid injection apparatus 10', but these elements should be considered to be part of the fluid injection apparatus 10'. The coupling member 34' and faceplate 18' of the pressure jacket assembly 30' cooperate in the same manner as the coupling member 34 and faceplate 18 discussed previously. The faceplate 18' is substantially identical to the faceplate 18 discussed previously, with the exception that the support arms 90', 92' are now pivotally connected directly to the faceplate 18', rather than interconnected in the injector housing 14' and supported on the internal facing side 114' of the faceplate 18'. For this purpose, the circular apertures 138', 140' in the proximal ends 98', 100' of the support arms 90', 92' are made smaller and aligned with side openings 200, 202 defined in the sides of the faceplate 18', respectively. The proximal ends 98', 100' of the support arms 90', 92' are pivotally connected to the faceplate 18' by pivotal connections 203 (i.e., mechanical fasteners, such as bolts and the like). The pivotal connections 203 between the proximal ends 98', 100' of the support arms 90', 92' and the faceplate 18' allow the support arms 90', 92' to move between the first and second positions described previously. However, the movement exhibited by the support arms 90', 92' between the first and second positions in the fluid injection apparatus 10' is now substantially pivotal or rotational motion rather than the translational and rotational movement described previously.

The pressure jacket 32' and coupling member 34' cooperate in the same manner as described previously in connection with the first fluid injection apparatus 10. However, the pressure jacket 32' is slightly modified in comparison with the pressure jacket 32 discussed previously. The distal end 42' of the pressure jacket 32' now defines a beveled portion 204. The beveled portion 204 generally comprises approximately half of the circumference of the distal end 42' of the pressure jacket 32'. As shown, for example, in FIG. 15, the beveled portion 204 defines an acute angle θ with a central axis L of the pressure jacket 32' and the syringe 24 when loaded therein. The beveled portion 204 preferably defines an acute angle of between about 5° and 60° with the central axis L of the pressure jacket 32'. It is preferred that the beveled portion 204 defines an angle θ less than about 60°. In general, the beveled portion 204 allows the syringe retaining member 106' to pivot or rotate between a syringe-retaining position wherein the syringe retaining member 106' prevents removal of the syringe 24 from the pressure jacket 32', and a pivoted position wherein an upper portion of the syringe retaining member 106' is spaced from the injection section 76 of the syringe 24, which allows the support arms 90', 92' and the syringe retaining member 106' to be rotated downward to the second or syringe-removal position, as discussed previously. The beveled portion 204 generally provides the axial distance necessary for the syringe retaining member 106' to disengage from the injection section 76 of the syringe 24 and clear the distal end 42' of the pressure jacket 32' when the support arms 90', 92' and syringe retaining member 106' are to be rotated downward from the pressure jacket 32.

The threaded connection between the externally threaded portion 46' at the proximal end 44' of the pressure jacket 32' and the internally threaded portion 52' of the coupling member 34' is preferably configured such that when the proximal end 44' is fully threaded into the internally threaded portion 52', the beveled portion 204 forms the lower part of the pressure jacket 32' (i.e., lies below a horizontal plane generally bisecting the cylindrical shaped pressure jacket 32' when the pressure jacket 32' is mounted to the faceplate 18'). The pressure jacket 32' is configured to receive the syringe 24 in the same front-loading manner as the pressure jacket 32 discussed previously.

The syringe retaining member 106' differs from the syringe retaining member 106 discussed previously in that the syringe retaining member 106' is pivotally connected by pivotal connections 205 (i.e., mechanical fasteners and the like) to the distal ends 102', 104' of the support arms 90', 92'. The pivotal connections 205 permit the upper portion of the syringe retaining member 106' to pivot away from the injection section 76 of the syringe body 70, and the lower portion to pivot toward the beveled portion 204. As indicated previously, this pivotal movement generally enables the syringe retaining member 106' to disengage from the injection section 76 of the syringe body 70 (i.e., syringe-retaining position). The beveled portion 204 correspondingly provides the necessary clearance for the syringe retaining member 106' to pass over the distal end 42' of the pressure jacket 32' when the support arms 90', 92' and syringe retaining member 106' are to be moved from the first to the second positions and vice versa.

Figure 13:
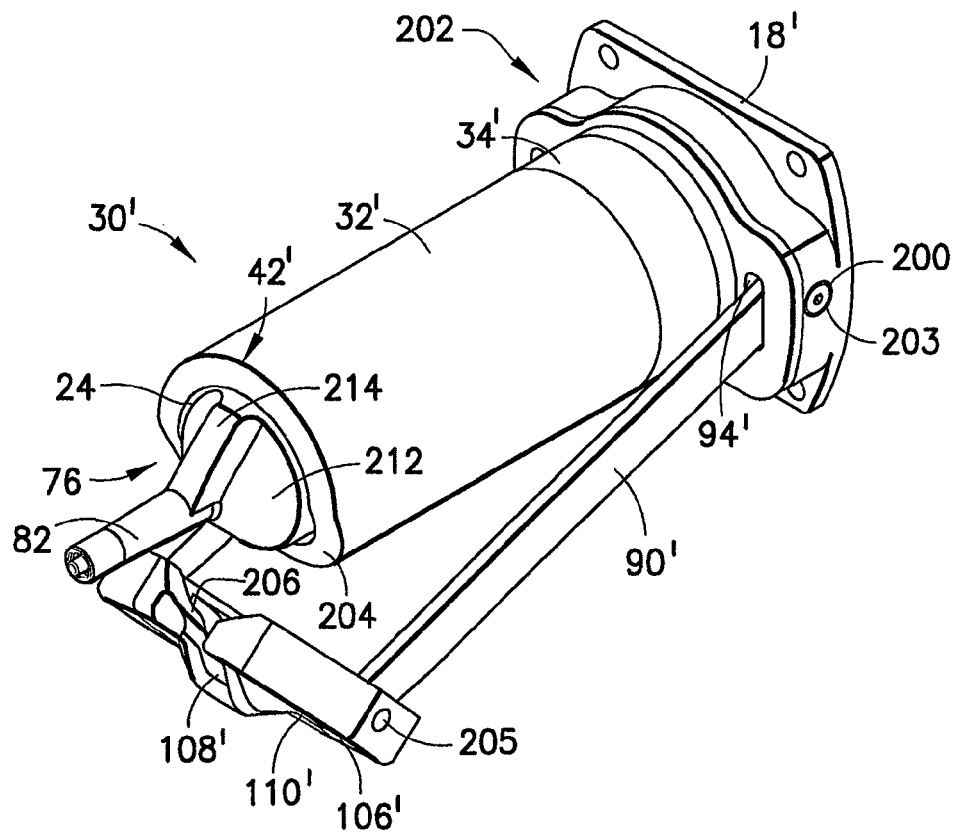
FIG. 13 is a perspective view of the pressure jacket assembly of FIG. 12 showing the syringe support structure in the syringe-disengaged position.
Figures 19, 20:
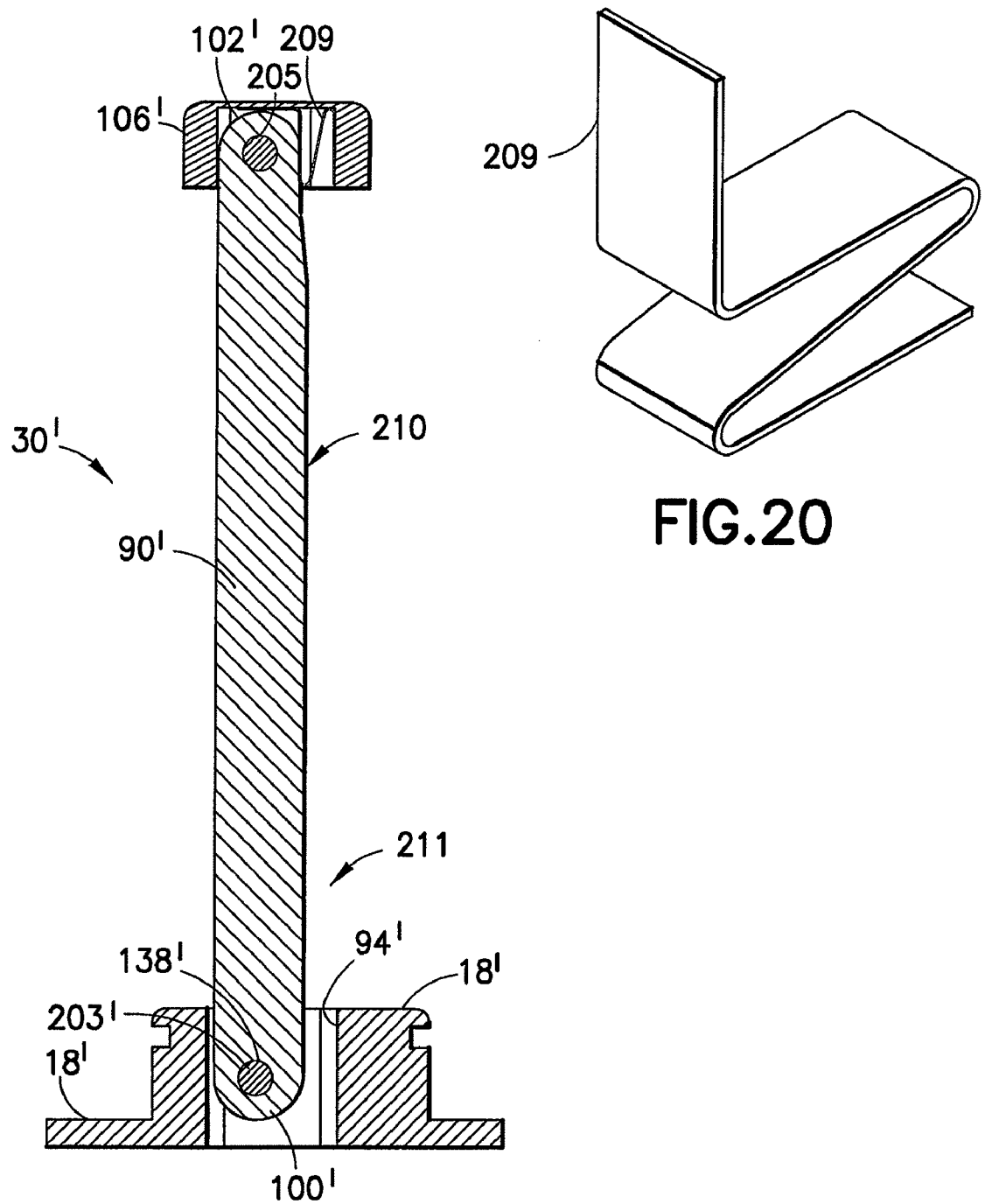
FIG. 19 is a cross sectional view taken along line 19-19 in FIG. 18.
FIG. 20 is a perspective view of a spring device used in the syringe support structure of the pressure jacket assembly of FIG. 12.

As shown, for example, in FIGS. 13 and 19, the syringe retaining member 106' has a syringe facing side 206 that is generally formed to cooperate with the conical shape of the injection section 76 of the syringe body 70. The syringe facing side 206 of the syringe retaining member 106' defines respective cavities 207, 208 adjacent the distal ends 102', 104' of the support arms 90', 92'. The cavities 207, 208 house respective springs 209 (i.e., spring means), such as leaf springs. The springs 209 are positioned to act between the distal ends 102', 104' of the support arms 90', 92' and the syringe retaining member 106'. In particular, the springs 209 are adapted to bias the syringe retaining member 106' to a position oriented substantially perpendicular to the longitudinal axes of the support arms 102', 104'. For example, when the syringe retaining member 106' is pivoted toward the beveled portion 204 (i.e., pivoted position), the springs 209 provide a counter-acting force that acts to bias the syringe retaining member 106' back to a substantially 90° position with respect to the support arms 90', 92'. The springs 209 may be replaced by any equivalent spring device, such as a compression coil spring and the like.

In summary, the spring-biased syringe retaining member 106' is movable between a first or syringe-retaining position wherein the syringe retaining member 106' cooperates with the injection section 76 and prevents removal of the syringe 24 from the pressure jacket 32', and a second, pivoted position wherein the syringe facing side 206 of the syringe retaining member 106' disengages from the injection section 76 of the syringe 24 thereby permitting the syringe retaining member 106' and support arms 90', 92' to be moved to the second or syringe-removal position to allow removal of the syringe 24 from the pressure jacket 32'.

The support arms 90', 92' are preferably formed to create a moment that will maintain the support arms 90', 92' and syringe retaining member 106' in the first or syringe-engaged position. In the first position, the support arms 90', 92' are oriented substantially parallel to the syringe 24. As shown, for example, in FIG. 15, the support arm 90' reduces in cross section at the distal end 102' of the support arm 90' and increases in cross section at the proximal end 98'. In particular, a portion 210 of the support arm 90' proximate to the distal end 102' of support arm 90' has a reduced cross sectional area and, hence, has a reduced mass, and a portion 211 of the support arm 90' proximate to the distal end 102' of the support arm 90' has an increased cross sectional area and has increased mass. The mass differences between the distal end 102' and proximal end 98' of the support arm 90' creates a moment about the pivotal connection 203 with the faceplate 18'. The other support arm 92' has a similar reduced cross sectional portion 210 at its distal end 104'. The moments created by the support arms 90', 92' maintain the support arms 90', 92' oriented substantially parallel to the pressure jacket 32' and syringe 24, which maintains the syringe retaining member 106' in the syringe retaining position generally in engagement with the syringe 24.

Additional features of the syringe 24 associated with the fluid injection apparatuses 10, 10' will now be discussed with reference to FIGS. 2-4, 21 and 22. As stated previously, the syringe 24 may be a single-use syringe or a multi-patient use syringe. The injection section 76 of the syringe body 70 generally tapers inward toward a central axis L of the syringe body 70. The injection section 76 includes a conical portion 212 tapering from the cylindrical shaped center section or main body 80 to the injection neck 82. The conical portion 212 defines an alignment flange or tab member 214. This alignment flange or tab member 214, in a preferred embodiment, defines a hollow space or area therein. The alignment flange or tab member 214 is provided as a means to view the fluid within the syringe 24. Additionally, the alignment flange or tab member 214 acts as a visual indicator for properly aligning the syringe 24 in the pressure jacket(s) 32, 32'. Further, the alignment flange or tab member 214 provides a convenient handle for manipulating the syringe 24 and inserting it into the pressure jacket(s) 32, 32'. Secondarily, the hollow space defined by the alignment flange 214 may operate as an air bubble trap. Preferably, the alignment flange or tab member 214 generally extends the distance between the center section 80 of the syringe body 70 and the injection neck 82. A fluid dot, such as a glow-in-the-dark fluid dot 215 may be formed in the conical portion 212 as an optical aid.

The syringe plunger 216 is configured for connection to the injector drive piston 22. As mentioned previously, the injector drive piston 22 is extendable through the central passage 21 in the faceplate 18 for imparting motive forces to a syringe plunger disposed within the syringe 24. Accordingly, the injector drive piston 22 is preferably motorized. The injector drive piston 22 includes a rectangular injector end plate 218, which is adapted to capture the syringe plunger 216 and impart motion to the syringe plunger 216. The end plate 218 may include an integral, axially located light source 219 to illuminate the fluid loaded into the syringe 24. The syringe plunger 216 is generally conical-shaped to cooperate with the conical portion 212 of the injection section 76 of the syringe body 70. The syringe plunger 216 includes a base member 220 that is substantially enclosed by a cover 222, which forms the conical shape of the syringe plunger 216 and may be made of rubber, for example. The syringe plunger 216 includes a coupling end 224 that faces the proximal end 74 of the syringe body 70. The syringe plunger 216 may be transparent to allow light from the lighted injector end plate 218 to pass therethrough. In a preferred embodiment, a pair of flexible lug or coupling members 226 extend outward from the coupling end 224 for engaging the injector drive piston 22 and, more particularly, the injector end plate 218 attached to the injector drive piston 22, as described in U.S. Pat. Nos. 5,873,861 and 5,947,935, the disclosures of which are incorporated herein by reference. The coupling members 226 are flexible and may be integrally formed with the base member 220. In an alternative embodiment, the coupling members may be substantially fixed or rigid, as described in U.S. Pat. No. 4,677,980, which was previously incorporated by reference into this disclosure. The coupling members 226 each have an engagement arm 228. The coupling members 226 define a slot 230 therebetween. The slot 230 is configured to receive the injector end plate 218 attached to the injector drive piston 22. The alignment flange or tab member 214 provides a last resort air containment feature when the distal end (i.e., cover 222) extends into and "bottoms-out" in the conical portion 212. Any unnoticed air bubbles will tend to collect in the hollow area defined by the alignment flange or tab member 214 during operation of the injector head 12.

To facilitate aligning the slot 230 with the rectangular injector end plate 218 of the injector drive piston 22, the slot 230 is preferably aligned with the alignment flange or tab member 214, so that the alignment flange or tab member 214 provides a visual indication of the orientation of the slot 230. Thus, the operator of the fluid injection apparatus(es) 10, 10' will have a visual indication of the location of the slot 230 while inserting the syringe 24 into the pressure jacket(s) 32, 32' and attempting to place the syringe plunger 216 in engagement with the injector drive piston 22. The alignment flange 214 automatically orients the coupling members 226 in a desired mounting position aligned with the rectangular injector end plate 218 when the syringe 24 is inserted into the pressure jacket(s) 32, 32'. The alignment flange 214 preferably extends sufficiently outward from the conical portion 212 to be grasped by the operator of the fluid injection apparatus(es) 10, 10' and used as a handle for manipulating the syringe 24, particularly during loading the syringe 24 into the pressure jacket(s) 32, 32'. The alignment flange 214 and syringe plunger 216 are preferably oriented so that the alignment flange 214 is oriented substantially vertically when the syringe 24 is loaded into the pressure jacket(s) 32, 32'. Thus, in this "loaded position", the slot 230 is also vertically oriented to engage the injector end plate 218. Additionally, in the preferred loaded position of the syringe 24, the air viewing feature of the alignment flange 214 is maximized.

To load the syringe 24 in the pressure jacket assembly 30 as shown in FIGS. 1-11, the following procedure is generally followed. The support arms 90, 92 and syringe retaining member 106 are located in the second or syringe removal position depending downward from the pressure jacket 32.

The distal end 42 of the pressure jacket 32 is thereby exposed permitting the syringe 24 to be inserted into the syringe receiving opening 45. The syringe 24 is front loaded into the pressure jacket 32 with the alignment flange 214 substantially aligned to vertical. This aligns the coupling members 226 of the syringe plunger 216 in the desired mounting position in which the slot 230 is aligned vertically with the rectangular injector end plate 218 attached to the injector drive piston 22. Once the syringe 24 is properly seated in the pressure jacket 32, the operator rotates the support arms 90, 92 (and syringe retaining member 106) upward to the intermediate position. The operator then rotates the actuation handle 126 counter-clockwise, for example, to move the support arms 90, 92 (and syringe retaining member 106) proximally toward the faceplate 18 and back to the first syringe-engaged position, wherein the syringe retaining member 106 engages the conical portion 212 of the syringe 24. The injection neck 82 of the syringe body 70 is received in the syringe receiving slot 108 defined in the retaining member 106. The alignment flange 214 is preferably aligned with the syringe receiving slot 108, which aligns the coupling members 226 to engage the injector end plate 218. The syringe 24 may then be placed in fluid communication with the fluid that is to be injected into the patient. Once the syringe 24 is filled with the desired fluid, the operator may view the fluid in the injection section 76 of the syringe body 70 through the openings 110 in the retaining member 106 and through the syringe receiving slot 108 to ensure that air is not present in the syringe 24.

Once the fluid injection apparatus 10 is placed in fluid communication with the body of a patient, the operator may actuate the injector drive piston 22. As the injector drive piston 22 moves forward through the central passage 21 in the faceplate 18, the injector end plate 218 contacts the engagement arms 228 of the coupling members 226. As the injector drive piston 22 continues to move forward, the injector end plate 218 urges the flexible coupling members apart until the injector end plate 218 is seated in the vertical slot 230 between the coupling members 226. The injector drive piston 22 may then apply motive forces to the syringe plunger 216 to inject the fluid into the patient. The engagement arms 228 secure the engagement between the injector drive piston 22 and the syringe plunger 216 during the procedure and permit the plunger 216 to be withdrawn (i.e., moved proximally at the end of the procedure, if necessary). The fluid in the syringe 24 may be illuminated by the light source integrated into the injector end plate 218.

Once the fluid injection procedure is complete, the operator of the fluid injection apparatus 10 rotates the actuation handle 126 clockwise, which moves the support arms 90, 92 and syringe retaining member 106 to the intermediate position. In the intermediate position, the syringe retaining member 106 is partially disengaged from the conical portion 212 of the syringe 24. The operator then applies downward force on the support arms 90, 92 to move the support arms 90, 92 and syringe retaining member 106 to a position depending below the pressure jacket 32 and syringe 24 (i.e., second or syringe-removal position). The syringe 24 may then be removed from the pressure jacket 32, once the injector end plate 218 is disengaged from the syringe plunger 216.

The fluid injection apparatus 10' operates in a substantially analogous manner to the fluid injection apparatus 10 discussed hereinabove. The operation of the fluid injection application 10' differs from the fluid injection apparatus 10 in that the syringe retaining member 106' pivots with respect to the support arms 90', 92' and the support arms 90', 92' pivot with respect to the injector housing 14 and faceplate 18 without moving axially toward or away from the injector housing 14 and faceplate 18. The general operation of the fluid injection apparatus 10' will be discussed with reference to FIGS. 12-20.

With the support arms 90', 92' in the first position and the syringe retaining member 106' in the syringe-retaining position, the syringe retaining member 106' supports the injection neck 82 and prevents removal of the syringe 24 from the pressure jacket 32'. The springs 209 maintain the syringe retaining member 106' in the syringe-retaining position oriented substantially perpendicular to the support arms 90', 92'. During an injection procedure, the syringe 24 will generally move distally forward, contact, and exert force on the syringe facing side 206 of the syringe retaining member 106'. The syringe facing side 206 is generally formed to cooperate with the conical portion 212 of the syringe 24. The moments provided by the non-continuous cross section support arms 90', 92' are generally sufficient to maintain the support arms 90', 92' and the syringe retaining member 106' in the first or syringe-engaged position and prevent the syringe retaining member 106' from pivoting with respect to the support arms 90', 92' about the pivotal connections 205.

After an injection procedure is completed, the syringe 24 may be removed from the pressure jacket 32'. This is accomplished by the operator of the fluid injection apparatus 10' grasping the syringe retaining member 106' and pivoting the syringe retaining member 106' from the syringe retaining position to the pivoted position, as shown for example in FIG. 13. The syringe retaining member 106' rotates about the pivotal connections 205 so that the upper portion of the syringe facing side 206 of the syringe retaining member 106' disengages from the injection section 76 of the syringe body 70 and the lower portion of the syringe facing side 206 rotates or pivots toward the beveled portion 204 of the pressure jacket 32'. With the syringe retaining member 106' now disengaged substantially from the syringe 24, the syringe retaining member 106' and support arms 90', 92' may be rotated to a position depending downward from the pressure jacket 32' by the operator (i.e. second or syringe-removal position). In this movement, the support arms 90', 92' pivot about the pivotal connections 203 connecting the proximal ends 98', 100' of the support arms 90', 92' to the faceplate 18'. The beveled portion 204 provides the necessary clearance for the syringe retaining member 106' to clear the distal end 42' of the pressure jacket 32'. The used syringe 24 may be removed and replaced with a new syringe 24 for the next injection process. The foregoing process may be reversed to return the syringe retaining member 106' and the support arms 90', 92' to the correct position for another procedure. The support members 90', 92' will automatically orient to the first or syringe-engaged position by the moments created by the non-continuous cross sectional portions 210, 211 of the support arms 90', 92', as discussed previously, which will place the syringe retaining member 106' in the correct position to cooperate with the conical portion 212 of the syringe 24. The springs 209 will automatically orient the syringe retaining member 106' with respect to the support arms 90', 92' and syringe 24 when the support arms 90', 92' are returned to the first or syringe-engaged position.

FIGS. 5-8 show additional features of the fluid injection apparatuses 10, 10' of the present invention. The following discussion is made with reference to the first embodiment of the fluid injection apparatus 10, but is equally applicable to the second embodiment of the fluid injection apparatus 10' and (pressure jacket assembly 30') discussed previously. During the fluid injection procedure, it is especially advantageous for the operator of the fluid injection apparatus 10 to view the fluid contents of the syringe 24. Of particular importance is the ability of the operator to view the fluid within the syringe 24. Accordingly, the present fluid injection apparatus 10 includes an illumination feature for illuminating the syringe 24 during a fluid injection procedure.

Figure 5:
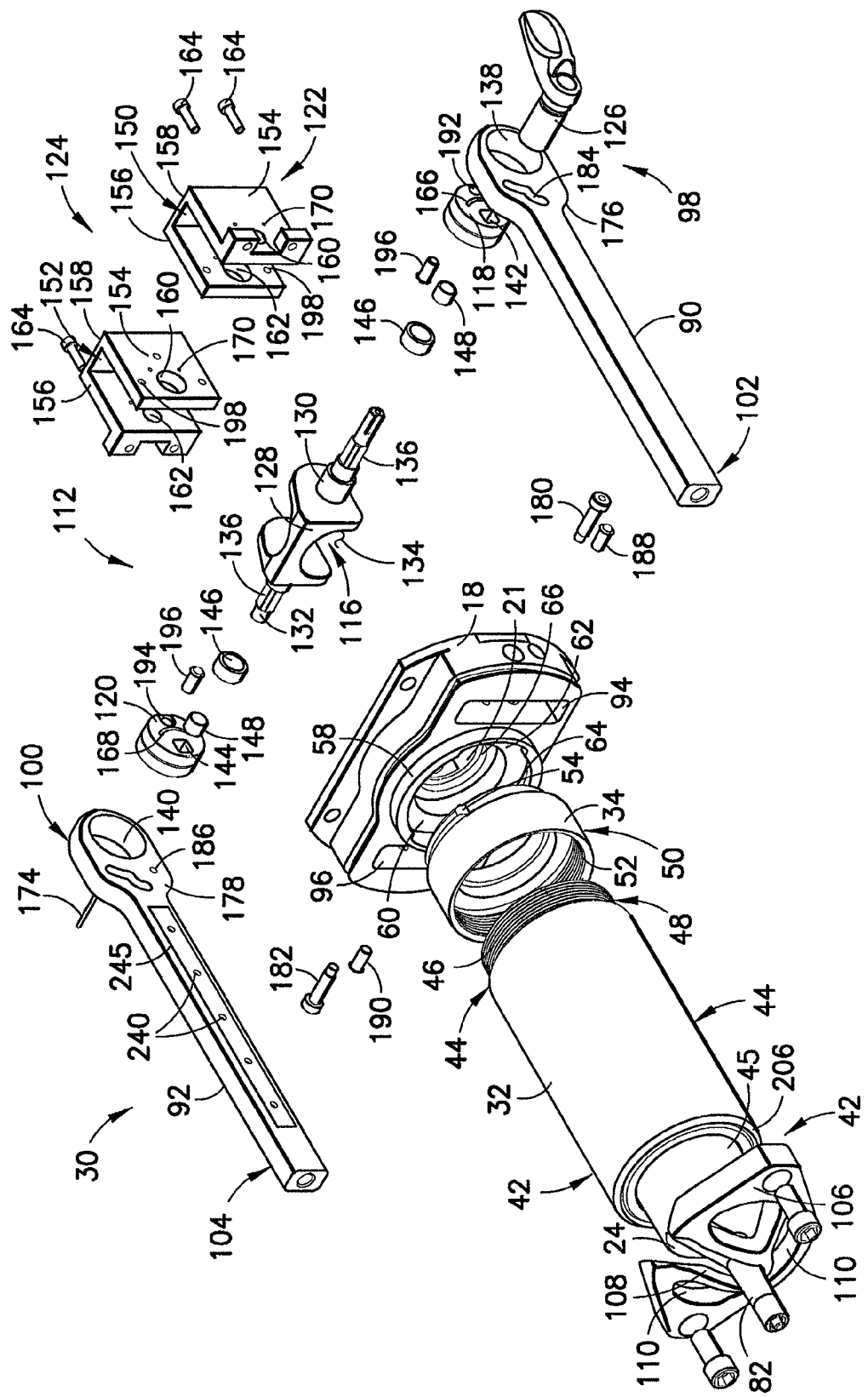
FIG. 5 is an exploded perspective view of the pressure jacket assembly of the fluid injection apparatus of FIG. 1.
Figure 6:
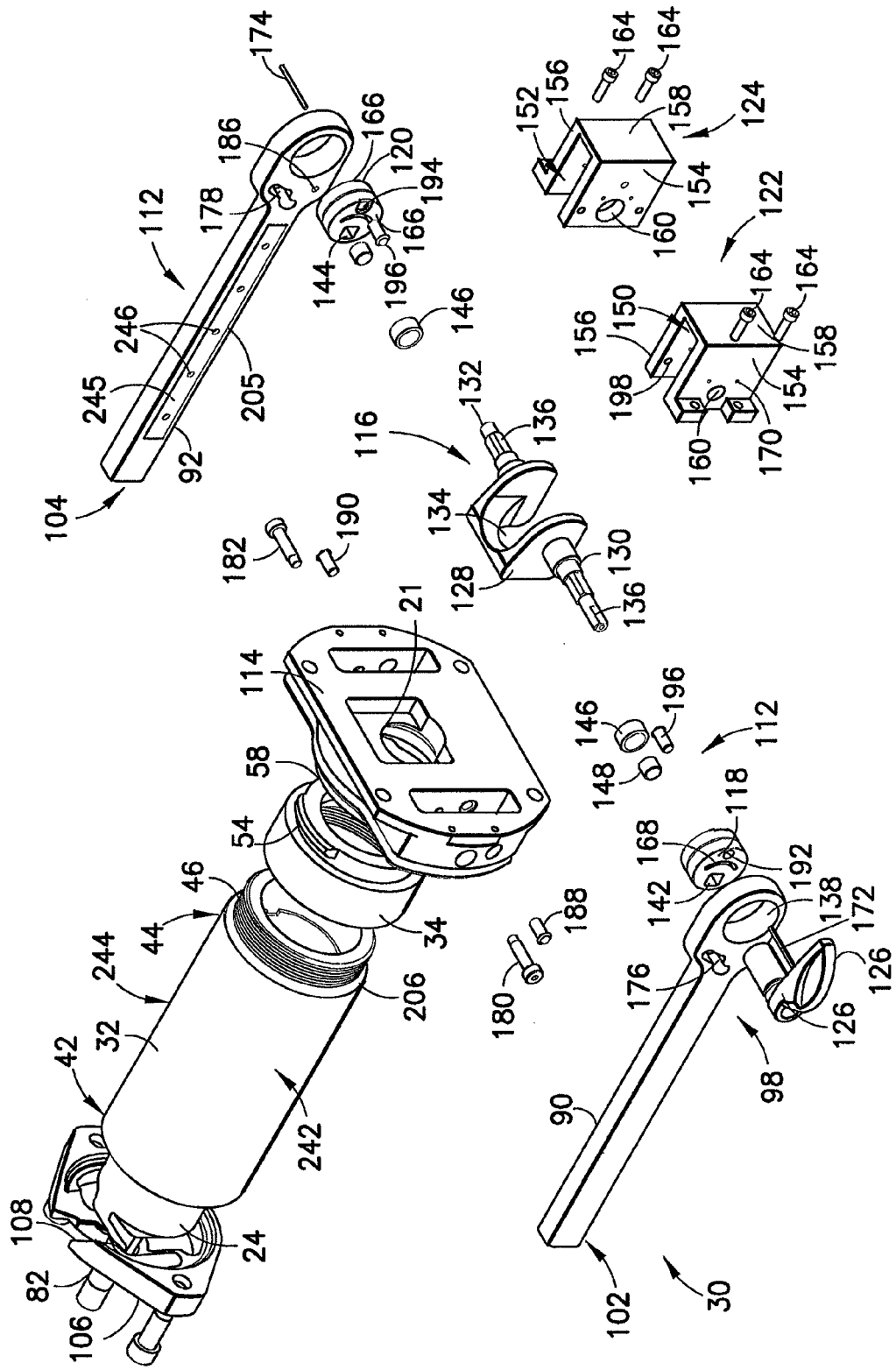
FIG. 6 is an exploded perspective view of the pressure jacket assembly of FIG. 5 viewed from an opposite end.
Figure 7:
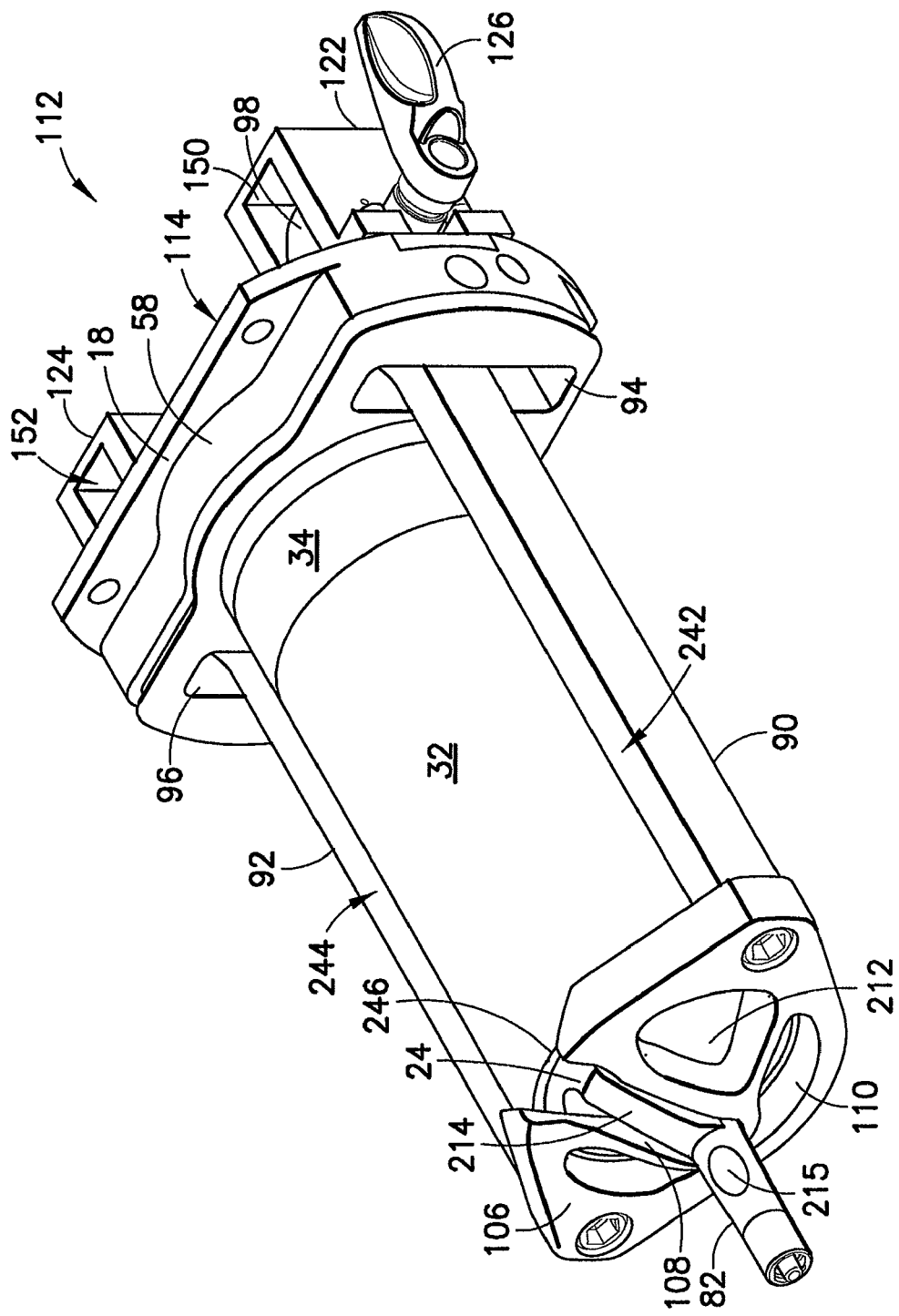
FIG. 7 is a perspective view of the pressure jacket assembly of FIGS. 5 and 6 showing a syringe support structure of the pressure jacket assembly in a syringe-engaged position supporting a syringe.
Figure 8:
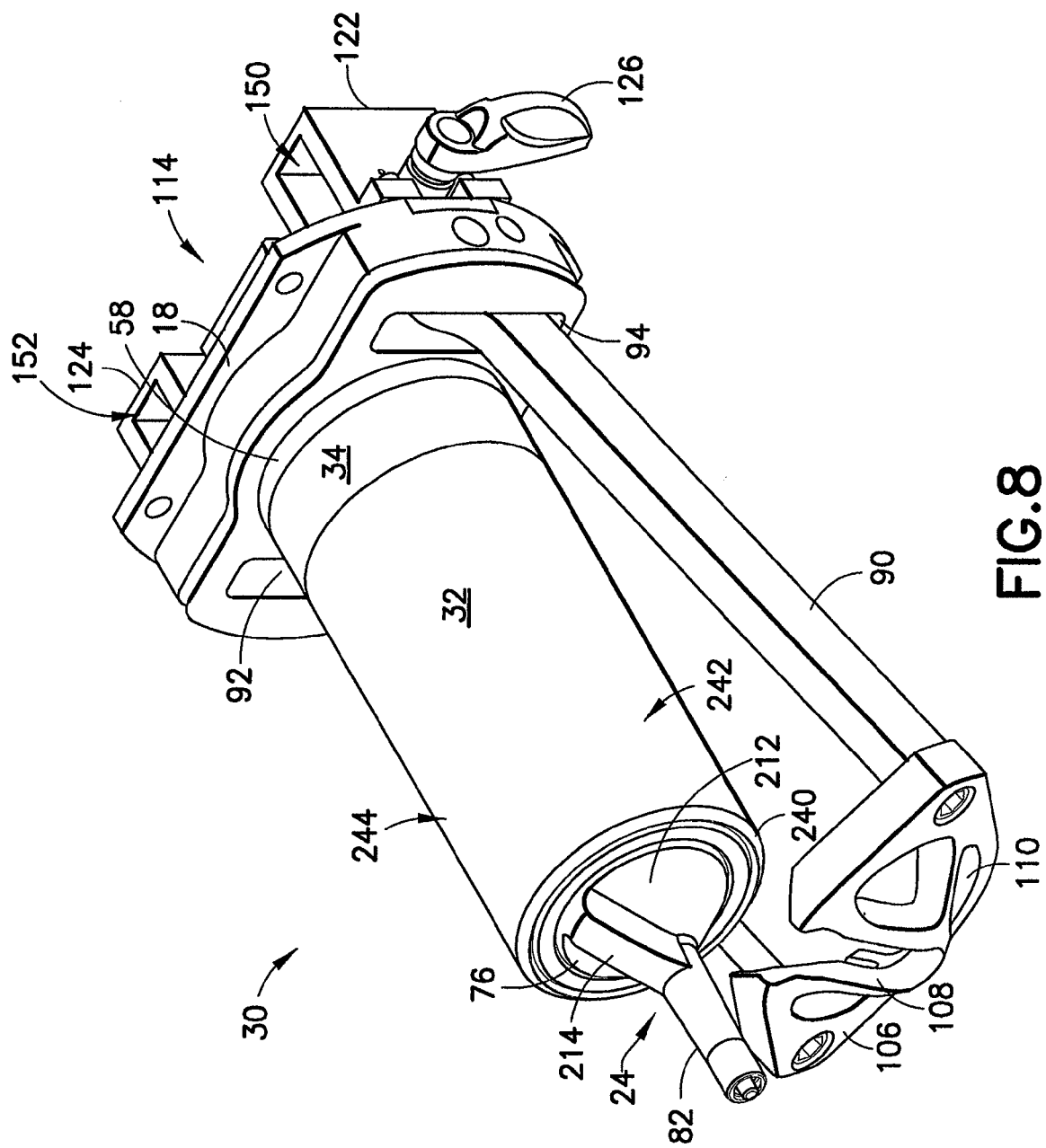
FIG. 8 is a perspective view of the pressure jacket assembly of FIGS. 5 and 6 showing the syringe support structure of the pressure jacket assembly in a syringe-disengaged position.

As shown in FIGS. 5-8, the pressure jacket assembly 30 further includes at least one light source 240 attached to one or both of the support arms 90, 92 and facing the pressure jacket 32. Preferably, the support arms 90, 92 each include a plurality of light sources 240. The light sources 240 (hereinafter collectively referred to as "light source 240") are shown in FIGS. 5 and 6 as a plurality of light emitting diodes (LED's). The support arms 90, 92 in the first (i.e., syringe-engaged position) preferably extend laterally along lateral sides 242, 244 of the pressure jacket 32 and preferably substantially parallel to the central axis L of the syringe 24, which is also substantially the central axis of the pressure jacket 32. It has been found by the inventors that illumination along the central axis L of the syringe 24 and, hence, the pressure jacket 32 provides the best diffusion of light in the syringe body 70. Accordingly, the pressure jacket 32 is preferably made of a substantially clear plastic material to allow light to penetrate into the syringe body 70. As stated, the light source 240 may be a plurality of light emitting diodes (LED's). However, any equivalent lighting source may be used to replace the light emitting diodes (LED's), such as a mini-fluorescent light bar 245, which is schematically illustrated in FIGS. 5 and 6. Another possible light source 240 is a fiber-optic bed. Additionally, the light source 240 may be located on the syringe retaining member 106, facing the conical portion 212 of the syringe 24. For example, the light source 240 may be attached to the syringe facing side 206' of the syringe retaining member 106' shown in FIGS. 12-20.

Referring to FIGS. 5-8 and 23-26, to enter the fluid in the syringe 24, light from the light source 240 must pass through a wall 246 of the pressure jacket 32 and a body wall 248 of the syringe body 70. A difficulty with illuminating cylindrical structures, such as the pressure jacket 32 and syringe body 70, with an externally located light source is that all areas of the cylindrical structure are not illuminated equally, particularly when the cylindrical structure is filled with fluid. To assure adequate diffusion of light in the syringe 24, the present invention includes one or more diffusion elements engaged with or incorporated into the pressure jacket 32, which is used to achieve proper light diffusion before light enters the syringe body 70. In alternative embodiments, the diffusion element(s) may be placed on or incorporated into the inner or outer walls of the pressure jacket 32, or embedded between the inner and outer walls. Several embodiments of the pressure jacket 32 are discussed hereinafter with particular reference to FIGS. 23-26. The embodiments are separately designated with lower case letters "a", "b", and "c".

Figure 24:
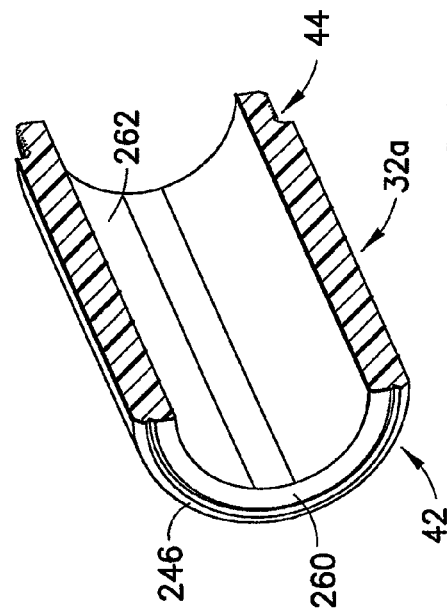
FIG. 24 is a cross sectional view taken along line 24-24 in FIG. 23.

FIG. 24 is a longitudinal cross sectional view of a first light-diffusing pressure jacket made in accordance with the present invention and designated with reference character 32a. The pressure jacket 32a includes a lens 260 located on an inner surface 262 of the pressure jacket wall 246. The lens 260 may be affixed to the inner surface 262 of the pressure jacket wall 246 with an adhesive, or formed integrally with the pressure jacket wall 246. The lens 260 extends longitudinally along the inner surface 262 of the pressure jacket wall 246 and diffuses light entering the pressure jacket 32a from the light source 240. Preferably, the lens 260 extends substantially the distance between the distal end 42 and proximal end 44 of the pressure jacket 32a. However, in alternative embodiments, the lens 260 could be segmented or multiple lenses could be placed along the pressure jacket 32a. Additionally, the lens 260 is preferably located on the inner surface 262 directly opposite from the light source 240. Once passing through the lens 260, the light is diffused and enters the syringe body 70 to fully illuminate the fluid in the syringe body 70, without the presence of "dead" or shaded areas, or "hotspots" of increased glare.

Figure 25:
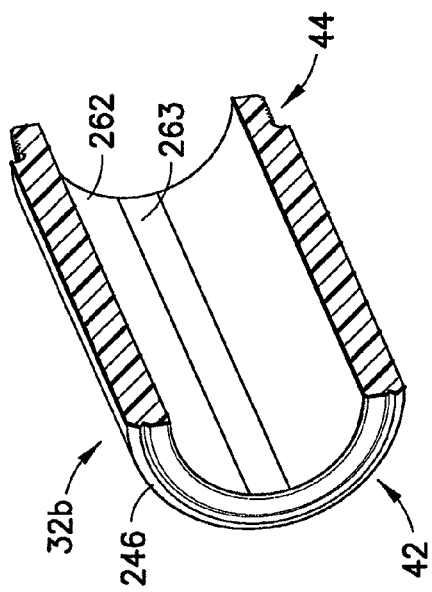
FIG. 25 is a cross sectional view taken along line 25-25 in FIG. 23.

A second embodiment of the pressure jacket is shown in FIG. 25 and is designated with reference character 32b. In this embodiment, the inner surface 262 of the pressure jacket wall 246 is roughened or etched to form a roughened or etched area 263. In particular, the inner surface 262 of the pressure jacket wall 246 is chemically or mechanically roughened such that the roughened area 263 is formed in the original clear surface finish. The degree or area of roughness may be made as wide as necessary to scatter or diffuse the light entering the syringe body 70 from the light source 240. The roughened area 263 may also be segmented and is preferably located substantially opposite from the light source 240.

Figure 26:
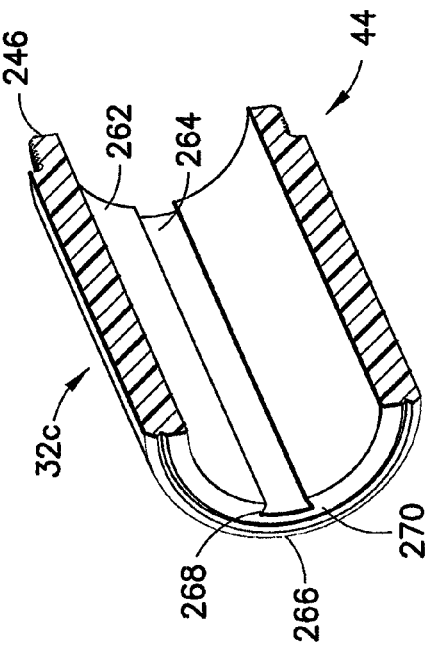
FIG. 26 is a cross sectional view taken along line 26-26 in FIG. 23.
Figure 23:
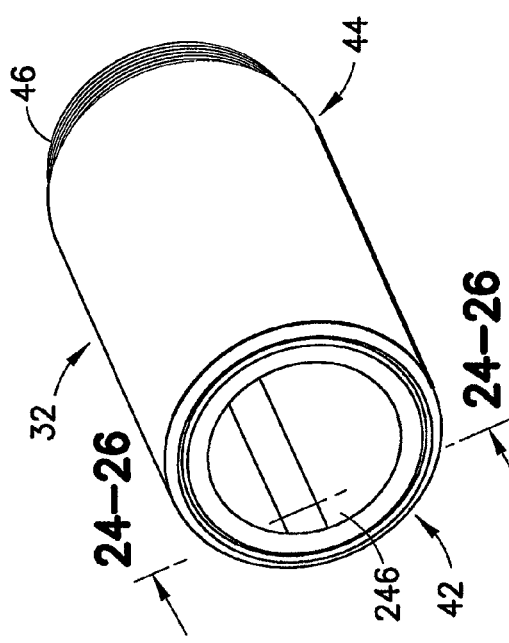
FIG. 23 is a perspective view of a pressure jacket associated with the pressure jacket assemblies of the present invention.

FIG. 26 shows a presently preferred embodiment of the pressure jacket, which is designated with reference character 32c. The pressure jacket 32c, according to this embodiment, includes a light-diffusing strip 264 applied to the inner surface 262 of the pressure jacket wall 246. The light-diffusing strip 264 may be affixed to the inner surface, for example, 262 with an adhesive. The light-diffusing strip 264 extends longitudinally along the inner surface 262 of the pressure jacket wall 246 and diffuses light entering the pressure jacket 32c from the light source 240. Preferably, the light-diffusing strip 264 extends substantially the distance between the distal end 42 and the proximal end 44 of the pressure jacket 32c. In alternative embodiments, however, the light-diffusing strip 264 may be segmented, or multiple strips could be placed along the pressure jacket. Additionally, the light-diffusing strip 264 is preferably located on the inner surface 262 directly opposite from the light source 240.

A preferred attachment scheme for the light-diffusing strip 264 locates the light-diffusing strip 264 in a groove 266 (or grooves if more than one strip 264 is used) extending longitudinally along the inner surface 262 of the pressure jacket wall 246. The groove 266 is preferably substantially trapezoidal shaped in cross section with two inward facing projections 268, 270 for retaining the light-diffusing strip 264 in the groove 266. Preferably, the light-diffusing strip 264 is a white polycarbonate material. The width of the groove 266 and light-diffusing strip 264 may be increased as necessary to fully diffuse the light entering the syringe body 70, as will be appreciated by those skilled in the art.

Figure 27:
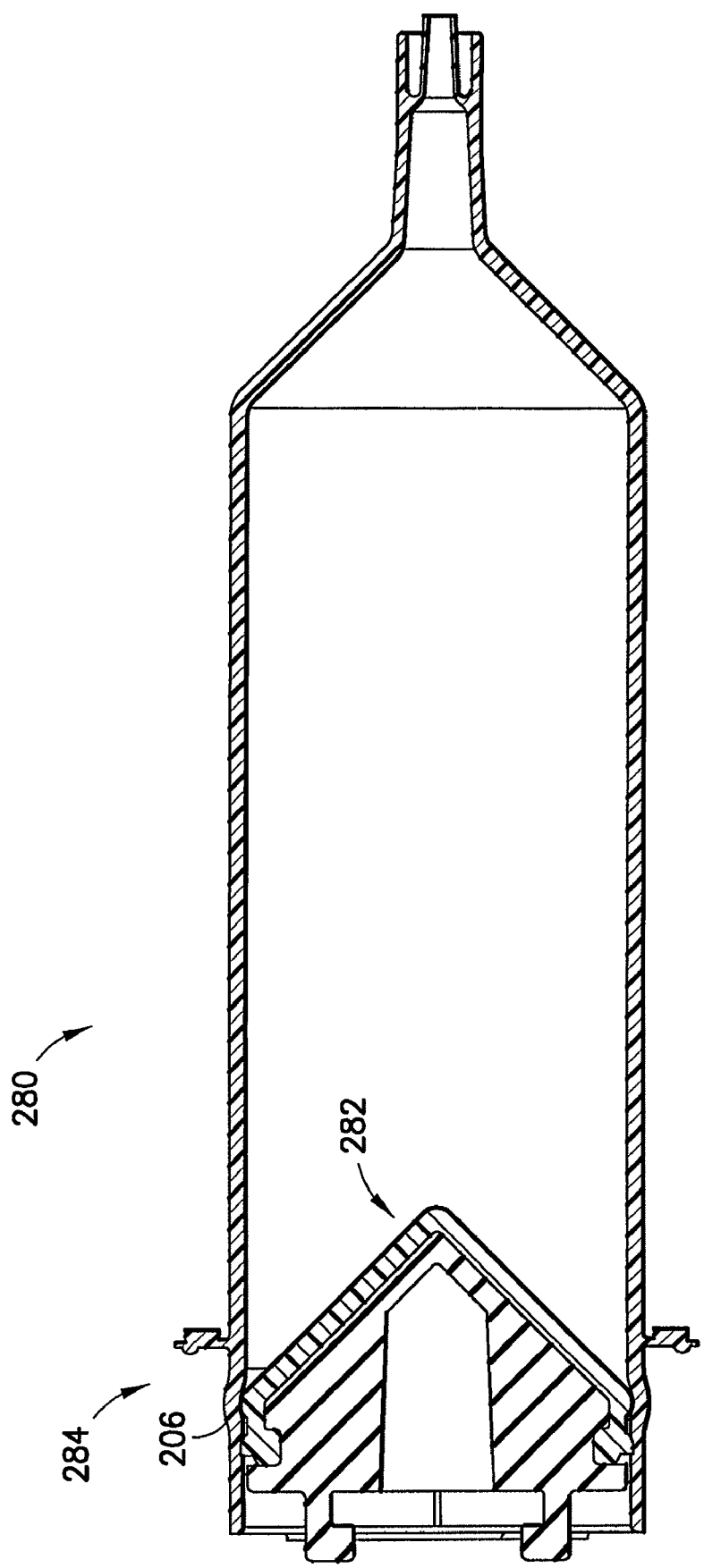
FIG. 27 is a plan cross sectional view taken along a longitudinal axis of a prior art syringe.

Referring to FIG. 27, as discussed previously, prior art syringes for medical injection procedures, such as syringe 280, are often stored with a pre-positioned syringe plunger 282. A difficulty with current disposable plastic syringes 280 is that these syringes 280 exhibit plastic creep over time and especially during sterilization heat cycles. This causes the plastic syringe 280 to swell, particularly in a plunger area 284 about the syringe plunger 282. This often makes it difficult to load prior art plastic syringes 280 in front loading pressure jackets, because of swelling 286 in the plunger area 284 wherein the syringe plunger 282 is stored.

Figure 21:
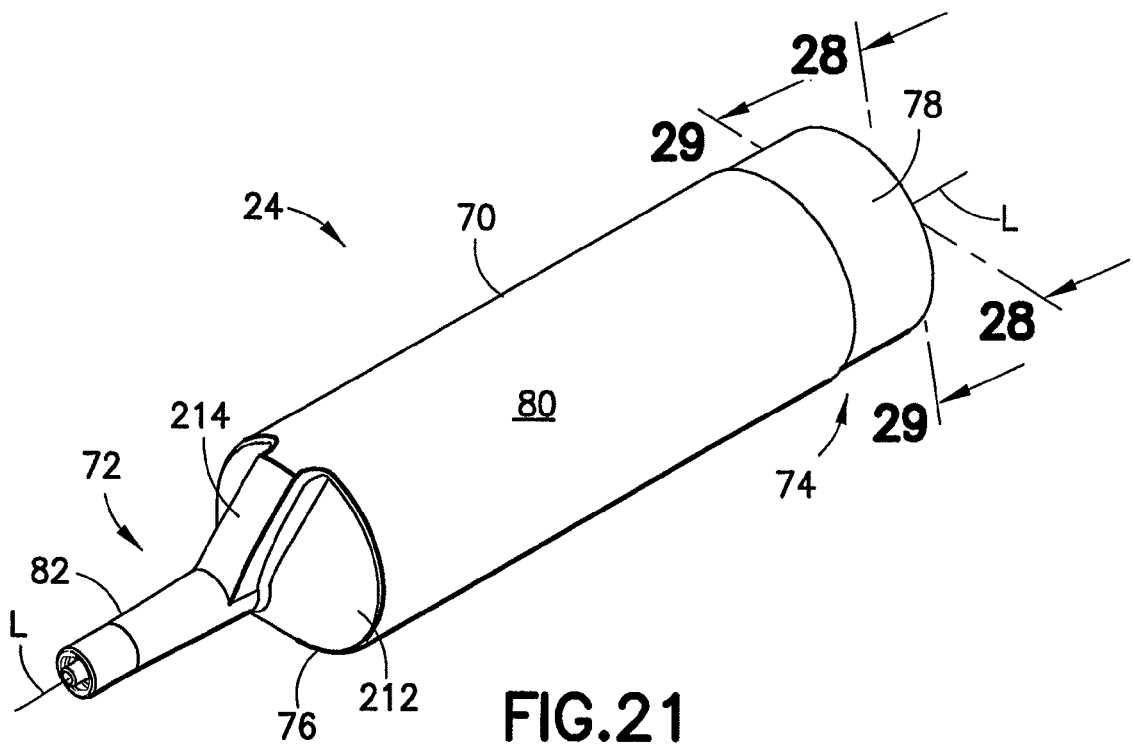
FIG. 21 is a perspective view of the syringe associated with the fluid injection apparatuses and pressure jacket assemblies of FIGS. 1 and 12.
Figure 22:
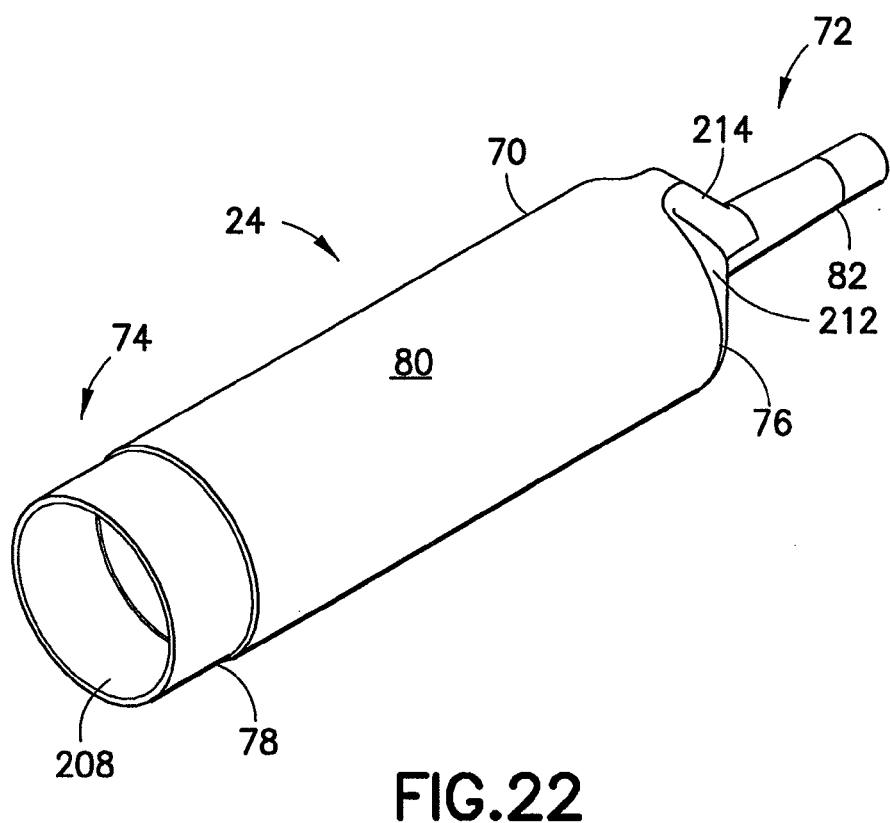
FIG. 22 is a perspective view of the syringe of FIG. 21 viewed from an opposite end.

As shown in FIGS. 3, 20, 21, 28, and 29 the syringe 24 of the present invention overcomes this disadvantage by storing the syringe plunger 216 in the expansion section 78. The expansion section 78 is preferably formed adjacent the cylindrical center section 80 of the syringe body 70 and at the proximal end of 74 of the syringe body 70. However, the expansion section 78 may be formed or located at any position in the syringe body 70 wherein the syringe plunger 216 is to be stored. At the expansion section 78, the wall 248 of the syringe body 70 narrows from a thickness t to a reduced wall thickness $t_r$. Thus, an inner diameter $ID_{es}$ of the expansion section 78 is larger than an inner diameter $ID_{CS}$ of the cylindrical center section or main body 80. The reduced wall thickness $t_r$ at the expansion section 78 allows the expansion section 78 to expand outward under the force exerted by the syringe plunger 216 without an outer diameter $OD_{es}$ of the expansion section 78 becoming larger than an outer diameter $OD_{es}$ of the center section 80 of the syringe body 70. As shown in FIGS. 20 and 21, both an outer surface 290 of the wall 248 of the syringe body 70 and an inner surface 292 of the wall 248 of the syringe body 70 taper or are stepped to form the reduced wall thickness $t_r$ at the expansion section 78. In particular, the outer surface 290 of the wall 248 of the syringe body 70 is tapered or stepped inward toward the central axis L of the syringe body 70 and the inner surface 292 of the wall 248 of the syringe body 70 tapers or is stepped outward away from the central axis L of the syringe body 70 to form the reduced wall thickness $t_r$. An alternative configuration to the foregoing is to only taper or step the inner surface 292 of the wall 248 of the syringe body 70 outward away from the central axis L of the syringe body 70. Another alternative is to only taper or step the outer surface 290.

The reduced wall thickness $t_r$ at the expansion section 78 of the syringe 24 accommodates the expansion and plastic creep of the plastic syringe body 70 even after long periods of storage. Even after long storage periods, the syringe 24 with pre-positioned syringe plunger 216 may be quickly and easily inserted into front-loading pressure jacket systems, such as the pressure jacket assemblies 30, 30' discussed previously. As stated previously, the syringe plunger 216 is stored in the expansion section 78. When the syringe 24 is inserted into the pressure jackets 32, 32' and ready for use, the syringe plunger 216 is engaged by the injector drive piston 22 in the manner discussed previously and moved forward from the expansion section 78 to the center section or main body 80 of the syringe 24, which may be referred to as the "working zone" of the syringe 24.

Referring to FIGS. 30 and 31 (and FIGS. 4-6), an alternative connection between the pressure jacket(s) 32, 32' and faceplate(s) 18, 18' is shown, as indicated previously. The alternative configuration illustrated in FIGS. 30 and 31 allows the pressure jacket(s) 32, 32' to move axially (i.e., distally and proximally) with respect to the faceplate(s) 18, 18'. At higher pressures, the syringe support structure(s) 36, 36' in the respective embodiments of the fluid injection apparatus(es) 10, 10' will move slightly distally forward due to stretching of the support arms 90, 92 and 90', 92'. This stretching occurs as the syringe 24 pushes forward on the syringe retaining member(s) 106, 106' in the syringe support structure(s) 36, 36'. Additionally, at higher pressures, the syringe 24 also swells and frictionally engages the internal wall in the pressure jacket(s) 32, 32'. The frictional engagement between the syringe 24 and, more particularly, the main body 80 of the syringe 24, and the internal wall of the pressure jacket(s) 32, 32' pulls the pressure jacket(s) 32, 32' forward with the syringe 24. If the pressure jacket(s) 32, 32' is not permitted to move forward an incremental amount, a stick-slip routine develops, wherein the syringe 24 is held back temporarily by frictional force until this is overcome. Thereafter, the syringe 24 slips forward and impacts against the syringe retaining member(s) 106, 106'.

The arrangement in FIGS. 30 and 31 attaches the pressure jacket(s) 32, 32' directly to the faceplate(s) 18, 18', as indicated previously. The pressure jackets(s) 32, 32' may be formed with the bayonet projections 54, 56, and 54', 56' at the proximal end(s) 44, 44' for cooperating with the opposing recesses 60, 62 and 60', 62' and the bayonet receiving slots 64, 66 and 64', 66' in the faceplate(s) 18, 18'. However, the bayonet receiving slots 64, 66 and 64', 66' are now preferably formed to allow the proximal end(s) 44, 44' of the pressure jackets 32, 32' to move axially a small distance in the slots 64, 66 and 64', 66', and avoid the stick-slip problem discussed previously. Only a small axial distance "A" is necessary to relieve the stick-slip problem. For example, this axial distance may be about 0.050 inches.

Referring to FIGS. 32-39, a third general embodiment of the fluid injection apparatus 10" and the pressure jacket assembly 30" of the present invention are shown. In FIGS. 32-39, the injector head 12" and injector housing 14" are omitted to simplify explanation of the fluid injection apparatus 10", but these elements should be considered to be part of the fluid injection apparatus 10". The fluid injection apparatus 10" and pressure jacket assembly 30" are substantially similar to the embodiments discussed previously, but differ in three general respects, namely: (1) the connection arrangement between the pressure jacket 32" and the injector head 12", (2) the addition of a syringe position sensor in the faceplate 18" (i.e., part of or separate and removable from the injector housing 14"), and (3) an alternative lighting arrangement for the at least one light source 240 and a corresponding alteration to the pressure jacket 32" to accommodate the alternative lighting arrangement. It is specifically noted that the fluid injection apparatus 10" shown in FIGS. 32-39 preferably incorporates the configuration of the support arms 90', 92' and syringe retaining member 106' discussed previously in connection with FIGS. 12-20. Thus, the support arms 90", 92" of the present embodiment interact with the faceplate 18" (and injector housing 14") in the manner discussed previously in connection with FIGS. 12-20 and the previous discussion relating to these elements is equally applicable to the fluid injection apparatus 10" and pressure jacket assembly 30", which are depicted in FIGS. 32-39. Further, the distal end 42" of the pressure jacket 32" is beveled in the same manner as the pressure jacket 32' discussed previously.

In the fluid injection apparatus 10" and pressure jacket assembly 30", the pressure jacket 32" is adapted to engage or connect directly to the faceplate 18", and therefore the injector housing 14" of the injector head 12" in a generally analogous manner to that shown in FIGS. 30-31 discussed previously. This engagement or connection arrangement between the pressure jacket 32" and the faceplate 18" is generally designated with reference numeral 300 in FIGS. 32-36. The connection 300 is secured by the engagement of an engagement tab 302 provided in the faceplate 18" with a corresponding engagement recess 304 formed in the proximal end 44" of the pressure jacket 32". As illustrated, in particular, in FIGS. 34-36, the proximal end 44" of the pressure jacket 32" is not externally threaded, but rather is adapted to engage directly with the faceplate 18". The proximal end 44" is formed with a generally elongated proximal portion 306 on one side thereof, which extends in the form of an arc extending along a portion of the circumference of the pressure jacket 32". The engagement recess 304 is formed in the elongated proximal portion 306 and may be in the form of a groove in the elongated proximal portion 306.

The engagement tab 302 may be spring-biased in the faceplate 18" to radially extend outward from the faceplate 18" and engage the engagement recess 304, preferably automatically when the pressure jacket 32" is connected to or engaged with the faceplate 18". The elongated proximal portion 306 at the proximal end 44" of the pressure jacket 32" defines an external cam surface 308, that is generally shaped to displace or depress the engagement tab 302 radially outward when the pressure jacket 32" is connected to the faceplate 18". The cam surface 308 may have a generally arcuate distal end or tip that tapers outward in the form of a tapered ramp, so that the engagement tab 302 is smoothly displaced or depressed radially outward as the pressure jacket 32" is mounted on or connected to the faceplate 18". The elongated portion 306 may further define an inner step 310 within the pressure jacket 32" to prevent over-insertion of the syringe 24 in the pressure jacket 32", as discussed further herein.

Figure 36:
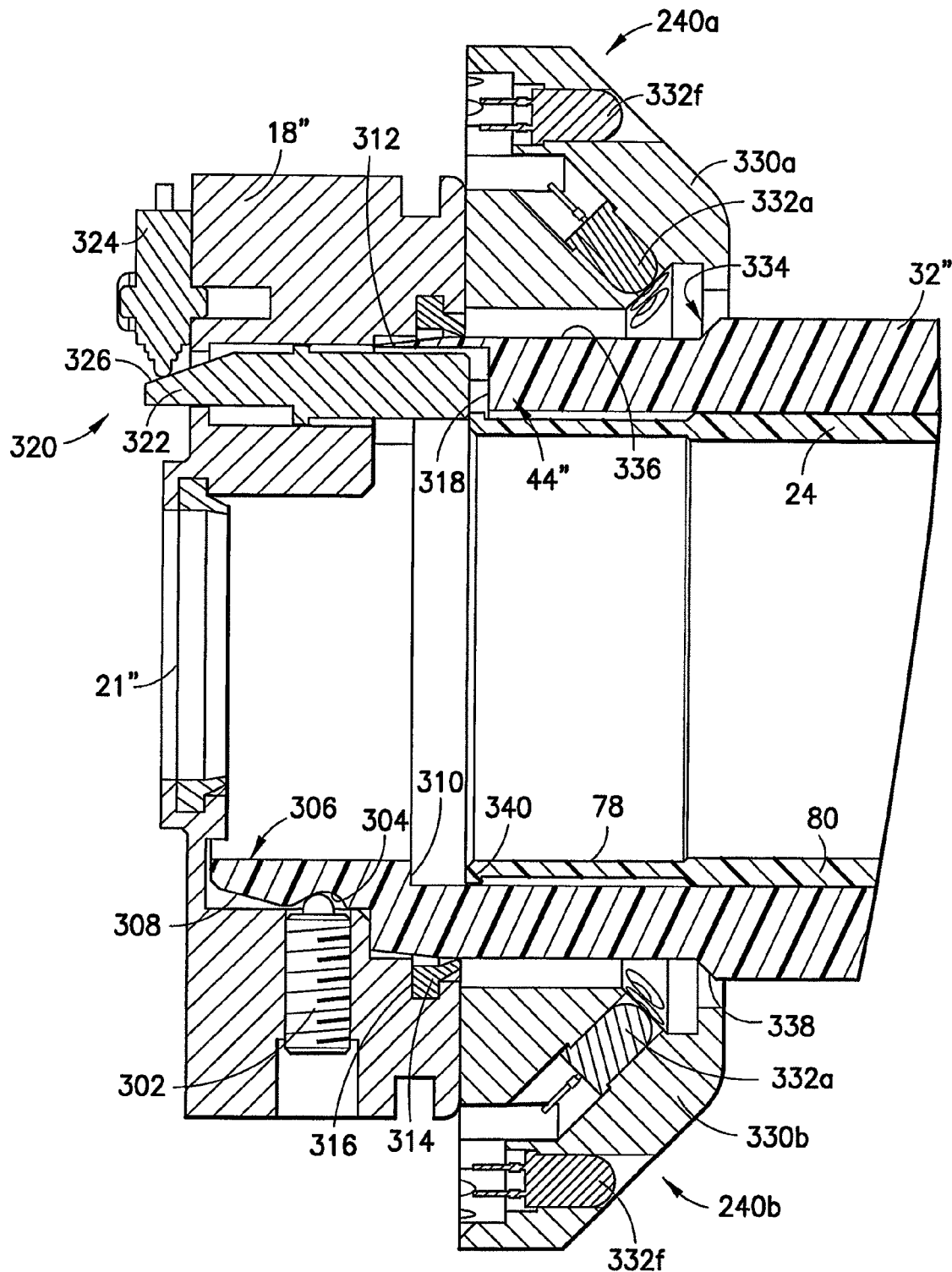
FIG. 36 is a cross sectional view of a portion of a proximal end of the fluid injection apparatus shown in FIG. 32.

As shown in detail in FIG. 36, the proximal end 44" of the pressure jacket 32" may be formed with a tapered proximal outer surface 312, which extends circumferentially about the proximal end 44" and which aids in guiding the proximal end 44" of the pressure jacket 32" into engagement with the faceplate 18". Additionally, a sealing bushing 314 may be provided in a circumferential recess or groove 316 formed in the faceplate 18". The sealing bushing 314 is generally adapted to engage the tapered proximal outer surface 312. The sealing bushing 314 forms a barrier that substantially prevents contaminants and liquids from entering the central passage 21" in the faceplate 18" when the injector head 12" is used in an injection procedure. The sealing bushing 314 may be made of molythane or a similar material. The proximal end 44" of the pressure jacket 32" may further define an internal recess portion 318 for accommodating the syringe sensor to be discussed herein.

As indicated previously, a syringe sensor 320 is preferably associated with the faceplate 18" and therefore the injector housing 14" of the injector head 12". The recess portion 318 at the proximal end 44" of the pressure jacket 32" is preferably configured to accommodate the syringe sensor 320 without activating the syringe sensor 320 when the pressure jacket 32" is connected to the faceplate 18". The syringe sensor 320 is generally a two-piece component comprised of an actuating member or pin 322 and an electrical switch 324. A suitable model for the electric switch 324 is manufactured by Omron. The actuating member 322 includes a tapered proximal surface 326 in engagement or contact with the electrical switch 324 and is adapted to activate the electrical switch 324 once a syringe 24 is loaded into the pressure jacket 32" and engages the actuating member 322. In particular, as shown best in FIG. 36, when the syringe 24 is loaded into the pressure jacket 32", the proximal end 74 of the syringe 24 engages or contacts the actuating member 322. In operation, as the syringe 24 is initially inserted into the pressure jacket 32" during a loading operation, the proximal end 74 of the syringe 24 will initially contact the actuating member 322. When the syringe 24 is fully inserted into the pressure jacket 32" and secured in place in the pressure jacket 32" by the components of the pressure jacket assembly 30", the proximal end 74 of the syringe 24 will move the actuating member 322 proximally into the faceplate 18", which causes the tapered proximal surface 326 of the actuating member 322 to move proximally. The increased thickness of the actuating member 322 provided by the tapered proximal surface 326 will depress and activate the electrical switch 324, which is preferably adapted to generate a signal indicating the presence of the syringe 24 in the pressure jacket 32" and which could be used as a control signal by the injector head 12" indicating, for example, that the syringe 24 may now be filled with fluid. The actuating member 322 is preferably normally biased, for example by a spring 325, to a non-activating position relative to the electrical switch 324. The biasing force acting on the actuating member 322 is overcome when the syringe 24 is loaded in the pressure jacket 32" and secured in place therein by the elements of the pressure jacket assembly 30".

Another difference between the pressure jacket assembly 30" of FIGS. 32-39 and the pressure jacket assemblies 30, 30' discussed previously, is the lighting arrangement provided for by the at least one light source 240. As shown in FIGS. 32-36, the light source 240 is provided as opposing light sources 240a, 240b, which are located on opposite sides of the pressure jacket 32". In particular, the opposing light sources 240a, 240b include respective light source housings 330a, 330b and internally positioned lights 332, such as light-emitting diodes (LED's) or similar light-emitting elements. The light source housings 330a, 330b may be connected to the faceplate 18" by any suitable mechanical or adhesive means. While the light source housings 330a, 330b are illustrated as being located on the top and bottom of the faceplate 18" in the views shown in FIGS. 32-36, other configurations, such as locating the light source housings 330a, 330b on opposing lateral sides of the faceplate 18", are also within the scope of the present invention. Additionally, only one of the light sources 240a, 240b, such as upper light source 240a, is required for the pressure jacket assembly 30" of the present invention. The configuration for light sources 240a, 240b generally shown in FIGS. 32-36 may be applied to any of the embodiments of the fluid injection apparatus 10, 10', injector head 12, 12', and pressure jacket assembly 30, 30' discussed previously.

As shown in detail in FIG. 36, the respective light source housings 330a, 330b each preferably include a plurality of lights 332. In the arrangement illustrated in FIGS. 32-36, the respective light source housings 330a, 330b include at least one inward-directed or angled light 332a. The angled lights 332a illuminate the pressure jacket 32" on opposing lateral sides thereof, with the light transmitted through the pressure jacket 32" being diffused by the pressure jacket 32" into the syringe 24 loaded into the pressure jacket 32". The respective housings 330a, 330b may further include a plurality of forward directed lights $332_f$ that may be used to illuminate the syringe 24 along a longitudinal axis thereof, or for other purposes such as indicating when the injector head 12" is ready to begin an injection procedure using the syringe 24.

The pressure jacket 32" is preferably formed with a light diffusing device or structure 334 that is formed as part of the wall 246" of the pressure jacket 32". The light diffusing structure 334 is generally formed by a recessed portion 336 of the pressure jacket 32", which is located generally at the proximal end 44" of the pressure jacket 32". The recessed portion 336 defines a beveled surface 338, which is adapted to diffuse the light entering the pressure jacket 32" from the angled light sources $332_a$. The beveled surface 338 is preferably located substantially opposite from the angled light sources $332_a$ when the pressure jacket 32" is connected to the faceplate 18".

The light sources 240a, 240b, as was the case in the previously discussed embodiments of the present invention, are used to illuminate the syringe 24 when loaded into the pressure jacket 32" and, further, the fluid contents of the syringe 24 when the syringe 24 is to be used in an injection procedure involving the injector head 12". The light-illumination of the syringe 24 enhances the ability of the operator of the fluid injection apparatus 10" to view the contents of the syringe 24 during operation of the injector head 12". The enhanced ability to view the fluid contents of the syringe 24 provided by the light sources 240a, 240b allows the operator to spot potential problems during the injection procedure, such as the presence of air bubbles in the syringe 24. The different lighting arrangements set forth in this disclosure enhance the user's ability to view the contents of the syringe 24 when filled with an injection fluid, and avoid possible injection of air bubbles into a patient's body. The angled orientation of the light sources 240a, 240b ensure that the syringe 24 is illuminated along lateral sides thereof, and generally along the longitudinal axis of the syringe 24. The beveled surface 338 on the pressure jacket 32" forms a diffusing lens or structure on the body of the pressure jacket 32", which diffuses the light passing into the syringe 24 from the light sources 240a, 240b for providing effective viewing of the contents of the syringe 24.

The beveled surface 338 does not need to extend completely about the circumference of the pressure jacket 32", and need only extend partially about the circumference of the pressure jacket 32, typically in the vicinity of the top and bottom light sources 240a, 240b. Thus, the pressure jacket 32" could be formed with two beveled surfaces 338 located on opposite side of the pressure jacket 32" which would be substantially coincident with the top and bottom light sources 240a, 240b when the pressure jacket 32" is engaged with the faceplate 18".

Figures 37A, 37B:
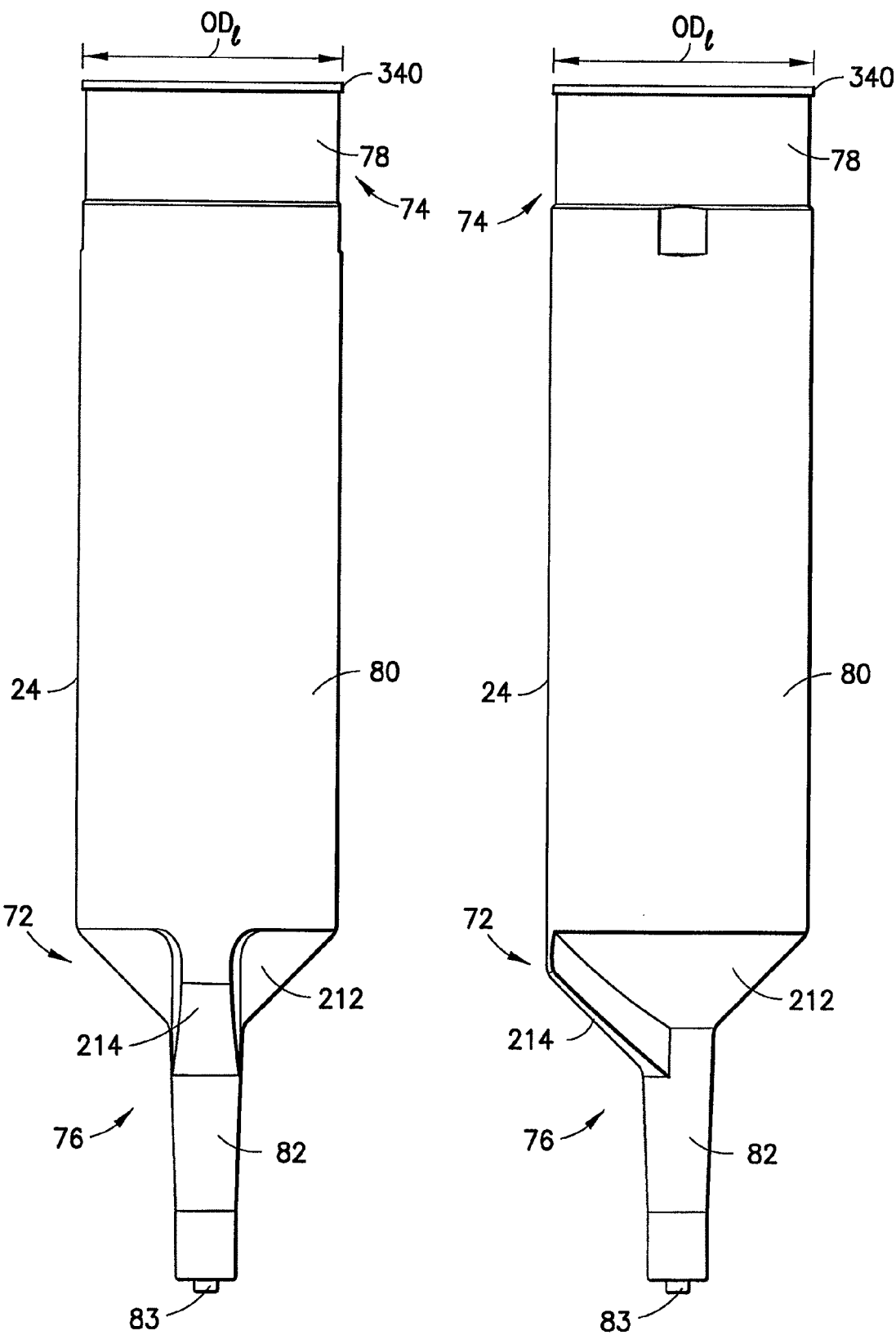
FIGS. 37A and 37B are respective views showing a syringe adapted for use with the fluid injection apparatus shown in FIG. 32.
Figure 38:
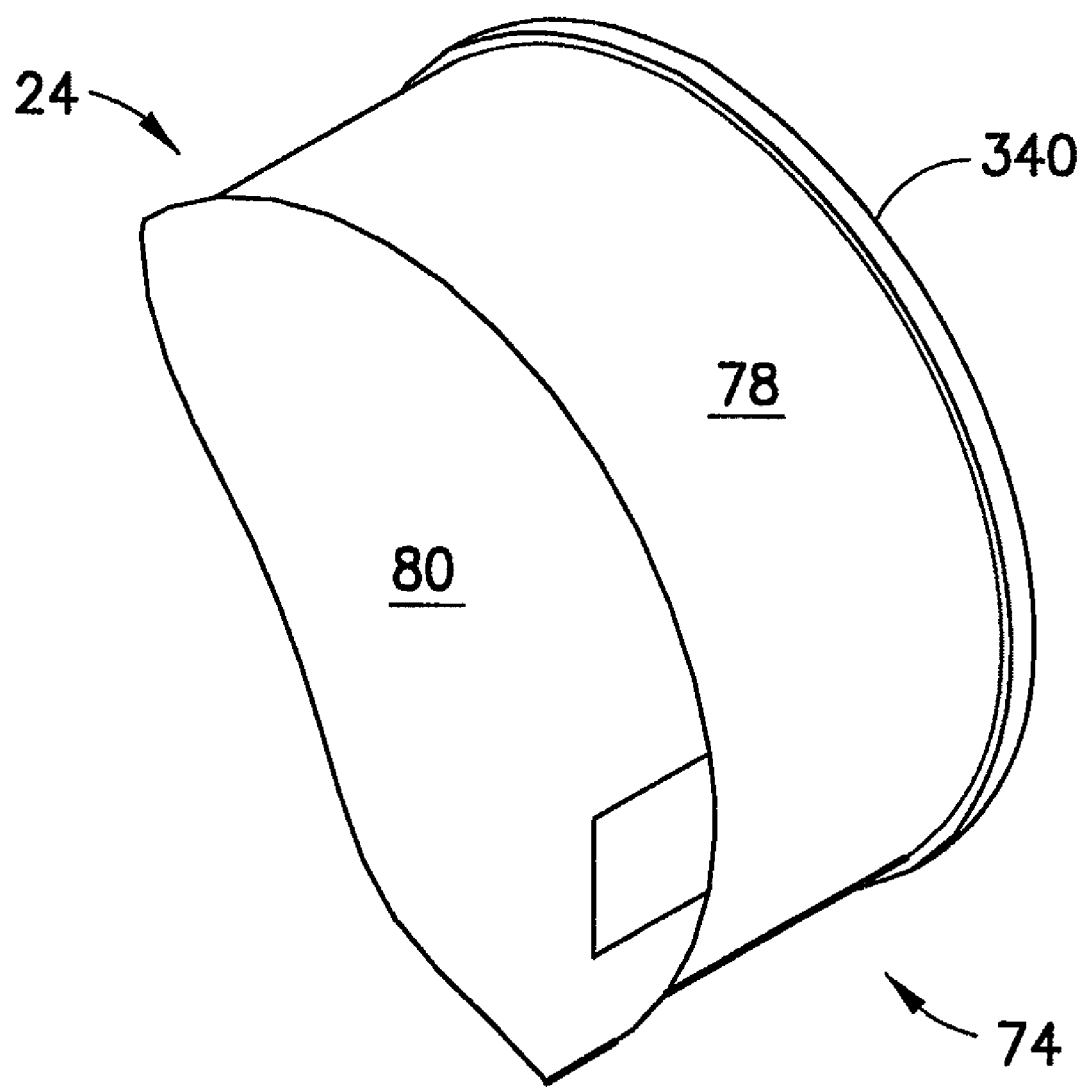
FIG. 38 is a perspective view a proximal end of the syringes shown in FIGS. 37A and 37B.
Figure 39A:
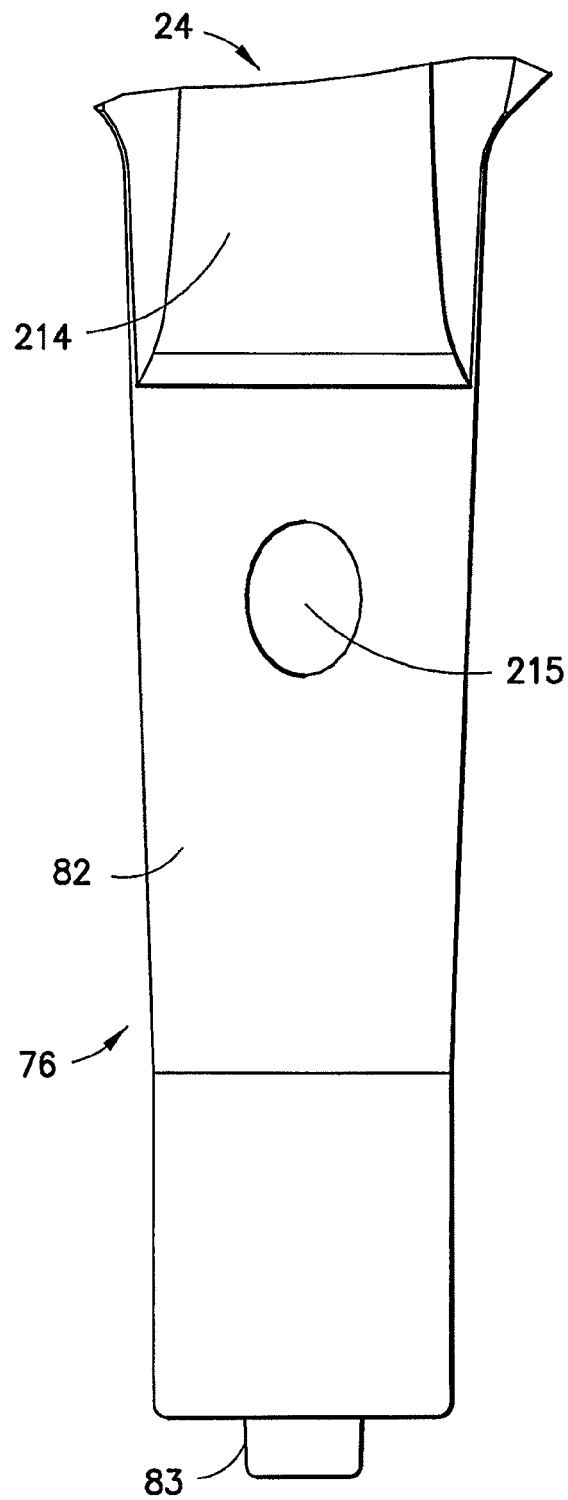
FIGS. 39A and 39B are respective views showing an injection section of the syringe shown in FIGS. 37A and 37B.
Figure 39B:
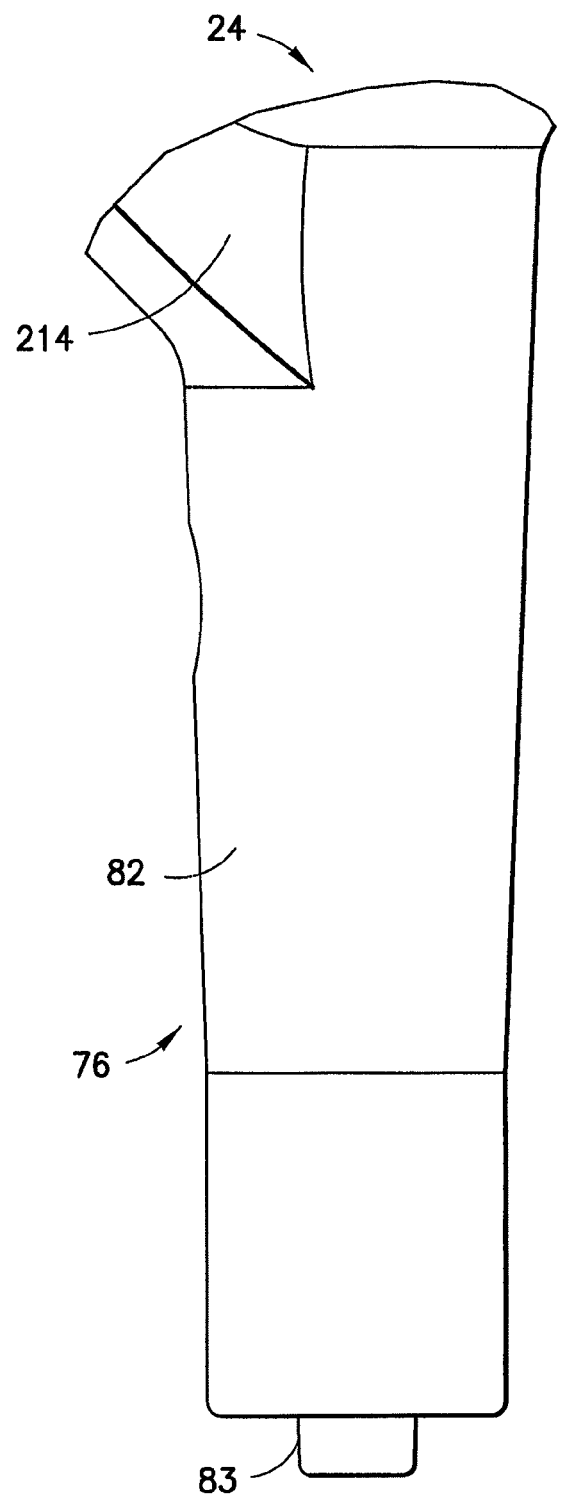

The syringe 24 used with the pressure jacket 32" and pressure jacket assembly 30", which are the subject matter of FIGS. 32-36, includes all the features discussed previously in connection with FIGS. 21, 22 and 28, 29, and in particular, the expansion section 78 for accommodating the plunger 216, the alignment flange or tab 212 for aligning the syringe 24 in the pressure jacket assembly 30", and fluid dot 215 (see FIG. 39). However, the syringe 24 preferably includes an additional structure or feature adapting the syringe 24 specifically for use with the pressure jacket 32". As FIGS. 37 and 38 illustrate, the proximal end 74 of the syringe body 70 defines an outward extending lip 340. The "proximal" lip 340 is adapted to engage or contact the actuating member 322 when the syringe 24 is loaded into the pressure jacket 32". The raised proximal lip 340 provides a sufficient, outward extending proximal structure at the proximal end 74 of the syringe 24 to enable the syringe 24 to engage the actuating member 322 and depress or move the actuating member 322 proximally to activate the electrical switch 324. However, the proximal lip 340 preferably has an outer diameter $OD_1$ that is no greater than the outer diameter $OD_{cs}$ of the center section 80 so that the syringe 24 is smoothly accepted into the pressure jacket 32" during a loading procedure, and so that the syringe 24 used with the pressure jacket 32" may be formed with the expansion section 78 used to store a syringe plunger prior to using the syringe 24. Moreover, as illustrated in FIG. 36, the proximal lip 340 may engage the inner step 310 within the pressure jacket 32", which will serve as a stop to prevent over-insertion of the syringe 24 into the pressure jacket 32".

Referring to FIGS. 40-43, a further aspect of the present invention is generally illustrated. FIGS. 40-43 illustrate several embodiments of an anti-rotation connection 350 between the injector drive piston 22 generally extendable from the injector head 12 and outward from the injector housing 14 (See FIG. 1), and the syringe plunger 216 disposed within the syringe 24 (See FIGS. 3, 28, and 29). The anti-rotation connection or arrangement 350 may be applied to any of the embodiments of the fluid injection apparatus 10, 10', 10" and syringes 24 set forth in this disclosure. The anti-rotation connection or arrangement 350 generally limits or substantially prevents rotational movement of the syringe plunger 216 disposed within the syringe 24 during operation of the injector head 12. The anti-rotation connection 350 will be discussed herein with general reference to FIGS. 1 and 3, and the respective embodiments of the anti-rotation connection 350 shown in FIGS. 40-43. However, the principles and structures discussed herein are applicable to any of the embodiments of the fluid injection apparatus 10, 10', 10" and injector head 12, 12', 12" discussed previously.

The injector drive piston 22 generally has a plunger engaging end 352 generally adapted to engage and capture the syringe plunger 216 to move the syringe plunger 216 in the syringe 24. The syringe plunger 216 generally has a distal end generally defined by the base member 220 and cover 222 and a proximal end generally formed or defined by the coupling end 224 of the syringe plunger 216. The proximal or coupling end 224 of the syringe plunger 216 is generally adapted for engagement by the plunger engaging end 352 of the injector drive piston 22. In general, the plunger engaging end 352 of the injector drive piston 22 comprises an anti-rotation element or structure 354 that is generally adapted to interact with the proximal or coupling end 224 of the syringe plunger 216 to substantially prevent or limit rotation of the syringe plunger 216 in the syringe 24, which can occur during operation of the injector head 12 when the injector drive piston 22 engages, captures, and moves the syringe plunger 216 in the syringe 24.

Figure 40A:
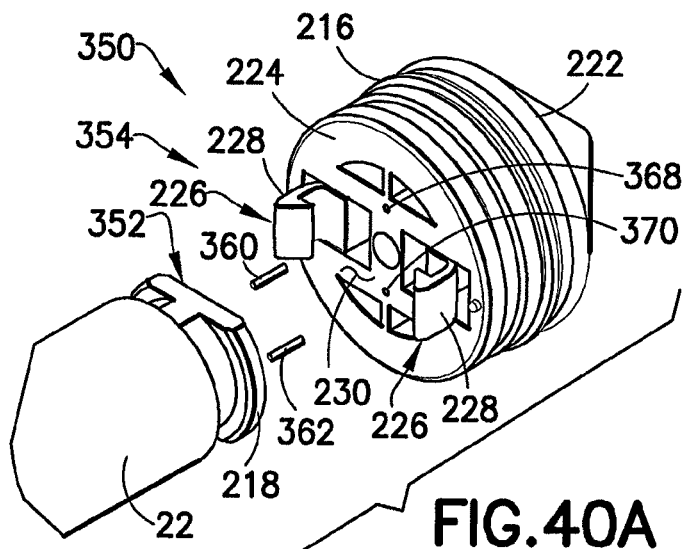
FIGS. 40A, 40B, and 40C are respective perspective views showing an anti-rotation connection between a drive piston of the fluid injection apparatus and a syringe plunger used in the syringes of the present invention.
Figure 40B:
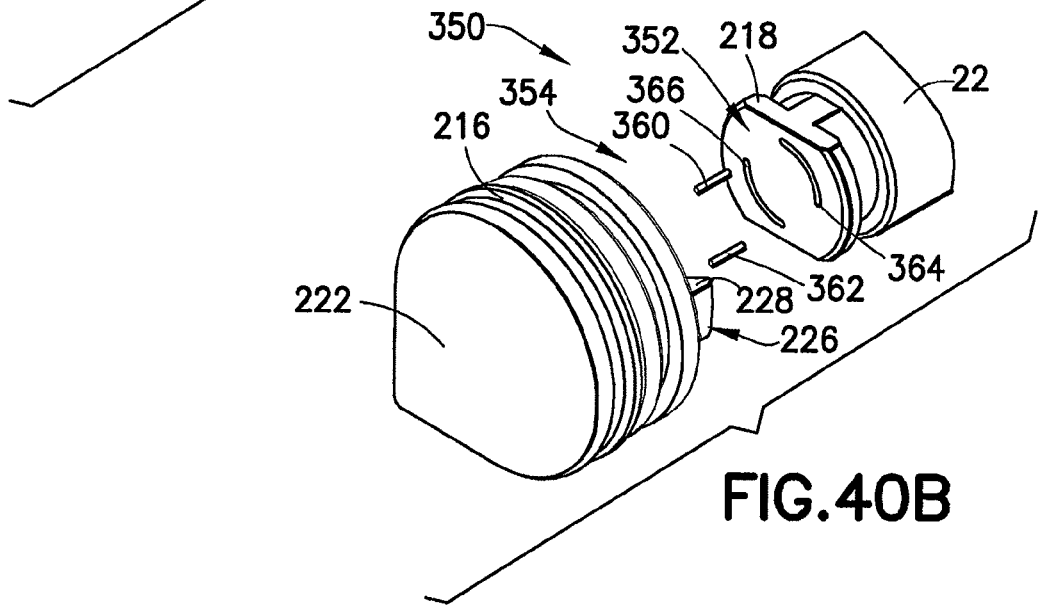
Figure 40C:
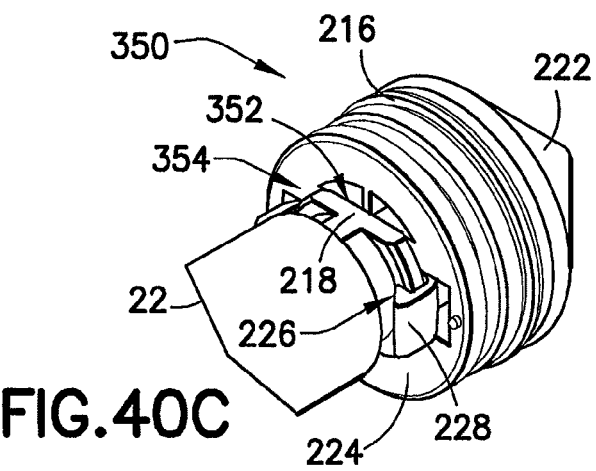

The anti-rotation element or structure 354 may take a number of different configurations in accordance with the present invention, as indicated previously. The respective embodiments of the anti-rotation element or structure 354 are respectively illustrated in FIGS. 40-43. Referring first to FIGS. 40A-40C, a first version or embodiment of the anti-rotation element or structure 354 is formed or defined by a pair of pins 360, 362 that extend distally from the plunger engaging end 352 of the injector drive piston 22, and which are preferably spaced apart on the plunger engaging end 352. In particular, the pins 360, 362 extend from the injector end plate 218 attached to the drive piston 22. The pins 360, 362 may be associated with opposing arcuate slots 364, 366 defined in the injector end plate 218, which permit the pins 360, 362 to traverse respective arcs on the injector end plate 218, thereby permitting the syringe plunger 216 to rotate to some degree in the syringe 24 as discussed further herein.

The injector end plate 218 of the injector drive piston 22 preferably forms the plunger engaging end or structure 352 of the injector drive piston 22. The pins 360, 362 are generally adapted to cooperate or engage a pair of pin receiving openings 368, 370 defined in the proximal or coupling end 224 of the syringe plunger 216. The engagement of the pins 360, 362 with the pin receiving openings 364, 366 will substantially prevent or limit rotation of the syringe plunger 216 in the syringe 24, when the injector drive piston 22 is engaged with the syringe plunger 216 during operation of the injector head 12. While a pair of the pins 360, 362 is illustrated in FIGS. 40A-40C, a single pin 360 cooperating or interacting with a single pin receiving opening 368 is sufficient to substantially prevent or limit rotation of the syringe plunger 216 in the syringe 24 during operation of the injector head 12.

As indicated previously, the pins 360, 362 may optionally be associated with the two opposing slots 364, 366 formed or defined in the injector end plate 218. The opposing slots 364, 366 are generally provided if it desired to allow the syringe plunger 216 to rotate to some degree in the syringe 24, such as along an arc of a circle. However, while the slots 364, 366 permit such movement, the slots 364, 366 generally prevent the syringe plunger 216 from rotating completely through a 360° revolution in the syringe 24. The slots 364, 366 may be eliminated and the pins 360, 362 made to extend from the injector end plate 218 and engage the respective syringe receiving openings 368, 370, such that the syringe plunger 216 will be prevented from any rotational movement in the syringe 24.

Figure 41A:
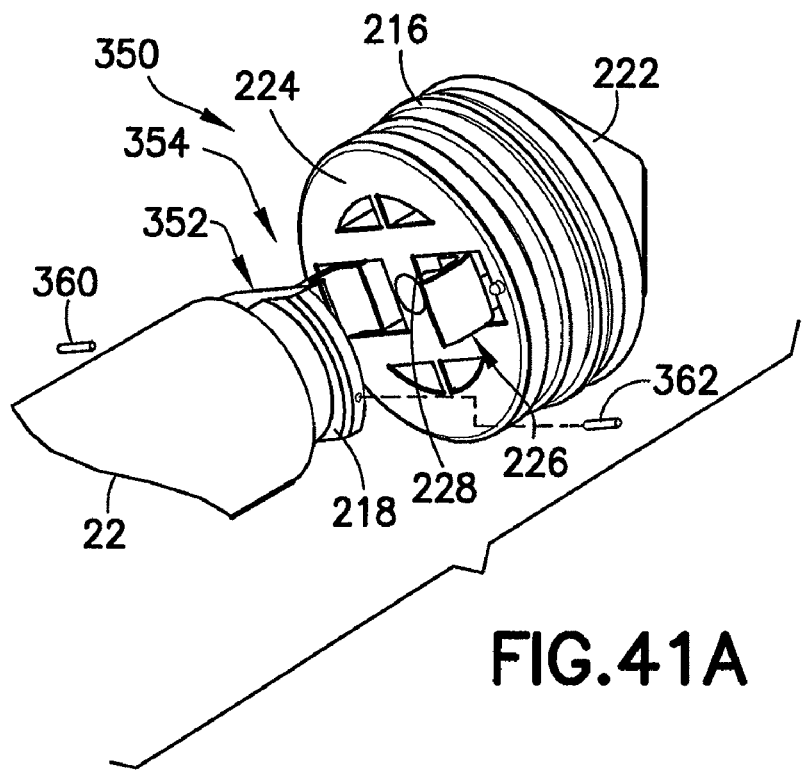
FIG. 41A and FIG. 41B are perspective views showing an alternative embodiment of the anti-rotation connection shown FIGS. 40A and 40B.
Figure 41B:
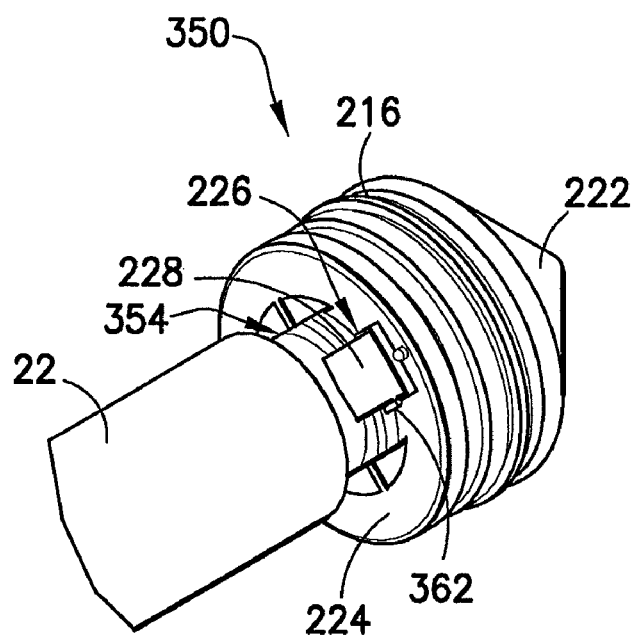

A modification to the anti-rotation element or structure 354 shown in FIGS. 40A-40C is illustrated in FIGS. 41A and 41B. In the modification of the anti-rotation element or structure 354 shown in FIGS. 41A and 41B, the pins 360, 362 extend outward from opposing sides of the injector end plate 218 and interact with the coupling members 226 extending from the proximal or coupling end 224 of the syringe plunger 216 to substantially prevent or limit rotation of the syringe plunger 216 in the syringe 24. As FIG. 41B illustrates, the pins 360, 362 are spaced vertically apart on the injector end plate 218, and engage the engagement arms 228 of the coupling members 226 on respective top and bottom sides of the opposing engagement arms 228, which substantially prevents rotational movement of the syringe plunger 216 in the syringe 24. As indicated previously, the coupling members 226 may be may be flexible coupling members. As with the previous embodiment of the anti-rotation element or structure 354, a single outward extending pin 360 may be provided to engage one of the coupling members 226 to limit rotation of the syringe plunger 216. However, the opposing pins 360, 362 engaging respective top and bottom sides of the engagement arms 228 of the coupling members 226 are preferred because of the limited rotational movement that will be allowed by this arrangement, as will be appreciated by those skilled in the art.

Figure 42A:
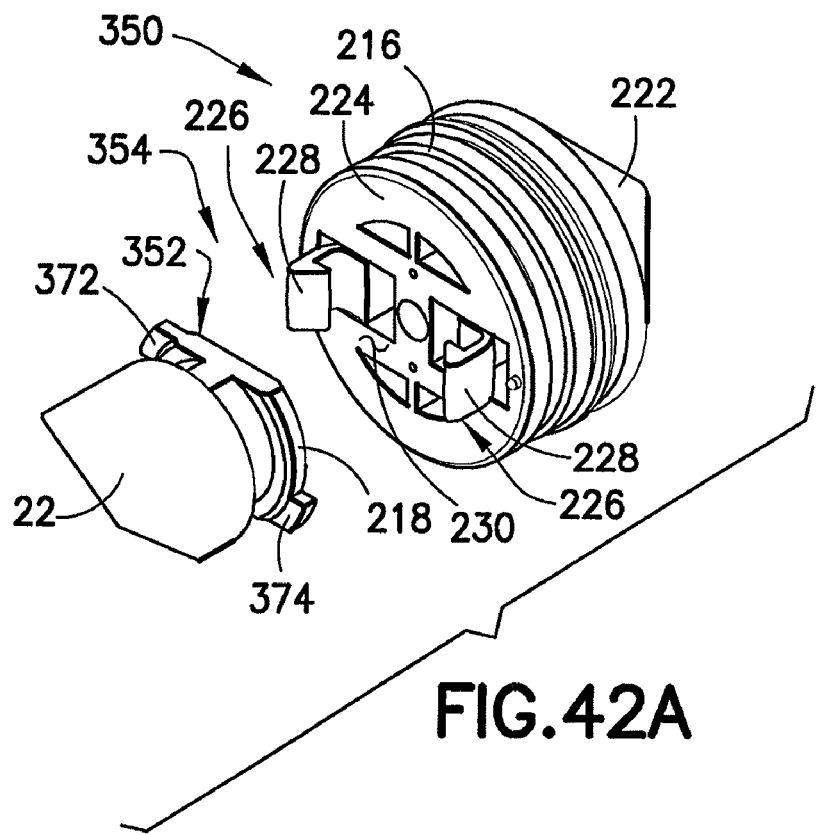
FIG. 42A and FIG. 42B are perspective views showing another embodiment of the anti-rotation connection of the present invention.
Figure 42B:
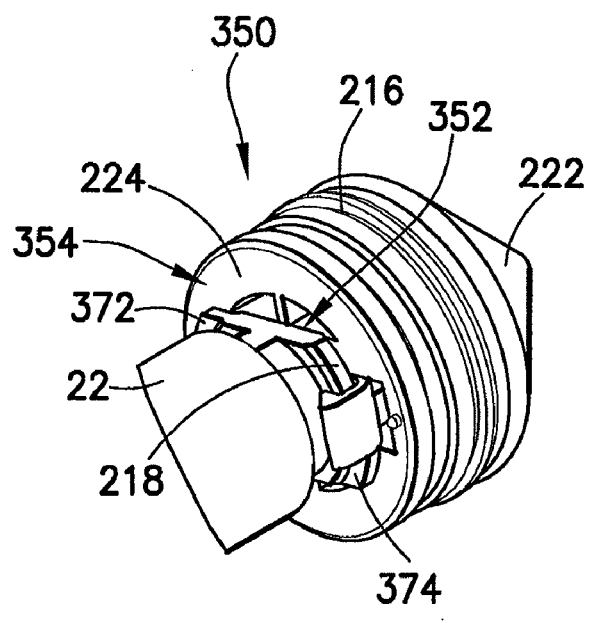

In a further configuration shown in FIGS. 42A and 42B, the anti-rotation element or structure 354 comprises opposing tabs 372, 374 provided at the plunger engaging end 352 of the injector drive piston 22. The opposing tabs 372, 374 are preferably formed on the injector end plate 218, which preferably forms the plunger engaging end 352 of the injector drive piston 22, as indicated previously. The opposing tabs 372, 374 are formed on (i.e., extend outward from) the injector end plate 218 in similar locations as the pins 360, 362 in the anti-rotation element or structure 354 illustrated in FIGS. 41A and 41B. Accordingly, the opposing tabs 372, 374 engage the engagement arms 228 of the coupling members 226 in a substantially identical manner to the pins 360, 362 illustrated in FIGS. 41A and 41B, and thus operate in a substantially identical manner to that discussed previously. As with the embodiment of the anti-rotation element or structure 354 discussed in connection with FIGS. 41A and 41B, a single outward extending tab 372 may be provided to engage one of the coupling members 226. However, the opposing tabs 372, 374 are preferred because of the limited rotational movement that will be allowed by this, as again will be appreciated by those skilled in the art.

Figure 43A:
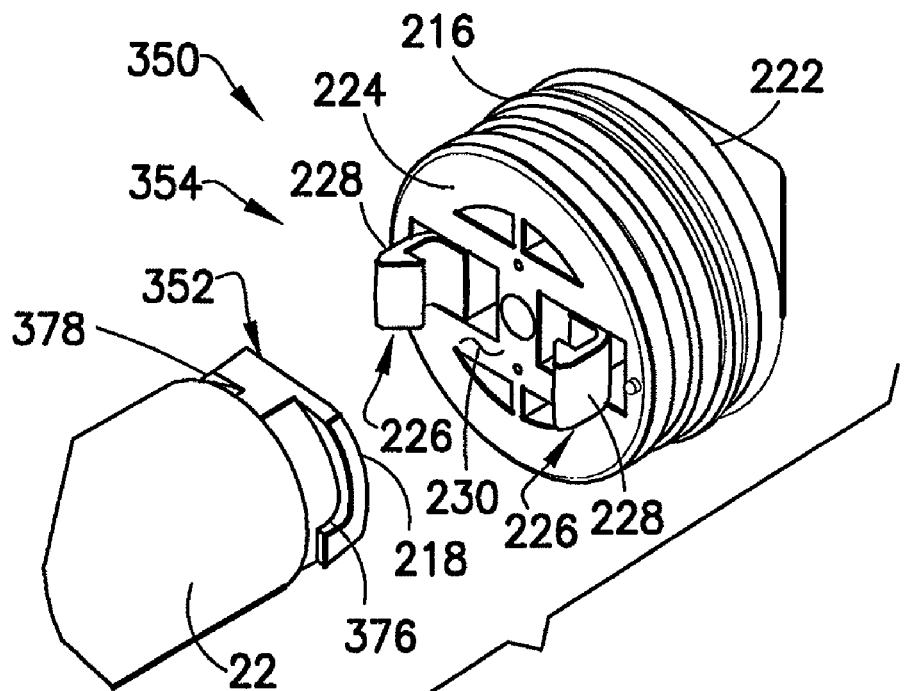
FIG. 43A and FIG. 43B are perspective views showing a further embodiment of the anti-rotation connection of the present invention.
Figure 43B:
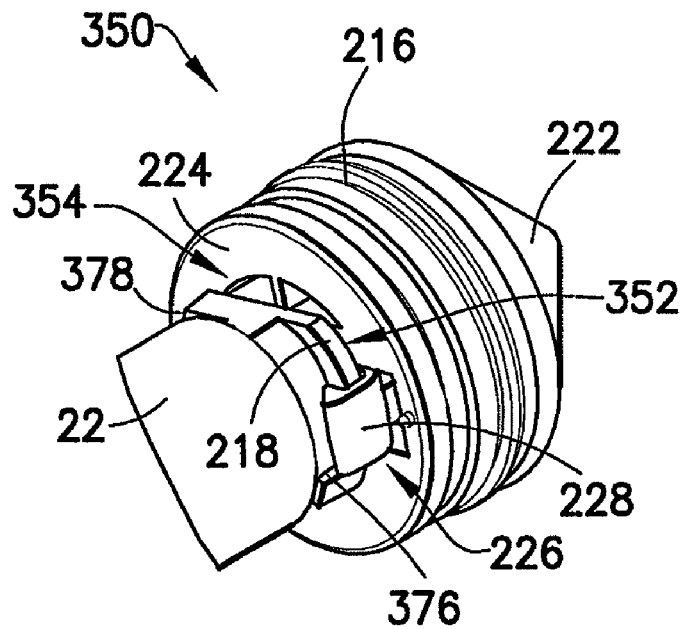

In a still further configuration shown in FIGS. 43A and 43B, the anti-rotation element or structure 354 comprises opposing edges 376, 378 formed on the plunger engaging end 352 of the injector drive piston 22, and which are generally adapted to be engaged by the engagement arms 228 of the coupling members 226 when the injector drive piston 22 engages the syringe plunger 216. The opposing edges 376, 378 may be formed as part of the injector end plate 218, as depicted in FIGS. 43A and 43B, or formed as part of one or more grooves defined in the shaft of the injector drive piston 22. The opposing edges 376, 378 are provided on opposite sides of the injector end plate 218 and spaced vertically apart on the injector end plate 218 in much the same manner as the pins 360, 362 illustrated in FIGS. 41A and 41B and the tabs 372, 374 illustrated in FIGS. 42A and 42B, and generally operate in an analogous manner to these embodiments of the anti-rotation element or structure 354. In particular, when the injector drive piston 22 is engaged with the syringe plunger 216, the opposing engagement arms 228 of the coupling members 226 engage the respective opposing edges 376, 378 on the injector end plate 218, which limits or substantially prevents rotational movement of the syringe plunger 216 in the syringe 24.

Figure 32:
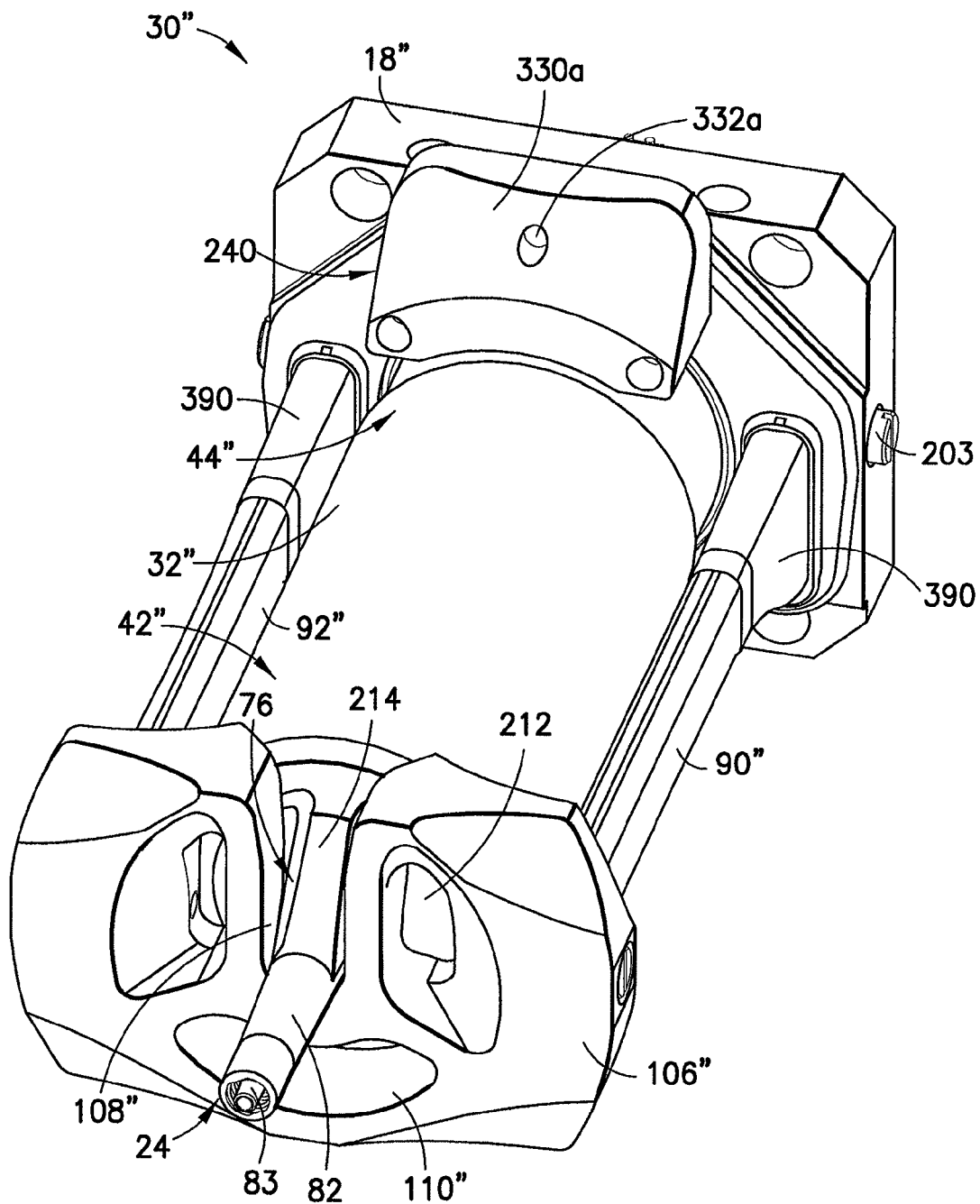
FIG. 32 is a perspective view of another embodiment of the fluid injection apparatus and pressure jacket assembly having an alternative lighting arrangement.
Figure 33:
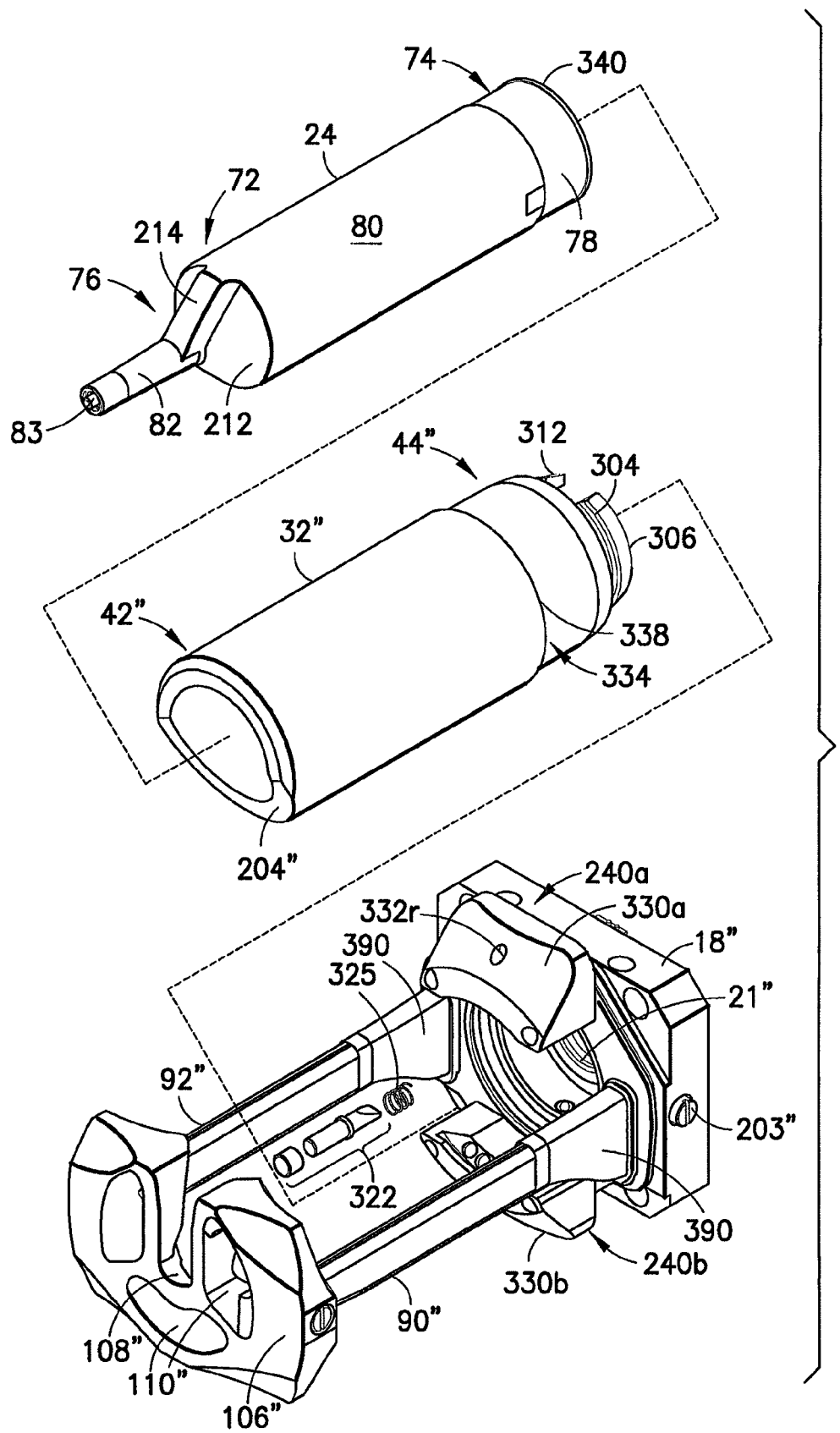
FIG. 33 is an exploded perspective view showing the elements of the fluid injection apparatus shown in FIG. 32.
Figure 34:
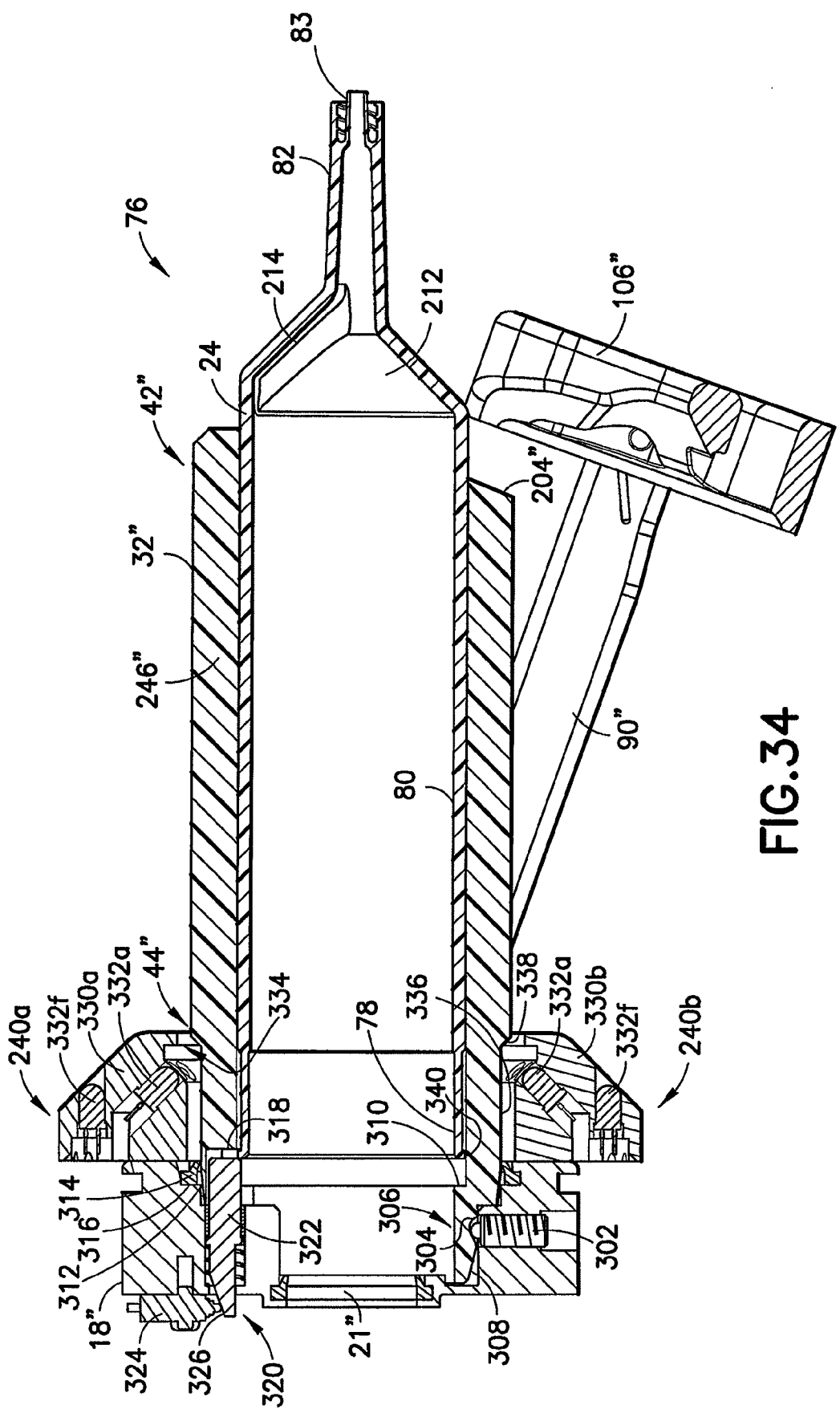
FIG. 34 is a cross sectional view of the fluid injection apparatus shown in FIG. 32 with the syringe support structure in a partially pivoted position.
Figure 35:
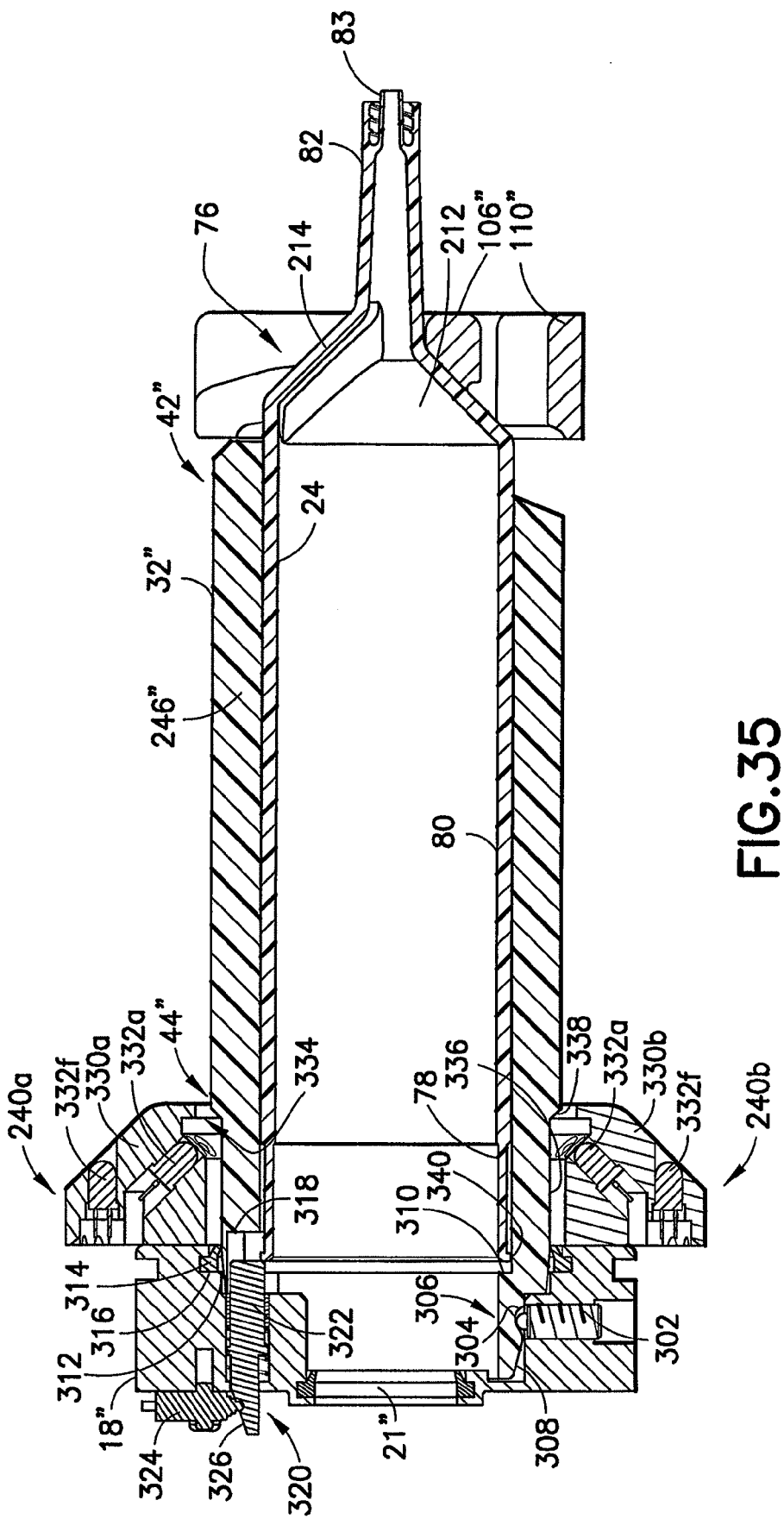
FIG. 35 is a cross sectional view of the fluid injection apparatus shown in FIG. 32 with the syringe support structure removed for clarity.

Referring briefly to FIGS. 32 and 33, the support arms of the 90", 92" of the injector head 12" may be enclosed by respective sleeves 390, which generally enclose the proximal ends 98", 100" (See FIG. 14) of the support arms 90", 92". The sleeves 390 preferably extend to the faceplate 18, and cover the front openings 94", 96" (See FIG. 14) to prevent contaminants from entering the injector head 12" during operation of the fluid injection apparatus 10". The sleeves 390 are preferably made of a resilient material allowing the support arms 90", 92" to pivot in the manner discussed previously. Suitable materials for the sleeves 390 include polyurethane and silicone.

While the present invention was described with reference to preferred embodiments of the fluid injection apparatus and pressure jacket and syringe used therewith, those skilled in the art may make modifications and alterations to the present invention without departing from the scope and spirit of the invention. Accordingly, the above detailed description is intended to be illustrative rather than restrictive. The invention is defined by the appended claims, and all changes to the invention that fall within the meaning and range of equivalency of the claims are to be embraced within their scope.

What is claimed is:

1. A syringe, comprising:
a cylindrical main body, a conical portion connected to the main body and having a proximal end defining a radially-outward extending lip, and a discharge outlet connected to the conical portion;
a plunger movably disposed within at least a portion of the main body; and
a hollow alignment flange disposed on and extending outward from at least a portion of the conical portion, the alignment flange defining a fluid-containing area therein;
wherein the plunger has a coupling end comprising a pair of proximally-extending coupling members defining a slot therebetween, the slot substantially aligned with the alignment flange such that the alignment flange provides an indication of the orientation of the slot; and
wherein the alignment flange extends outward sufficiently from the conical portion to be grasped by a user of the syringe and used as a handle for manipulating the syringe.

2. The syringe of claim 1, wherein the coupling members comprise flexible coupling members.

3. The syringe of claim 1, wherein the conical portion comprises a light-sensitive fluid dot as an optical aid.

4. The syringe of claim 1, wherein the alignment flange is rectangular shaped and tapers from a center section to an injection neck.

5. The syringe of claim 1, wherein the discharge outlet is at a distal end of the main body and an expansion section is at a proximal end of the main body.

6. The syringe of claim 5, wherein the plunger is seated for storage in the expansion section prior to movement in the main body.

7. The syringe of claim 6, wherein a wall thickness of the main body narrows to a reduced wall thickness at the expansion section permitting the expansion section to expand under radial outward force exerted by the plunger during storage.

8. The syringe of claim 7, wherein the main body is made of a deformable material permitting the expansion section to expand radially when the plunger is seated in the expansion section for storage.

9. The syringe of claim 1, wherein the radially-outward extending lip extends around the circumference of the proximal end of the main body.

10. A syringe, comprising:
a body having a distal end and a proximal end, the body comprising an injection section at the distal end and an expansion section at the proximal end, the proximal end defining a radially-outward extending lip, the injection section and the expansion section connected by a center section of relatively uniform outer diameter; and a plunger movably received in the body for movement from the expansion section to the center section and seated for storage in the expansion section prior to movement to the center section, and the plunger comprising a cylindrical portion;

wherein a wall thickness of the body narrows to a reduced wall thickness at the expansion section such that an inner diameter of the expansion section is larger than the inner diameter of the center section allowing the expansion section to expand under radial outward force exerted by the plunger during storage;

wherein the expansion section has an axial length to accommodate the cylindrical portion of the plunger when seated for storage in the expansion section; and wherein the injection section comprises a conical portion and an injection neck, and wherein the conical portion comprises a hollow alignment flange extending outward from at least a portion of the conical portion, the alignment flange defining a fluid-containing area therein.

11. The syringe of claim 10, wherein the reduced wall thickness allows the expansion section to expand to an outer diameter no greater than approximately the outer diameter of the center section when the plunger is seated in the expansion section.

12. The syringe of claim 10, wherein the body is made of a deformable material permitting the expansion section to expand to an outer diameter no greater than approximately the outer diameter of the center section when the plunger is seated in the expansion section.

13. The syringe of claim 10, wherein an outer surface of the body is tapered or stepped inward toward a central axis of the body and an inner surface of the body is tapered or stepped outward away from the central axis of the body to form the reduced wall thickness.

14. The syringe of claim 10, wherein at least one of an outer surface of the body is tapered or stepped inward toward a central axis of the body and an inner surface of the body is tapered or stepped outward away from the central axis of the body to form the reduced wall thickness.

15. The syringe of claim 10, wherein the plunger has a coupling end comprising a pair of coupling members defining a slot therebetween.

16. The syringe of claim 15, wherein the slot defined between the coupling members is substantially aligned with the alignment flange such that the alignment flange provides an indication of the orientation of the slot.

17. The syringe of claim 15, wherein the coupling members comprise flexible coupling members.

18. The syringe of claim 10, wherein the conical portion further comprises a light-sensitive fluid dot as an optical aid.

19. The syringe of claim 10, wherein the plunger comprises a base member substantially enclosed by a cover to form the cylindrical portion and a conical portion of the plunger.

20. The syringe of claim 10, wherein the alignment flange is rectangular shaped and tapers from the center section to the injection neck.

21. The syringe of claim 10, wherein the radially-outward extending lip extends around the circumference of the proximal end of the body.

22. A syringe, comprising:

a cylindrical body having a distal end and a proximal end, the body comprising an injection section at the distal end and an expansion section at the proximal end, the proximal end defining a radially-outward extending lip, the injection section and expansion section connected by a cylindrical center section of relatively uniform outer diameter, the injection section comprising a conical portion and an injection neck, the conical portion comprising a hollow alignment flange extending outward from at least a portion of the conical portion and defining a fluid-containing area therein;

a plunger movably received in the body for movement from the expansion section to the center section and having a coupling end with a pair of flexible coupling members defining a slot therebetween for engaging a drive piston of an injector, the slot substantially aligned with the alignment flange such that the alignment flange provides an indication of the orientation of the slot, the plunger seated for storage in the expansion section prior to movement to the center section, and the plunger comprising a cylindrical portion;

wherein a wall thickness of the body narrows to a reduced wall thickness at the expansion section such that an inner diameter of the expansion section is larger than the inner diameter of the center section for allowing the expansion section to expand under radial outward force exerted by the plunger during storage; and wherein the expansion section has an axial length to accommodate the cylindrical portion of the plunger when seated for storage in the expansion section.

23. The syringe of claim 22, wherein the reduced wall thickness allows the expansion section to expand to an outer diameter no greater than approximately the outer diameter of the center section under the radial outward force exerted by the plunger.

24. The syringe of claim 22, wherein the body is made of a deformable material permitting the expansion section to expand to an outer diameter no greater than approximately the outer diameter of the center section under the radial outward force exerted by the plunger.

25. The syringe of claim 22, wherein an outer surface of the body is tapered or stepped inward toward a central axis of the body and an inner surface of the body is tapered or stepped outward away from the central axis of the body to form the reduced wall thickness.

26. The syringe of claim 22, wherein the alignment flange extends outward sufficiently from the conical portion to be grasped by a user of the syringe and used as a handle for manipulating the syringe.

27. The syringe of claim 22, wherein the alignment flange is rectangular shaped and tapers from the center section to the injection neck.

28. The syringe of claim 22, wherein the radially-outward extending lip extends around the circumference of the proximal end of the body.

* * * * *

UNITED STATES PATENT AND TRADEMARK OFFICE
CERTIFICATE OF CORRECTION

PATENT NO.        : 8,337,456 B2                                    Page 1 of 1
APPLICATION NO.   : 12/437011
DATED             : December 25, 2012
INVENTOR(S)       : Schriver et al.

It is certified that error appears in the above-identified patent and that said Letters Patent is hereby corrected as shown below:

ON THE COVER PAGE

On the Cover Page, item (54) and in the specification, column 1, Line 1, title, delete "PROXIMAL END" and insert -- HOLLOW ALIGNMENT FLANGE --, therefor.

On the Cover Page, item (75), under "Inventors", in Line 5, delete "Sewickly," and insert -- Sewickley, --, therefor.

IN THE DRAWINGS

Figure 14:
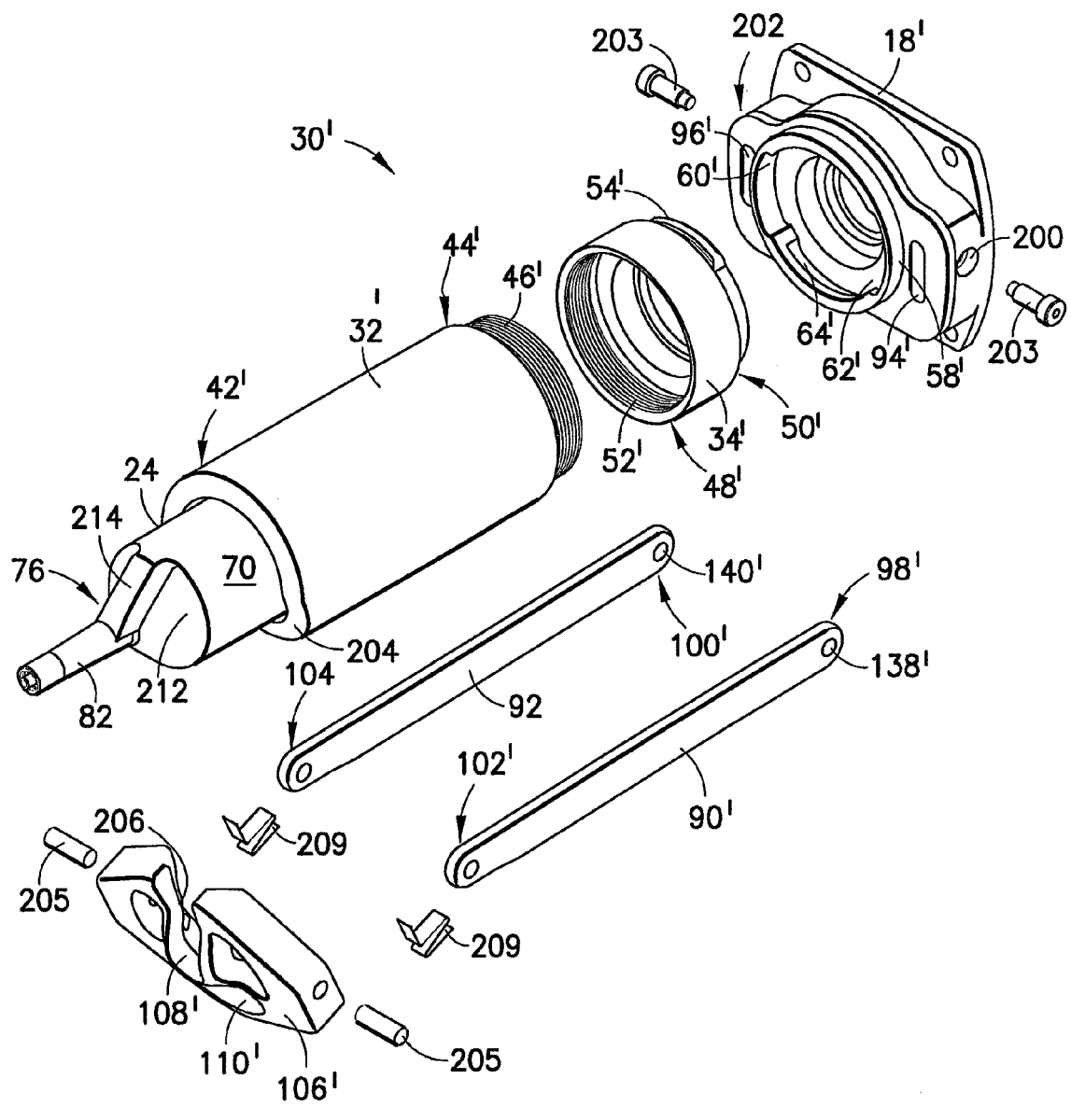
FIG. 14 is an exploded perspective view of the pressure jacket assembly of FIGS. 12 and 13.
Figure 15:
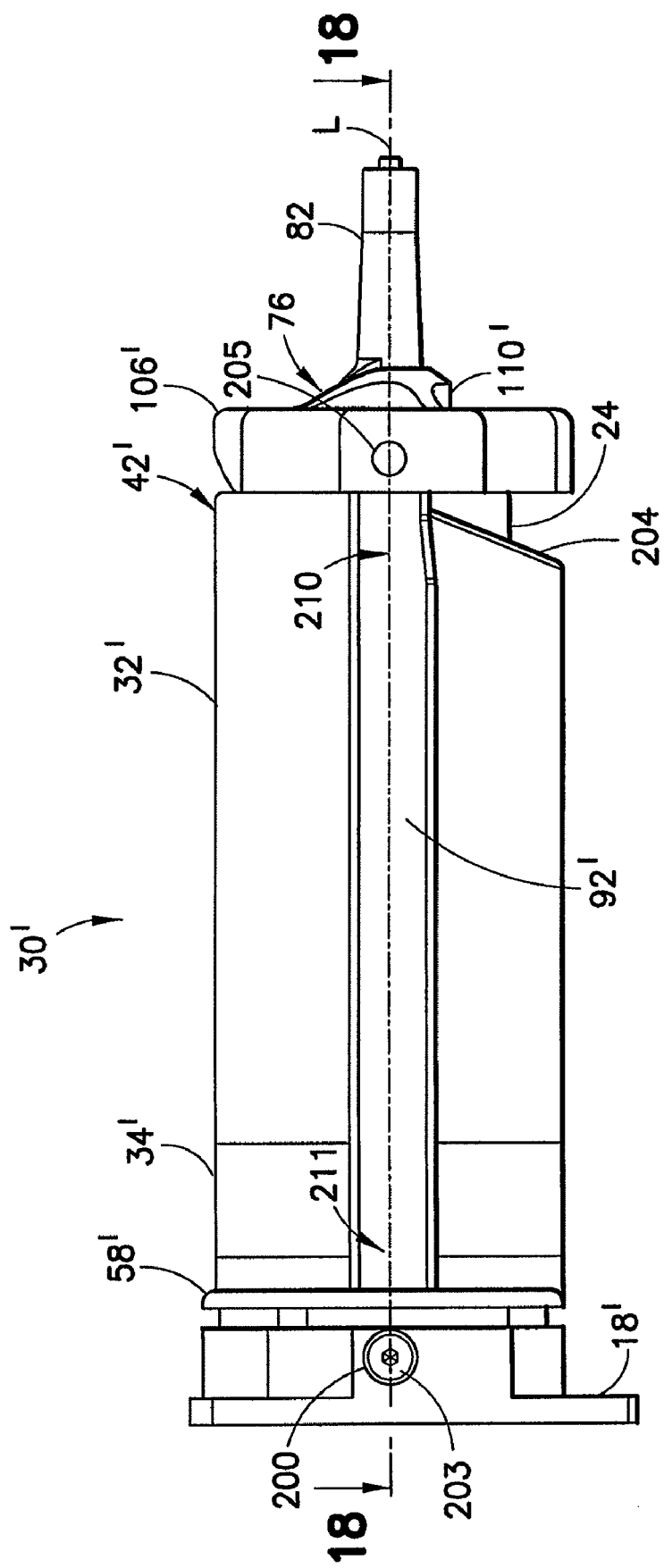
FIG. 15 is a side view of the pressure jacket assembly of FIG. 12.
Figure 16:
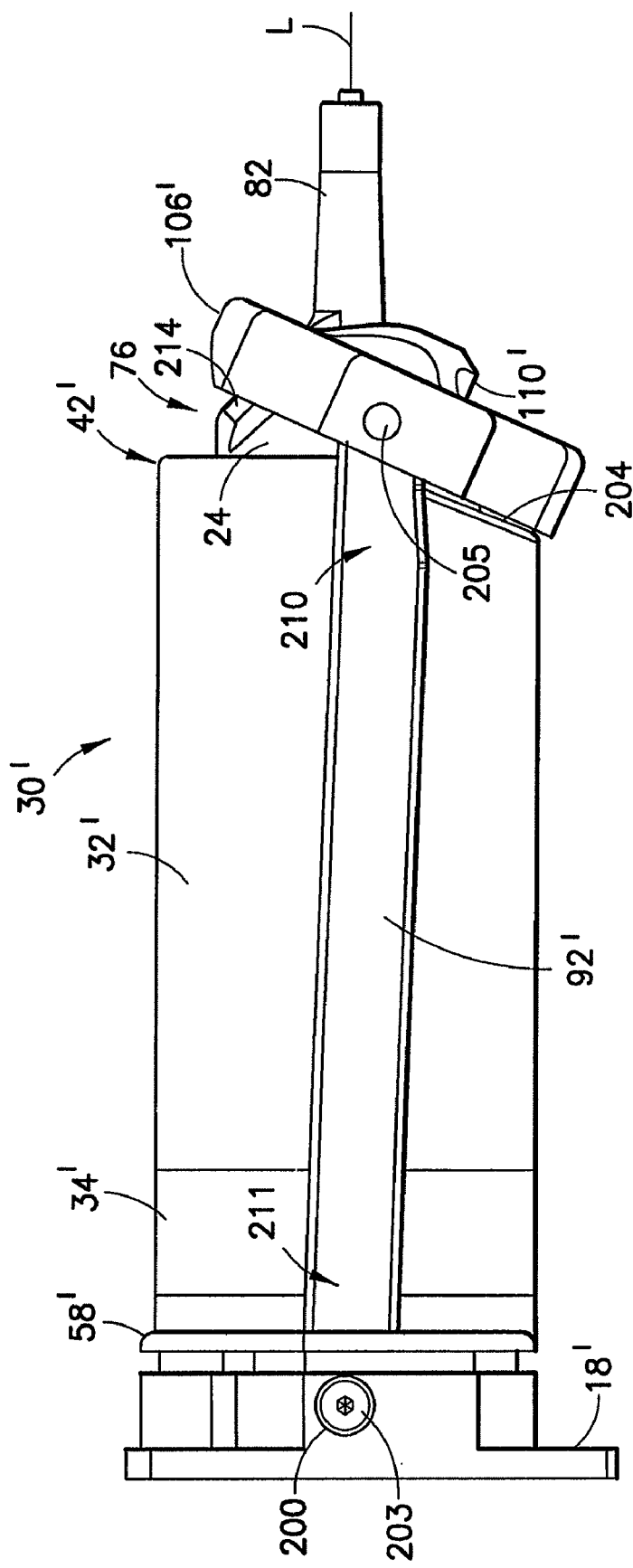
FIG. 16 is a side view of the pressure jacket assembly of FIG. 12 showing a syringe retaining member of the syringe support structure in a pivoted position.
Figure 17:
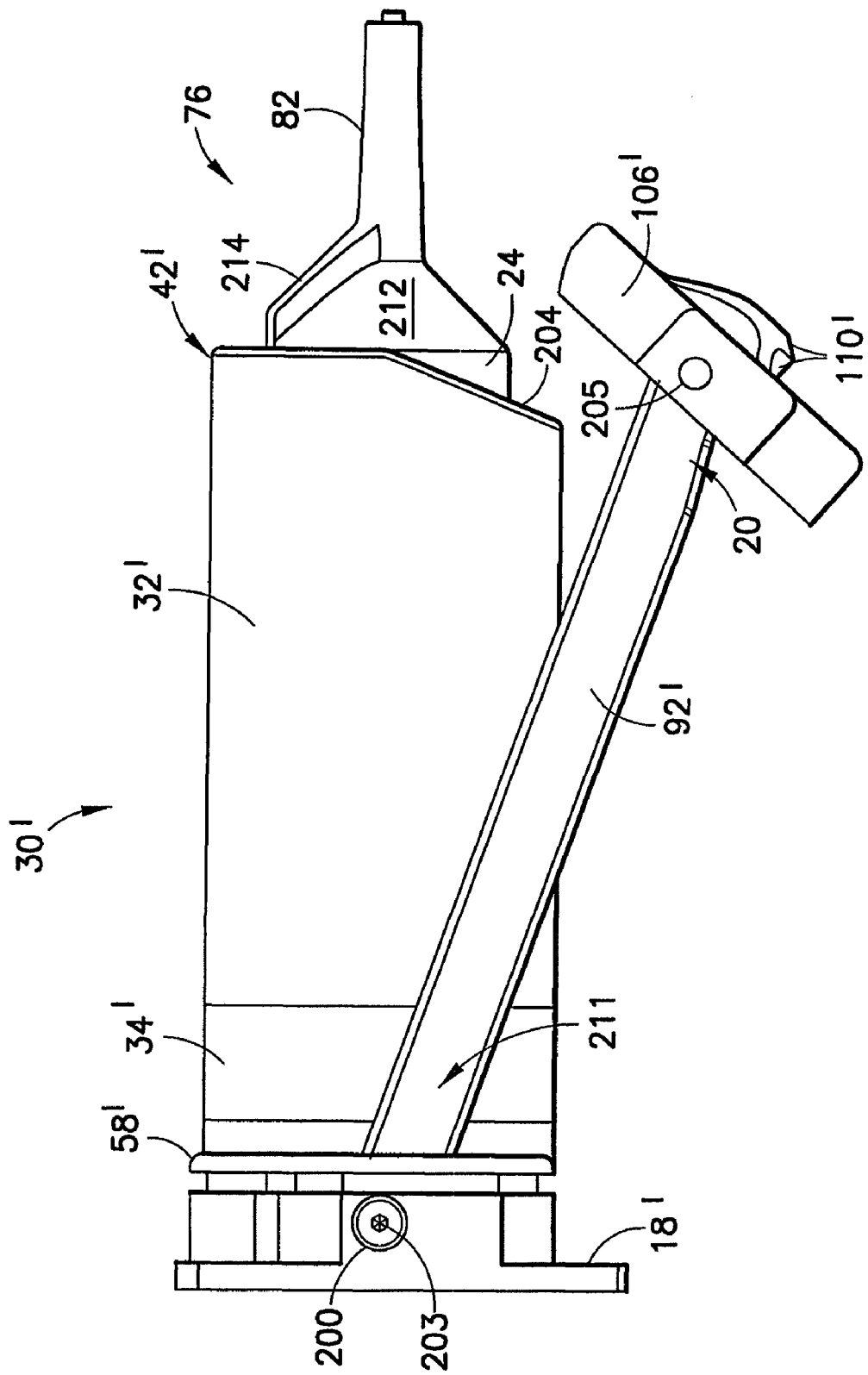
FIG. 17 is a side view of the pressure jacket assembly of FIG. 12 showing the syringe support structure in the syringe-disengaged position.
Figure 18:
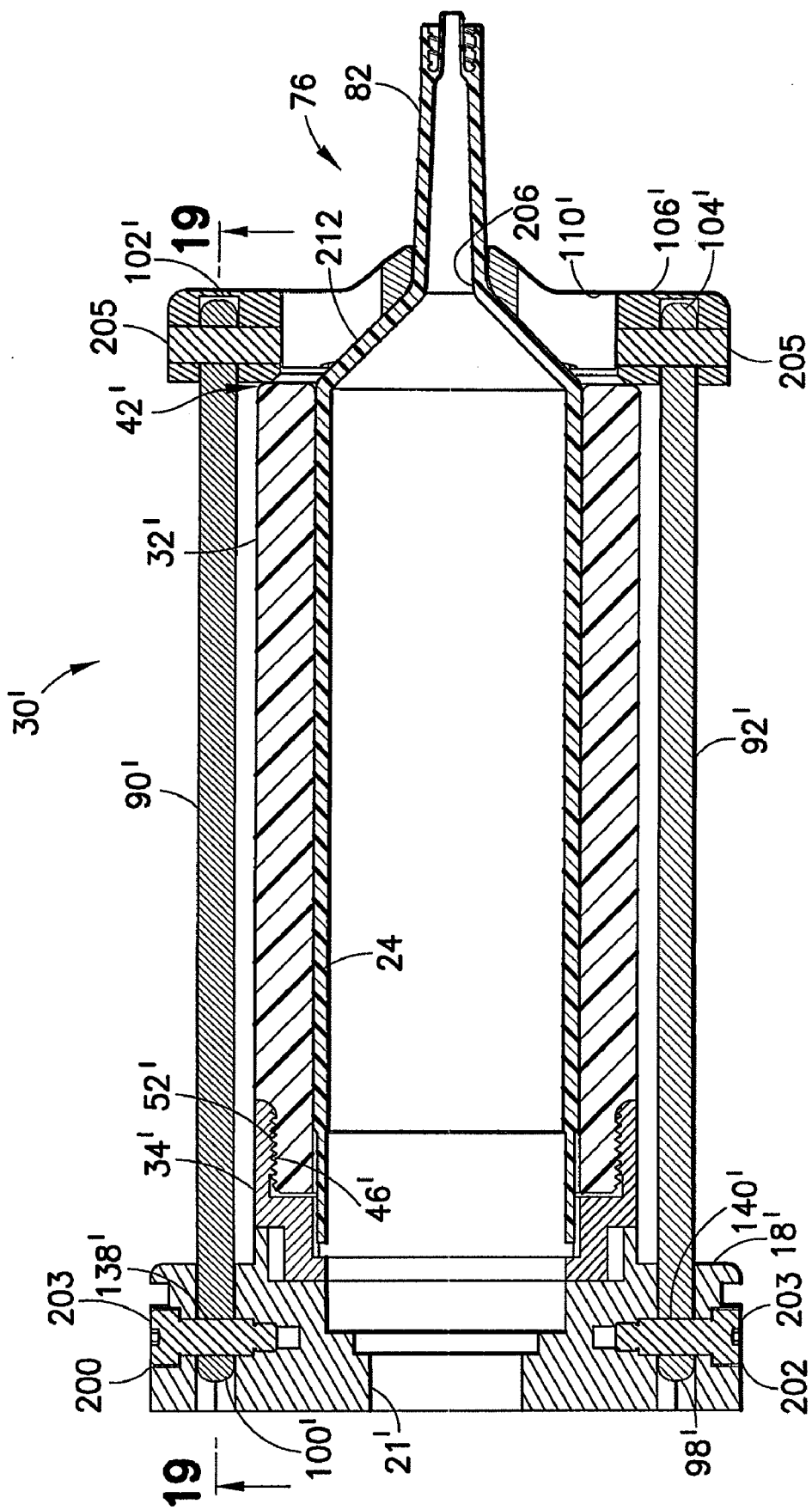
FIG. 18 is a plan cross sectional view taken along the longitudinal axis of the pressure jacket assembly of FIG. 12.

In Fig. 14, Sheet 11 of 33, delete " 32 " and insert -- 32' --, therefor.

IN THE SPECIFICATION

In Column 29, Line 8, delete "$OD_{es}$" and insert -- $OD_{cs}$ --, therefor.

In Column 33, Line 36, delete "$OD_1$" and insert -- $OD_l$ --, therefor.

Signed and Sealed this
Second Day of April, 2013

Teresa Stanek Rea
*Acting Director of the United States Patent and Trademark Office*